United States Patent
Mueller et al.

(10) Patent No.: US 7,547,694 B2
(45) Date of Patent: Jun. 16, 2009

(54) SELECTED CGRP-ANTAGONISTS, PROCESS FOR PREPARING THEM AND THEIR USE AS PHARMACEUTICAL COMPOSITIONS

(75) Inventors: Stephan Georg Mueller, Warthausen (DE); Klaus Rudolf, Warthausen (DE); Philipp Lustenberger, Warthausen (DE); Dirk Stenkamp, Biberach (DE); Kirsten Arndt, Biberach (DE); Henri Doods, Warthausen (DE); Gerhard Schaenzle, Biberach-Mettenberg (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/775,443

(22) Filed: Jul. 10, 2007

(65) Prior Publication Data

US 2007/0275951 A1 Nov. 29, 2007

Related U.S. Application Data

(63) Continuation of application No. 11/107,189, filed on Apr. 15, 2005, now Pat. No. 7,279,471.

(30) Foreign Application Priority Data

Apr. 15, 2004 (DE) ........................ 10 2004 018 794

(51) Int. Cl.
*A61K 31/537* (2006.01)
*C07D 413/14* (2006.01)
*C07D 471/10* (2006.01)
*C07D 405/14* (2006.01)

(52) U.S. Cl. .............. 514/228.8; 514/278; 544/96; 544/130; 546/17; 546/20; 546/187; 548/314.7; 548/517

(58) Field of Classification Search .............. 514/228.8, 514/278; 544/96, 130; 546/17, 20, 187; 548/314.7, 517
See application file for complete search history.

(56) References Cited

U.S. PATENT DOCUMENTS

| 6,344,449 | B1 | 2/2002 | Rudolf et al. |
| 7,279,471 | B2 * | 10/2007 | Mueller et al. ........... 514/228.8 |
| 2003/0236282 | A1 | 12/2003 | Hurnaus et al. |
| 2004/0063735 | A1 | 4/2004 | Chaturvedula et al. |

FOREIGN PATENT DOCUMENTS

WO WO03076432 A1 9/2003

OTHER PUBLICATIONS

John J. Mallee, et al; Receptor Activity-modifying Protein 1 Determines the Species Selectivity of Non-peptide CGRP Receptor Antagonists; The Journal of Biological Chemistry; vol. 277, No. 16, Apr. 19, 2002, pp. 14294-14298; The American Society for Biochemistry and Molecular Biology, Inc.

* cited by examiner

Primary Examiner—Rei-Tsang Shiao
Assistant Examiner—Joseph R Kosack
(74) Attorney, Agent, or Firm—Michael P. Morris; Mary-Ellen M. Devlin; Alan R. Stempel

(57) ABSTRACT

The present invention relates to the CGRP antagonists of general formula

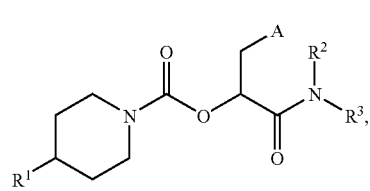

wherein A and $R^1$ to $R^3$ are defined as in claim 1, the tautomers, the diastereomers, the enantiomers, the hydrates thereof, the mixtures thereof and the salts thereof and the hydrates of the salts, particularly the physiologically acceptable salts thereof with inorganic or organic acids, pharmaceutical compositions containing these compounds, the use thereof and processes for the preparation thereof.

15 Claims, No Drawings

SELECTED CGRP-ANTAGONISTS, PROCESS FOR PREPARING THEM AND THEIR USE AS PHARMACEUTICAL COMPOSITIONS

RELATED APPLICATIONS

This application is a continuation of U.S. patent application Ser. No. 11/107,189, filed on Apr. 15, 2005 now U.S. Pat. No. 7,279,471 and claims benefit of U.S. Ser. No. 60/570,006, filed May 11, 2004, the entireties of which are incorporated herein by reference.

FIELD OF THE INVENTION

The present invention relates to the CGRP antagonists of general formula

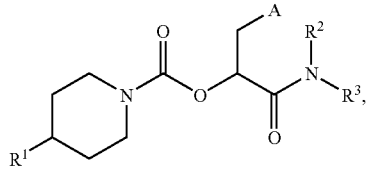

(I)

the tautomers, the diastereomers, the enantiomers, the hydrates thereof, the mixtures thereof and the salts thereof as well as the hydrates of the salts, particularly the physiologically acceptable salts thereof with inorganic or organic acids, pharmaceutical compositions containing these compounds, their use and processes for preparing them.

In the above general formula (I)

A denotes a group of formula

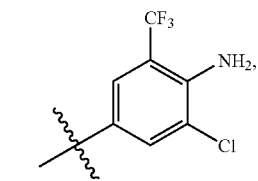
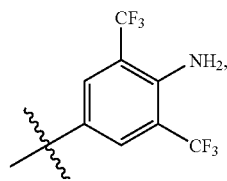

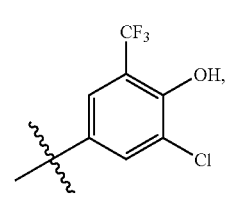
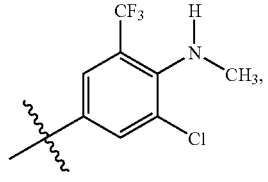

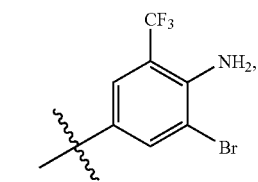
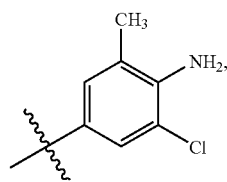

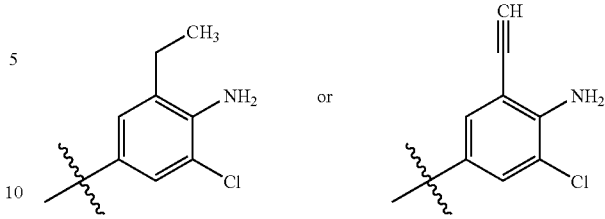

the group

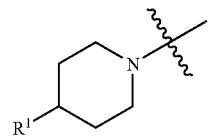

denotes a group of formula

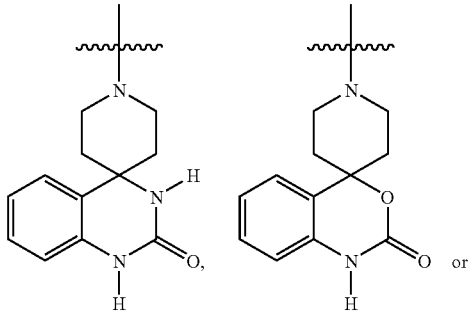

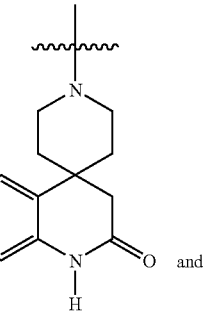

and

—$NR^2R^3$ denotes a group of formula

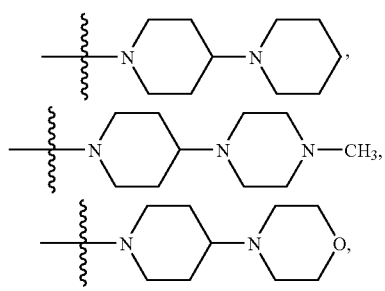

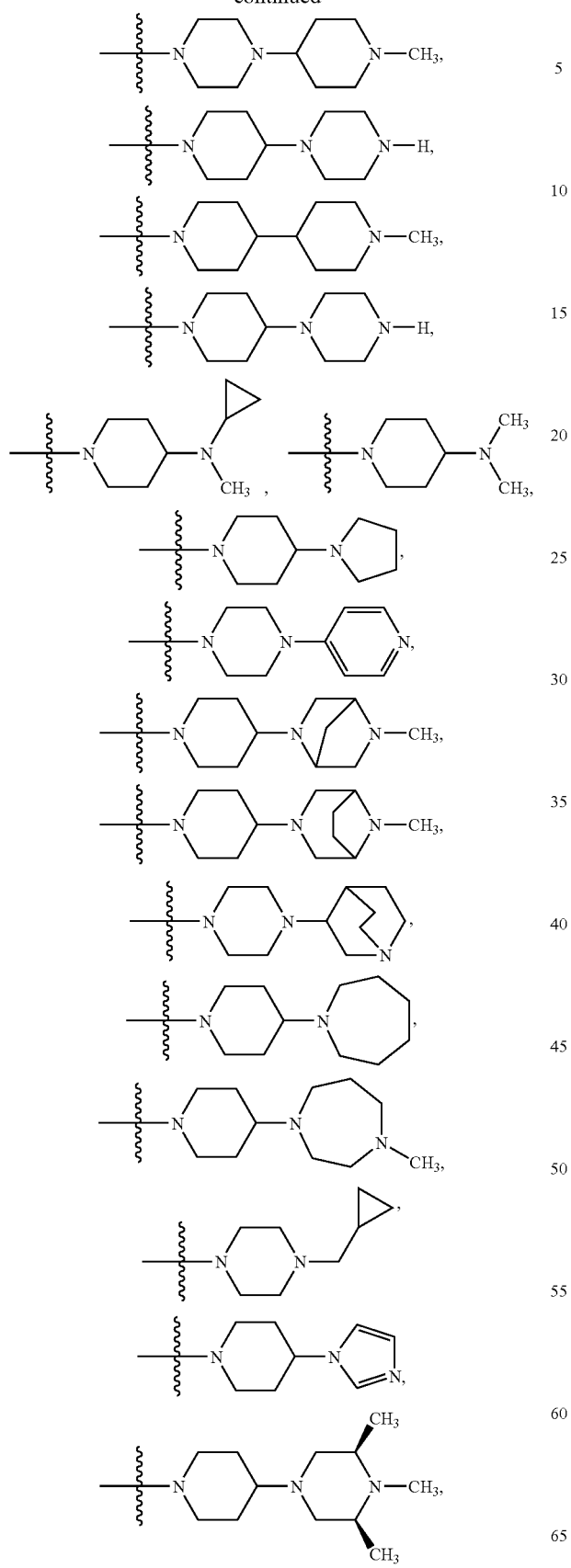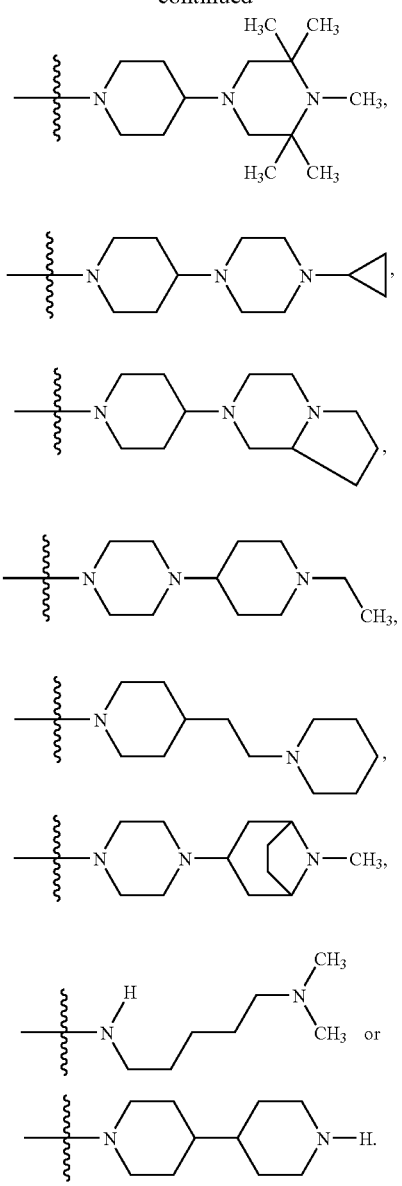
Particularly preferred compounds of the above general formula (I) are as follows, for example:
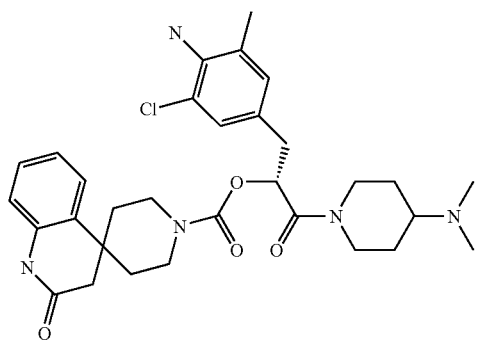

-continued
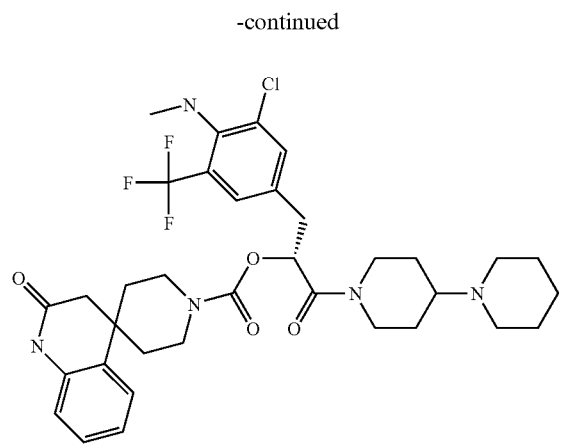
2
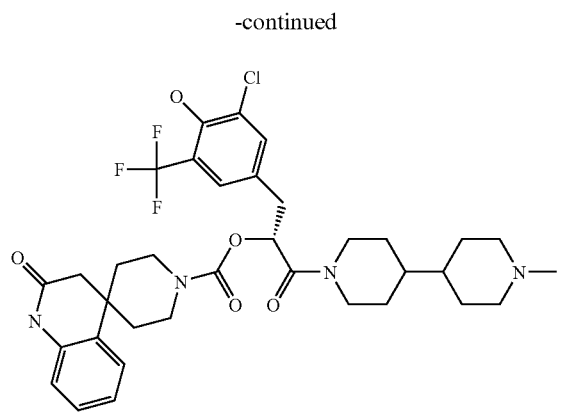
6
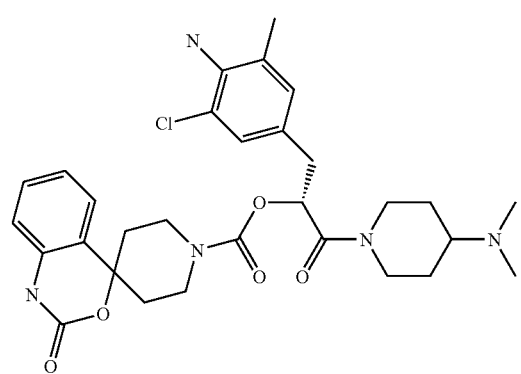
3
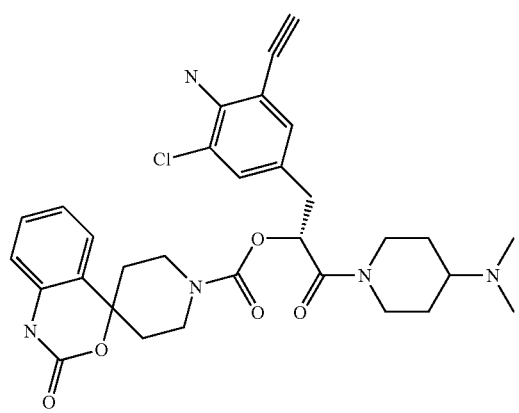
7
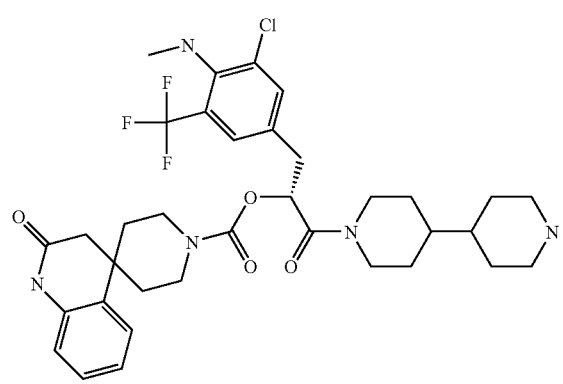
4
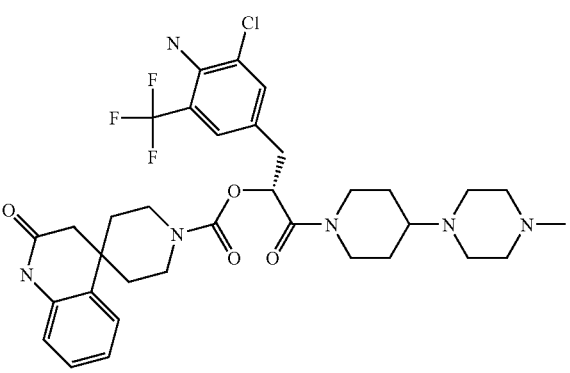
8
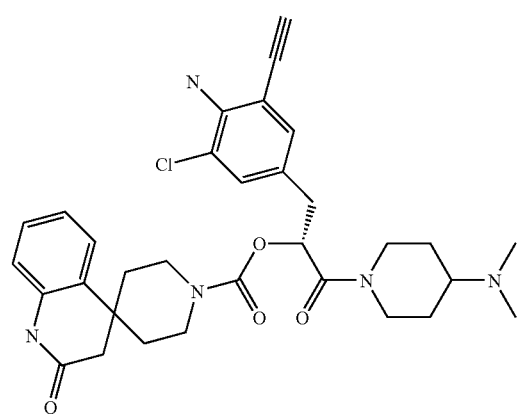
5
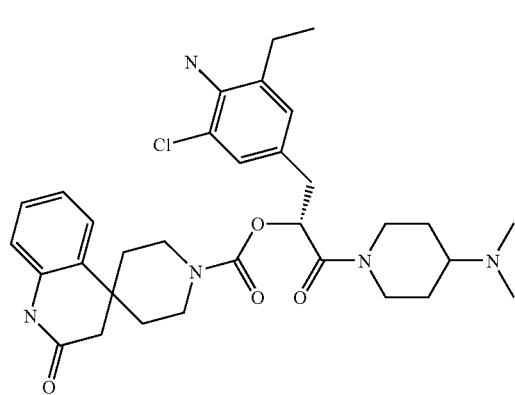
9

10
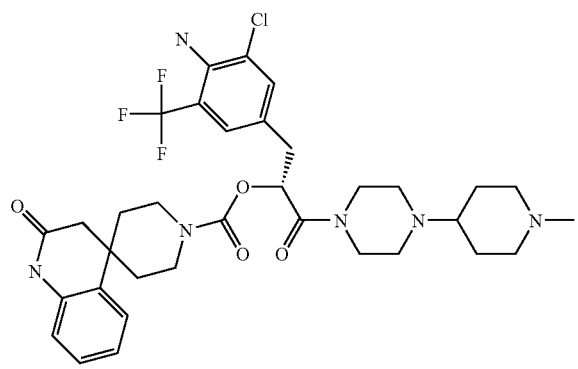
11
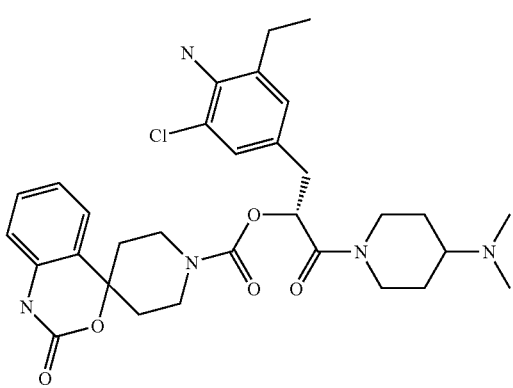
12
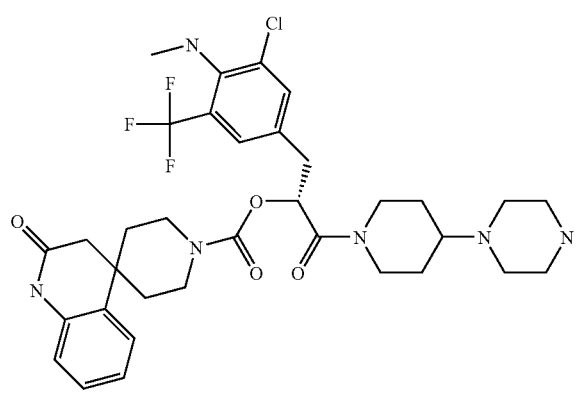
13
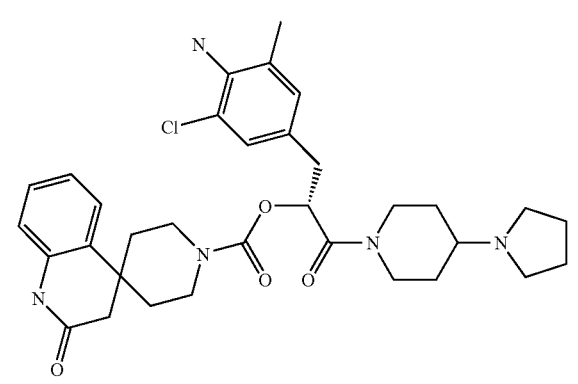
14
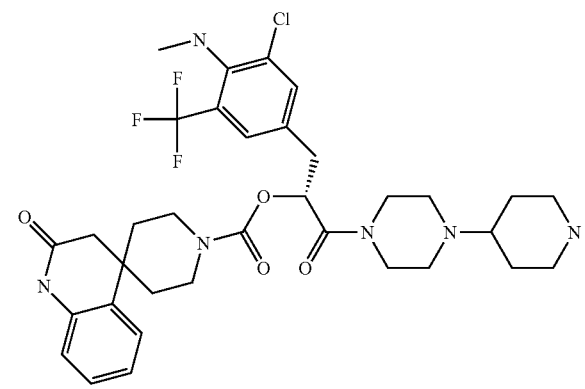
15
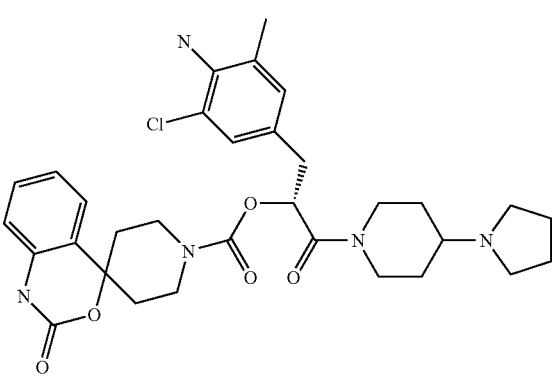
16
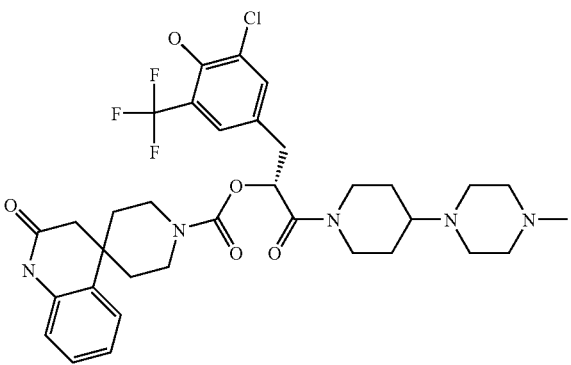
17
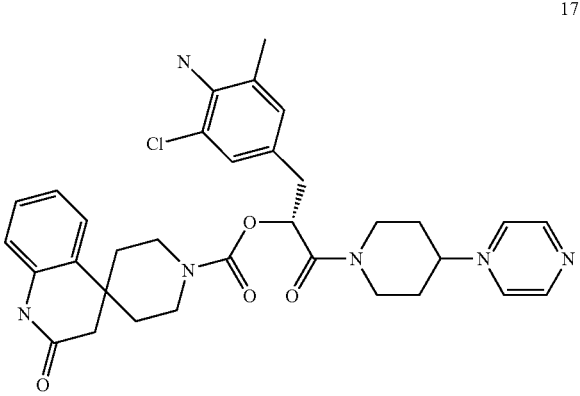

-continued
18
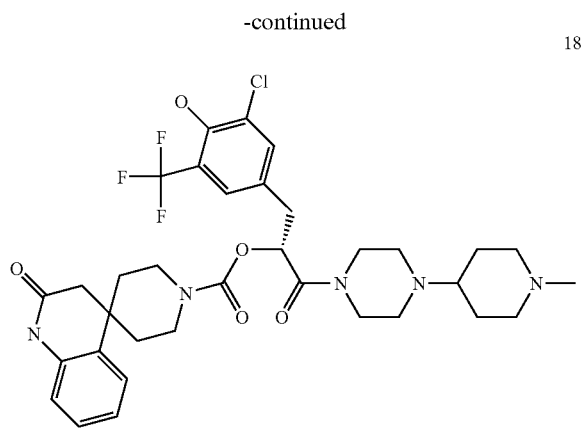
19
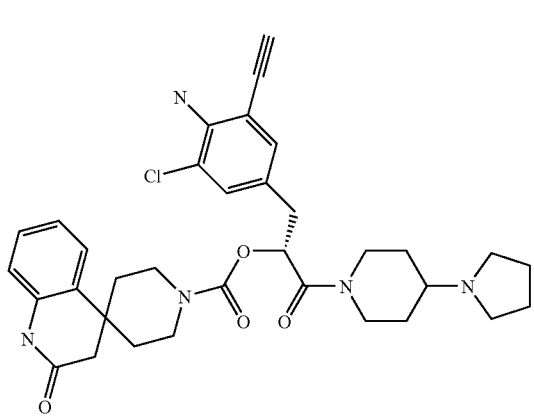
20
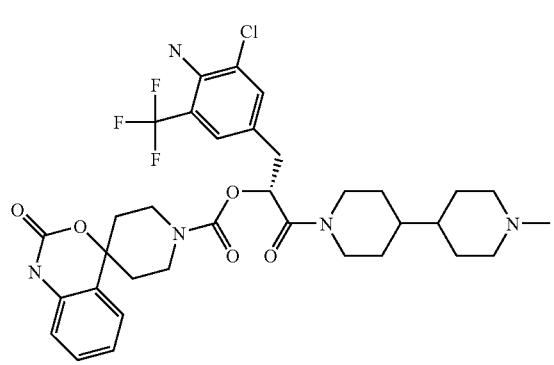
21
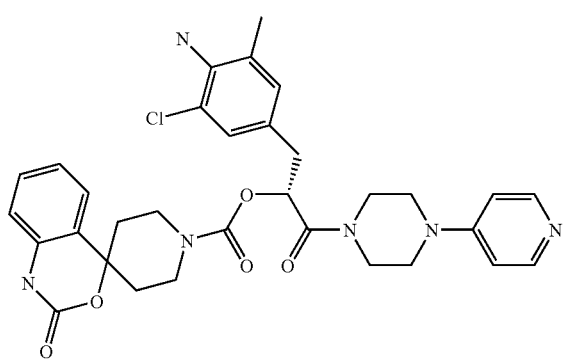
-continued
22
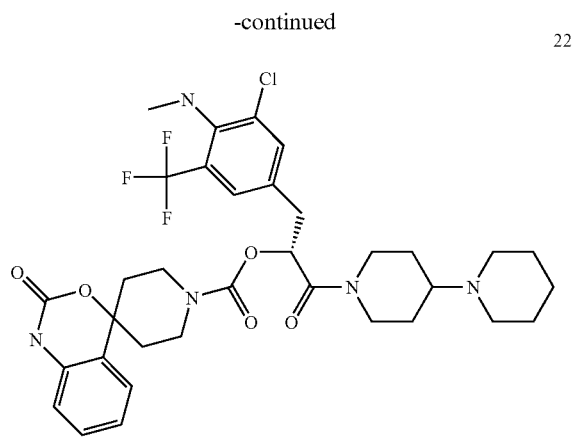
23
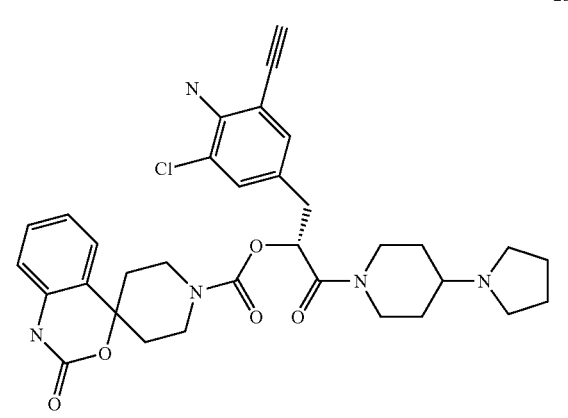
24
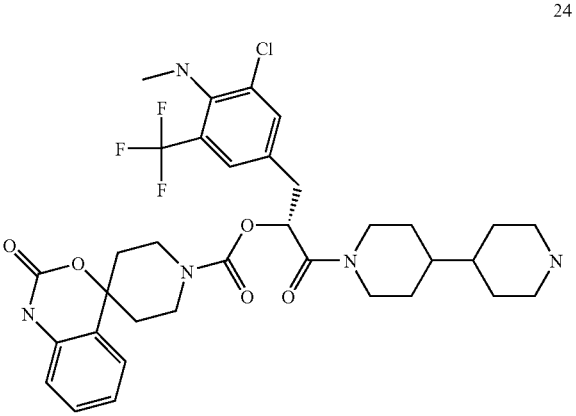
25
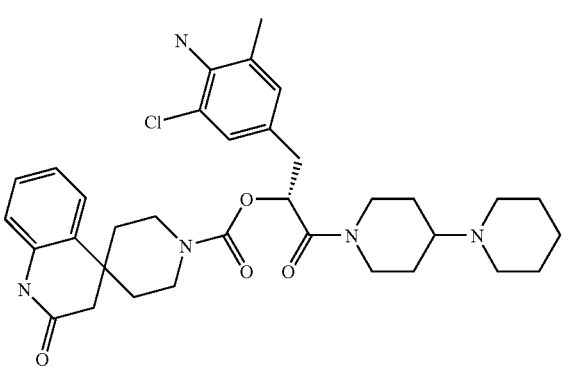

-continued
26
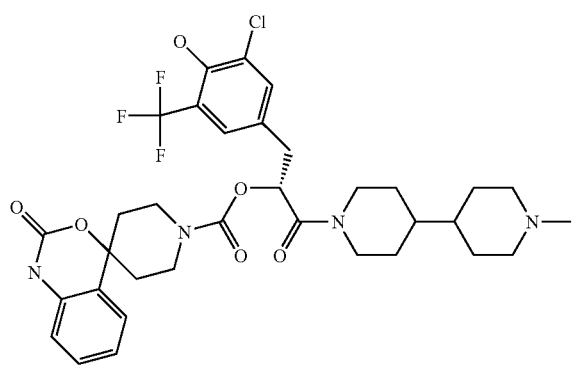
27
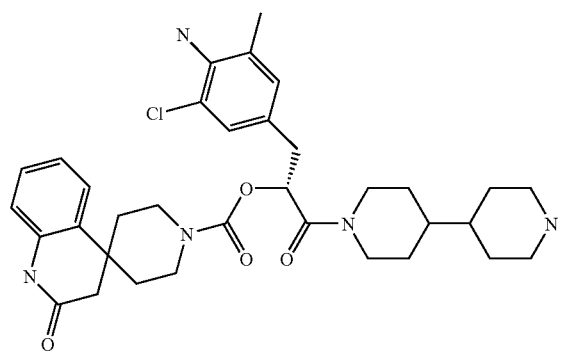
28
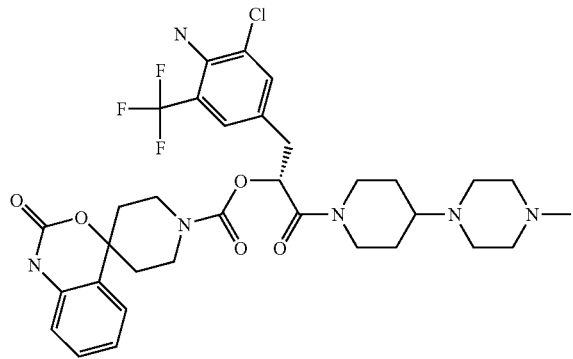
29
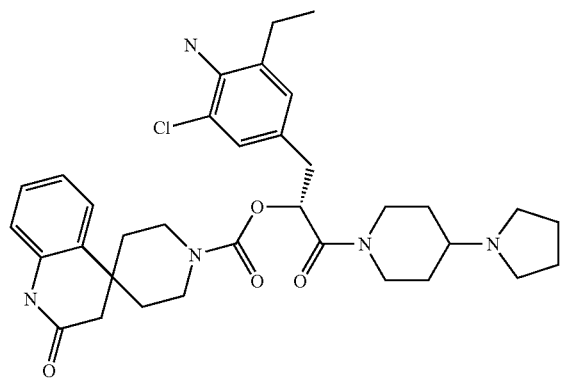
-continued
30
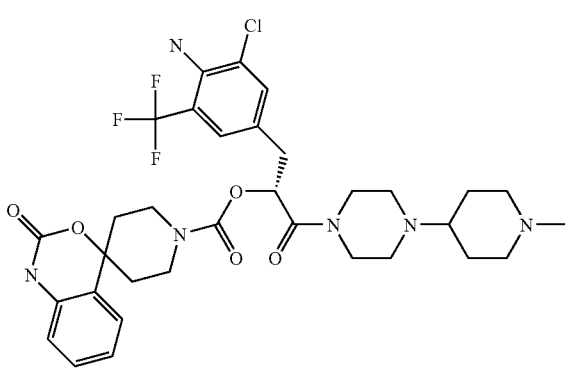
31
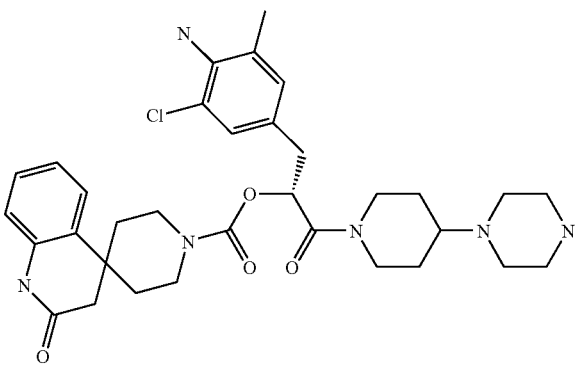
32
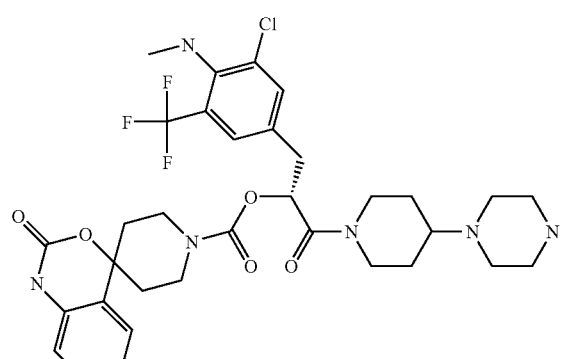
33
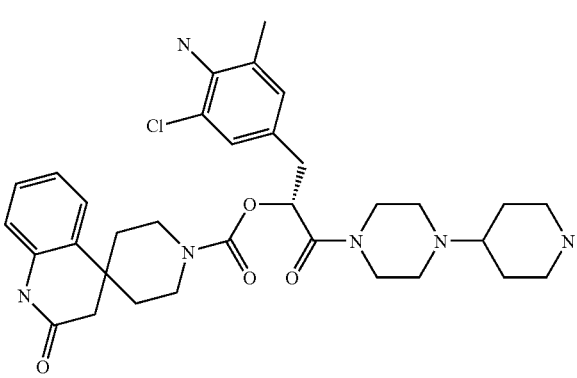

34
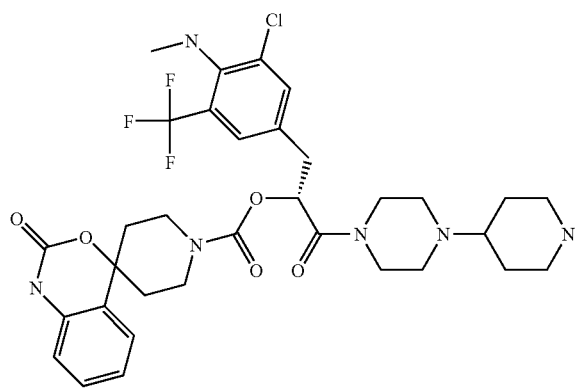
35
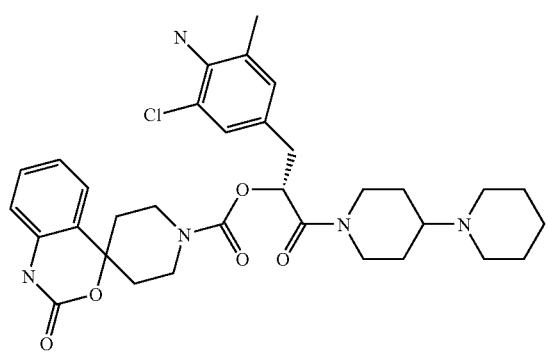
36
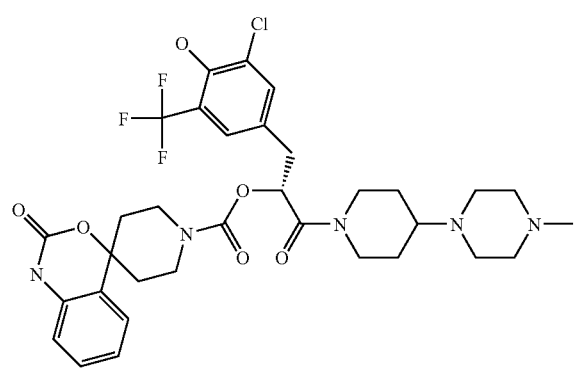
37
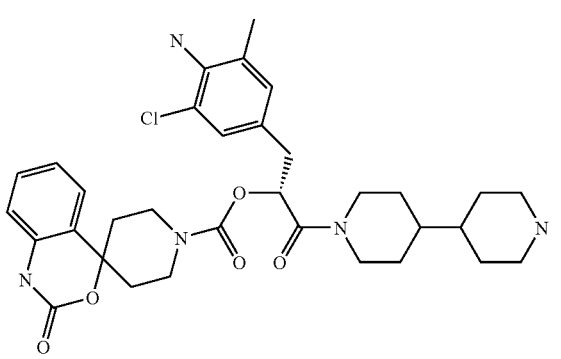
38
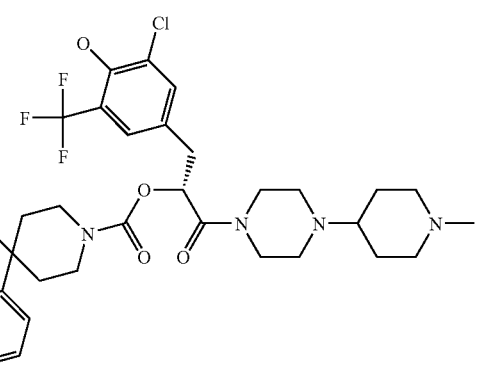
39
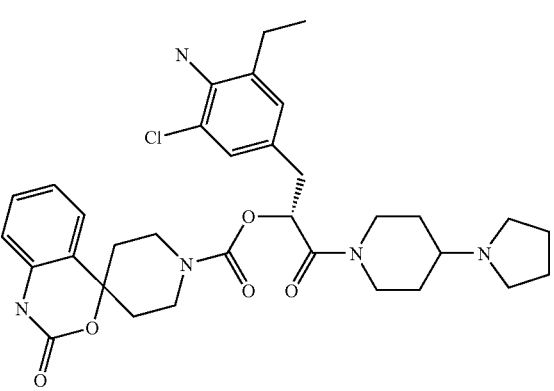
40
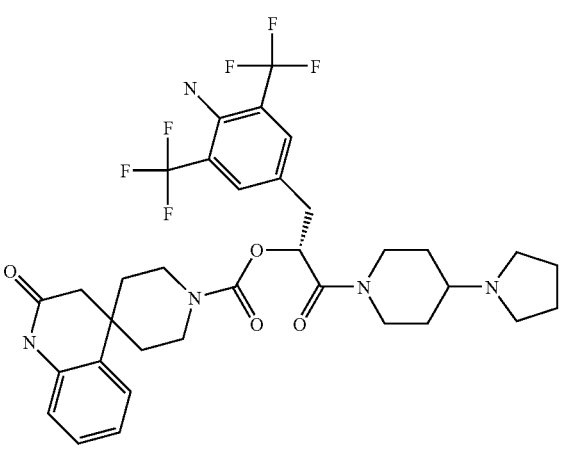
41
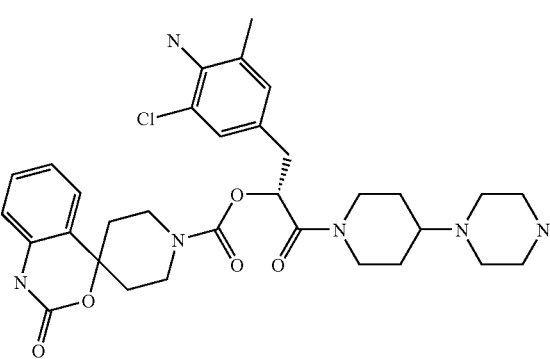

-continued
42
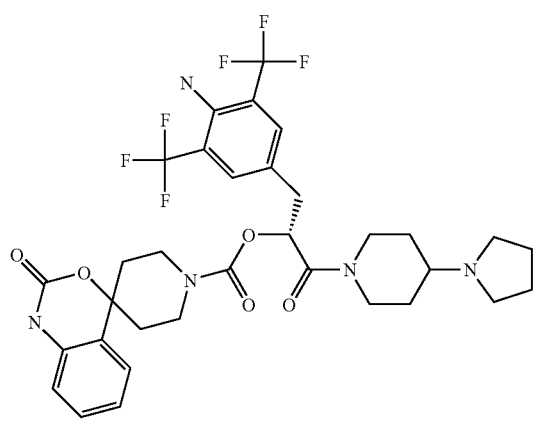
43
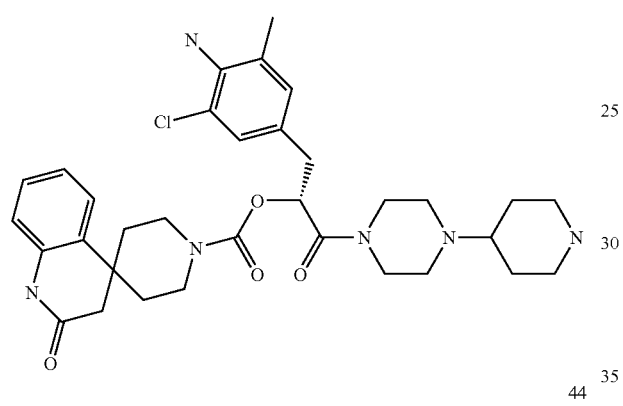
44
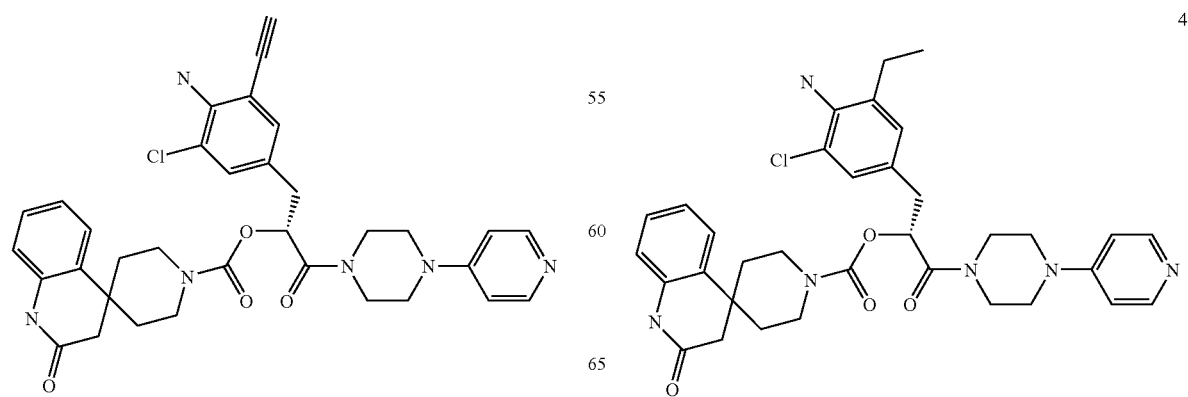
46
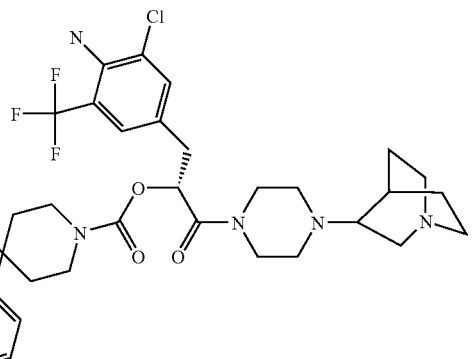
47
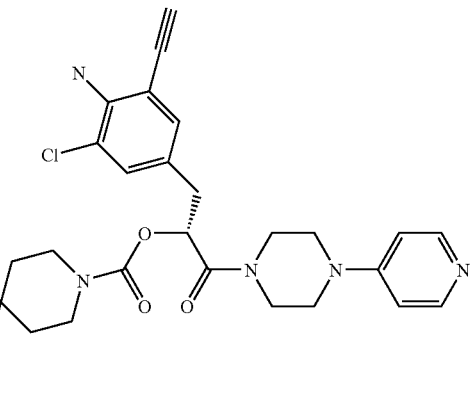
48
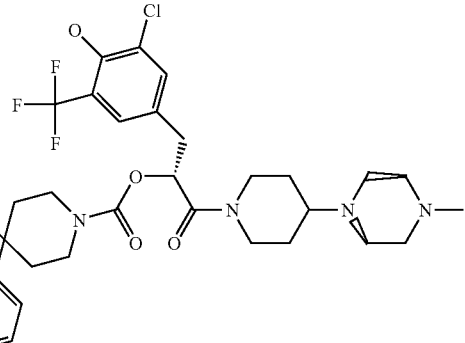
49

-continued
50
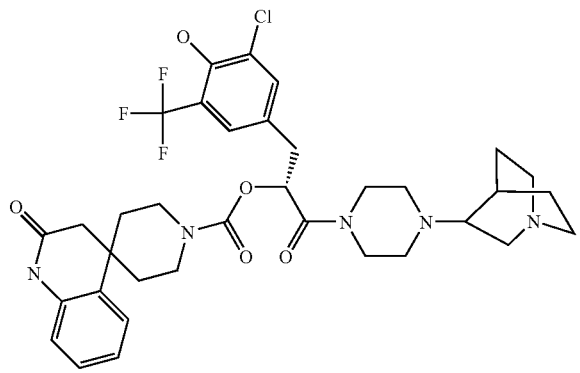
51
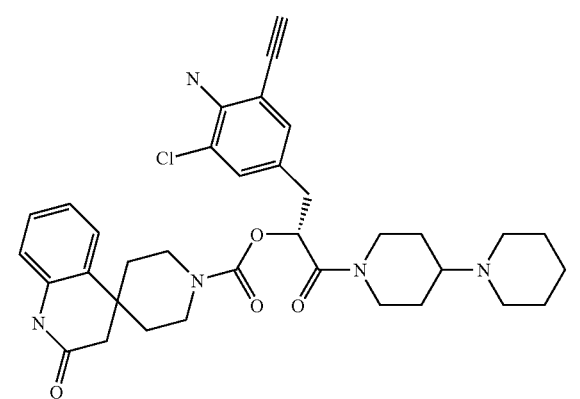
52
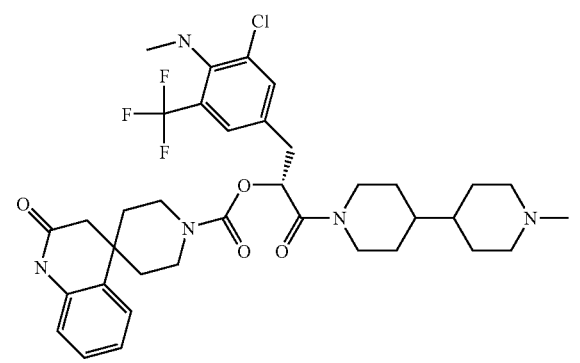
53
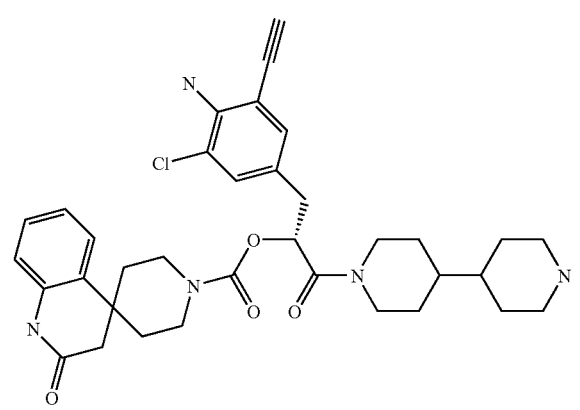
-continued
54
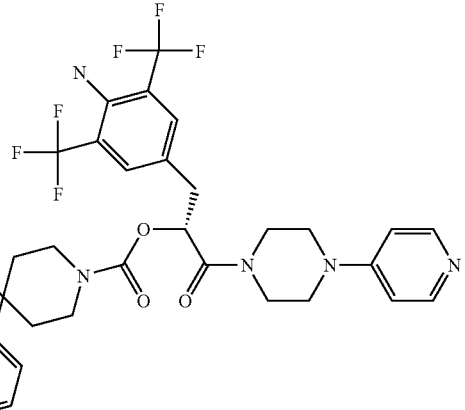
55
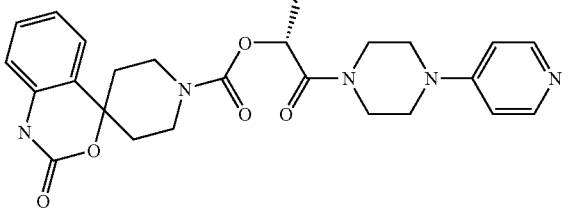
56
57
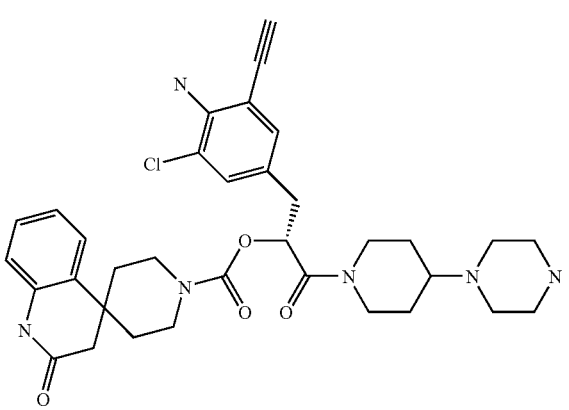

-continued
58
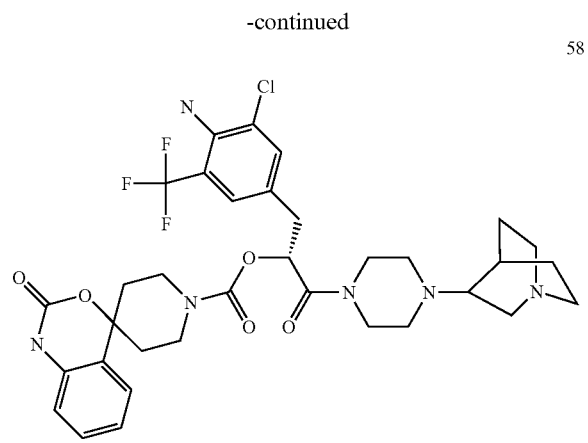
59
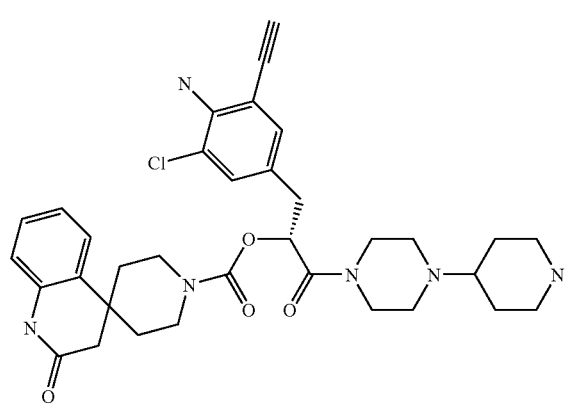
60
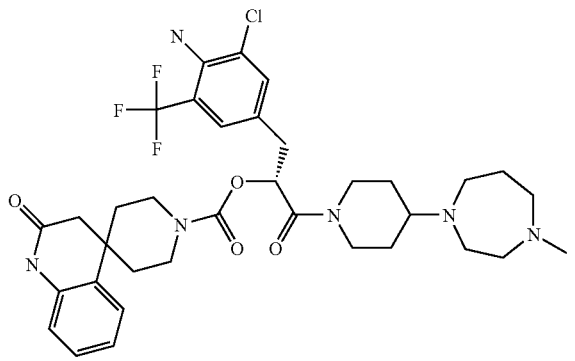
61
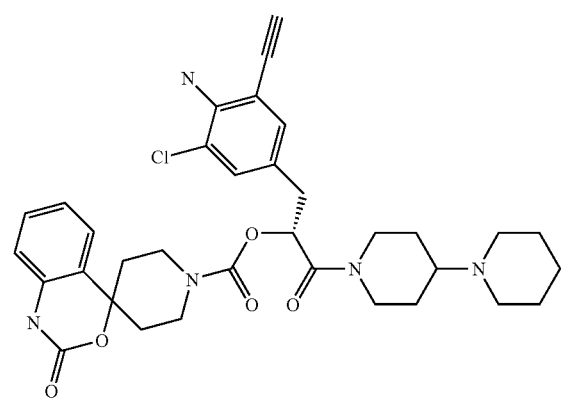
-continued
62
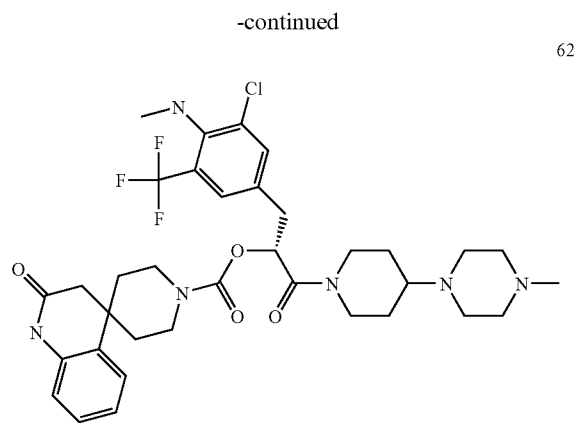
63
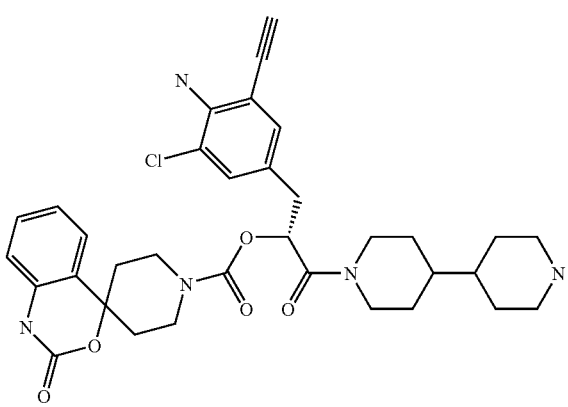
64
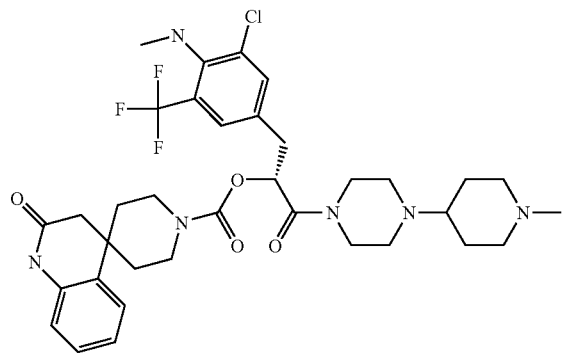
65
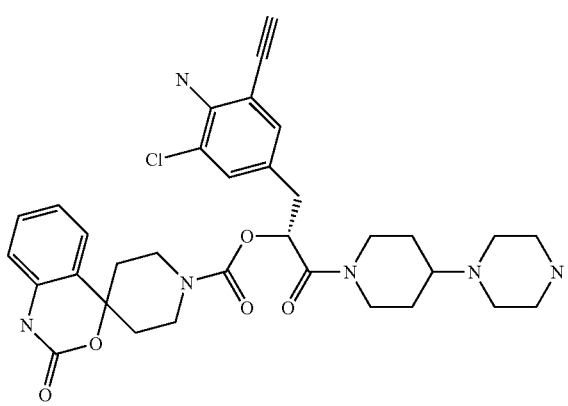

-continued
66
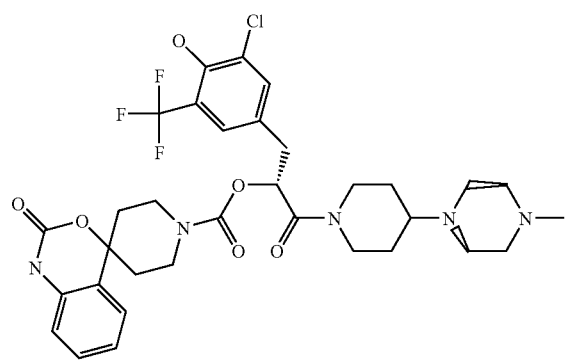
67
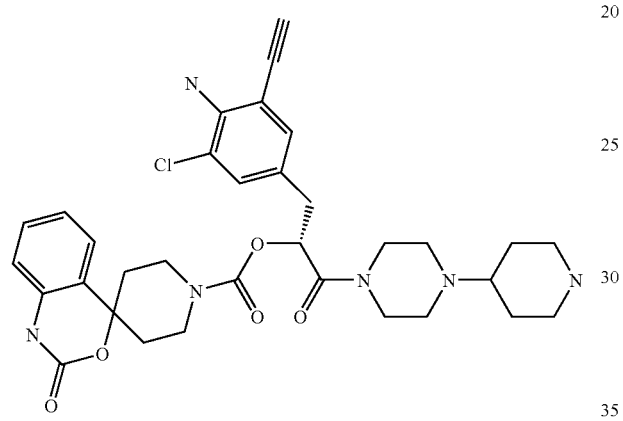
68
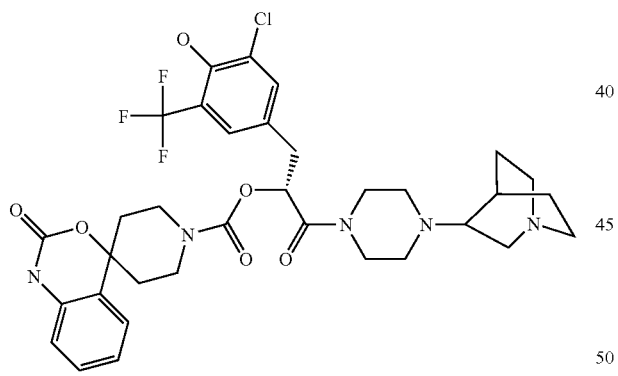
69
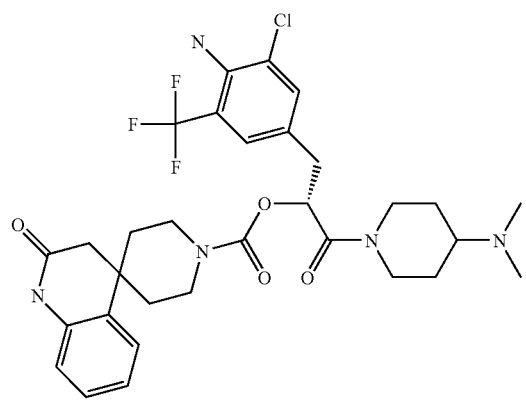
-continued
70
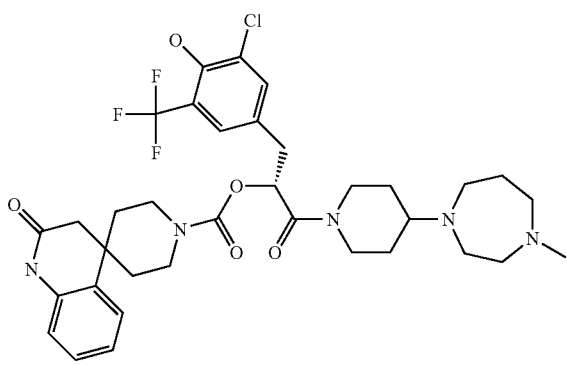
71
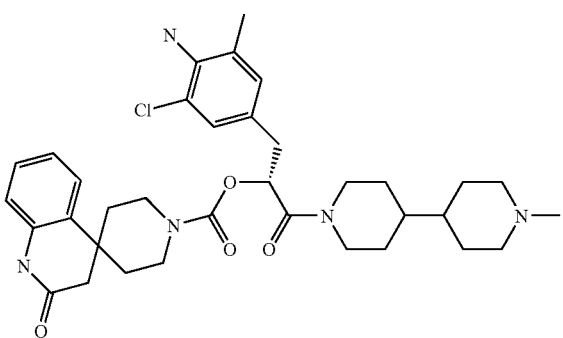
72
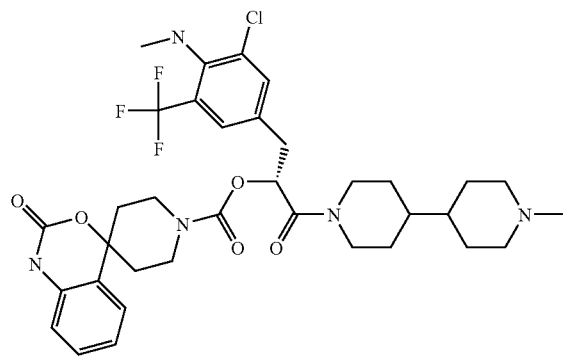
73
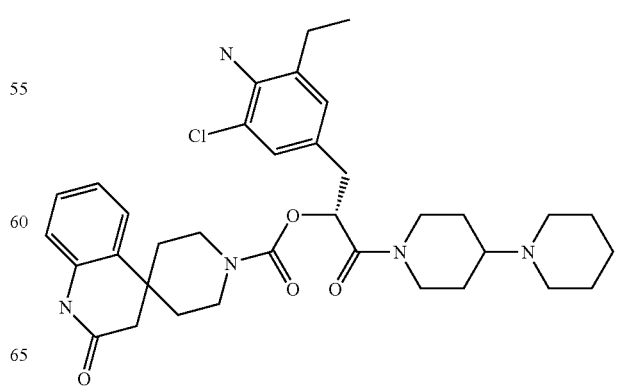

74
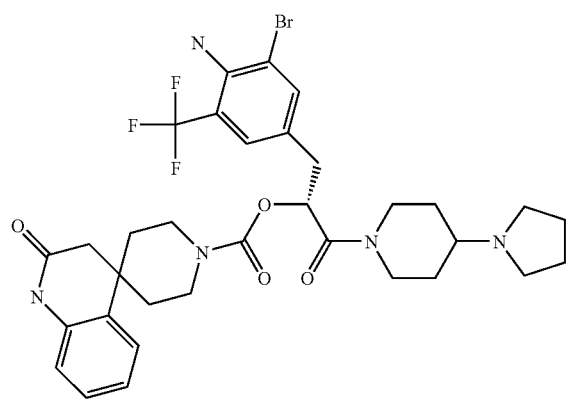
75
78
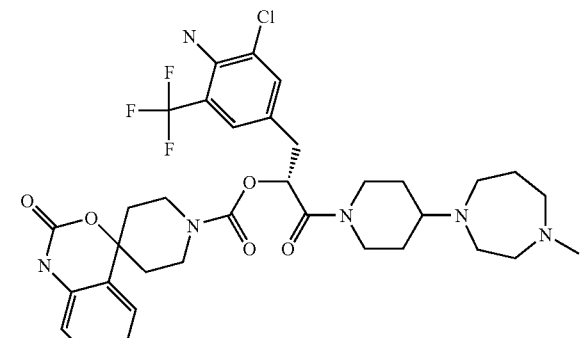
79
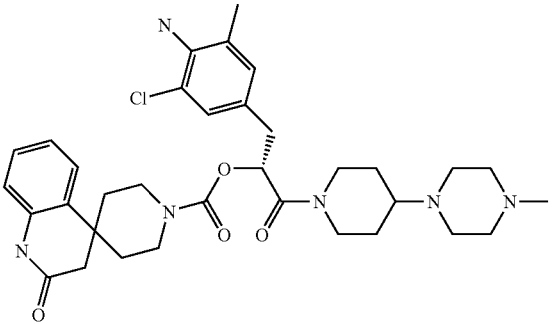
76
80
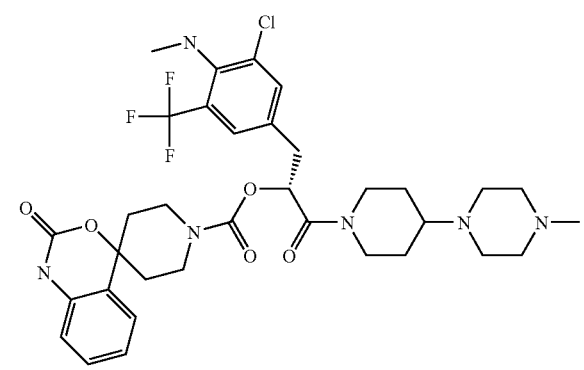
77
81
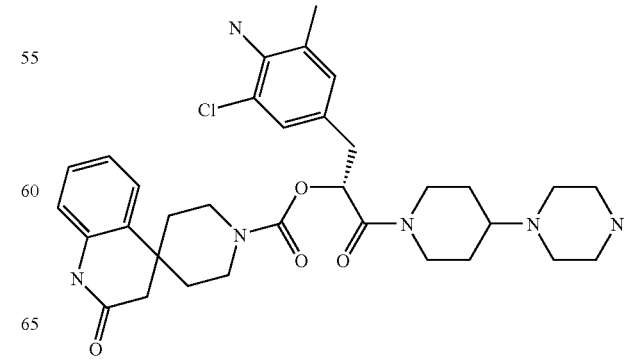

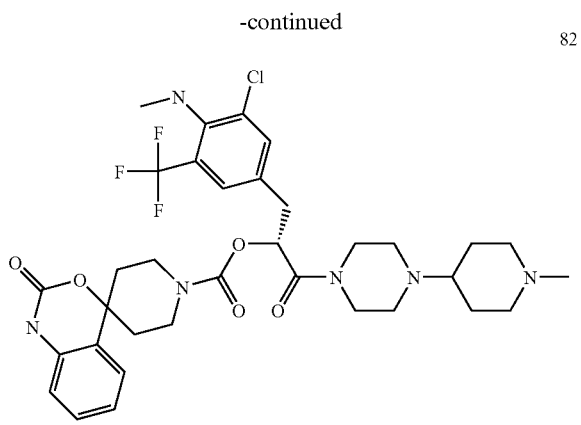
82
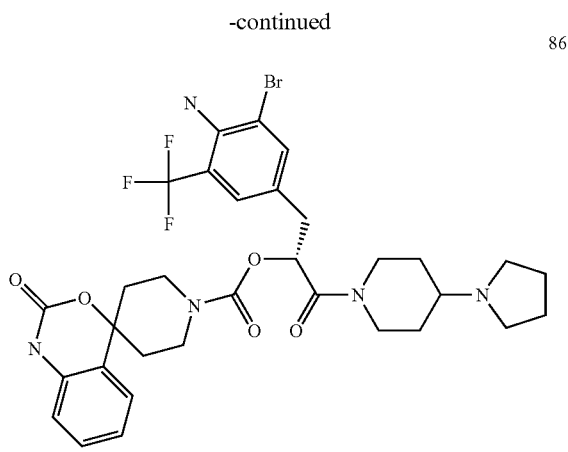
86
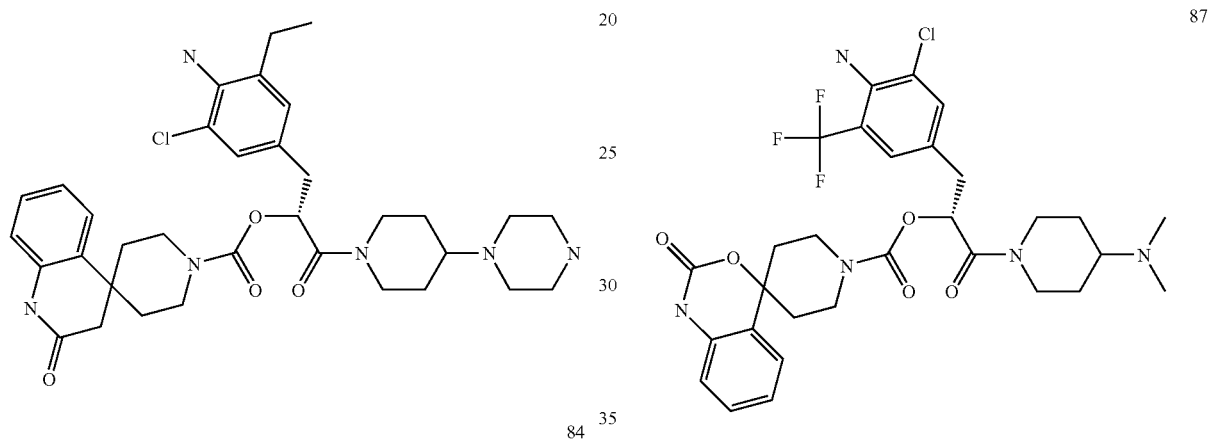
83
87
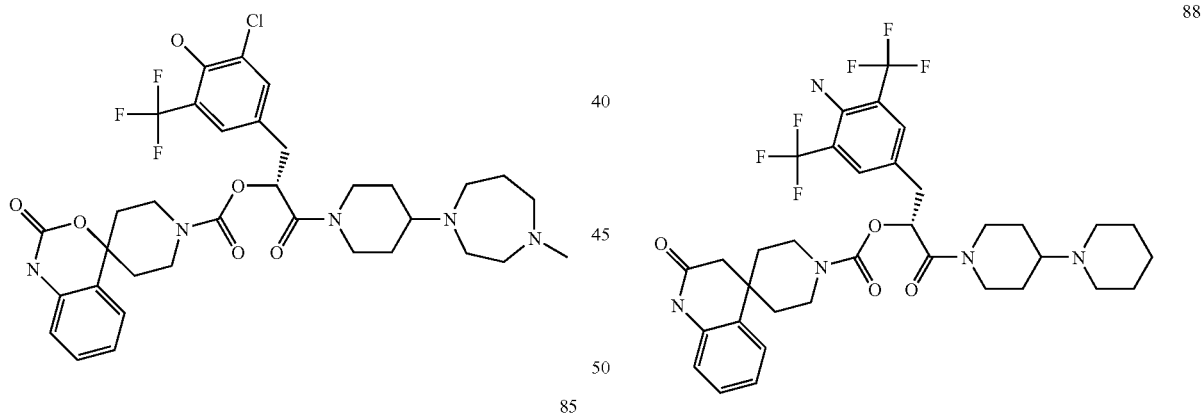
84
88
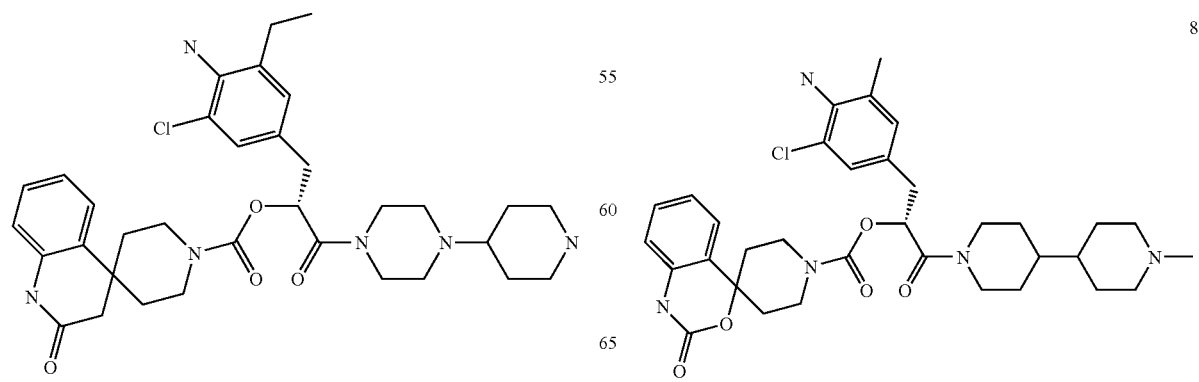
85
89

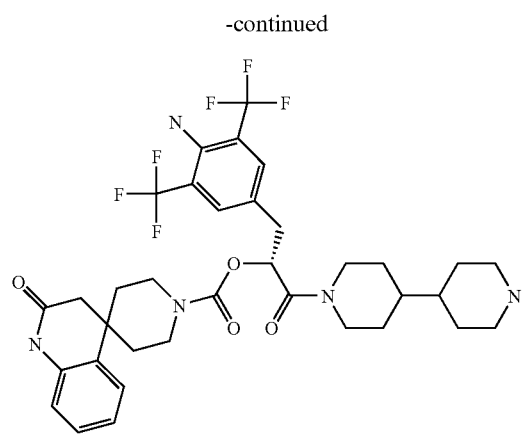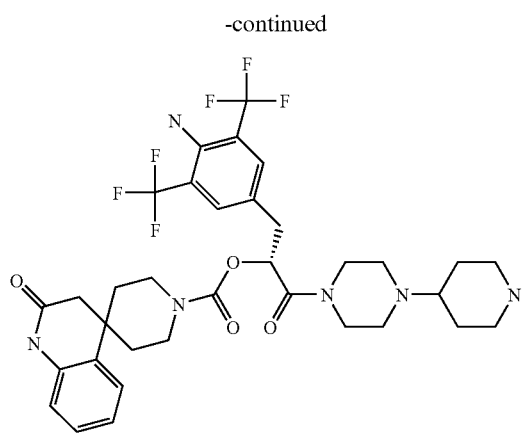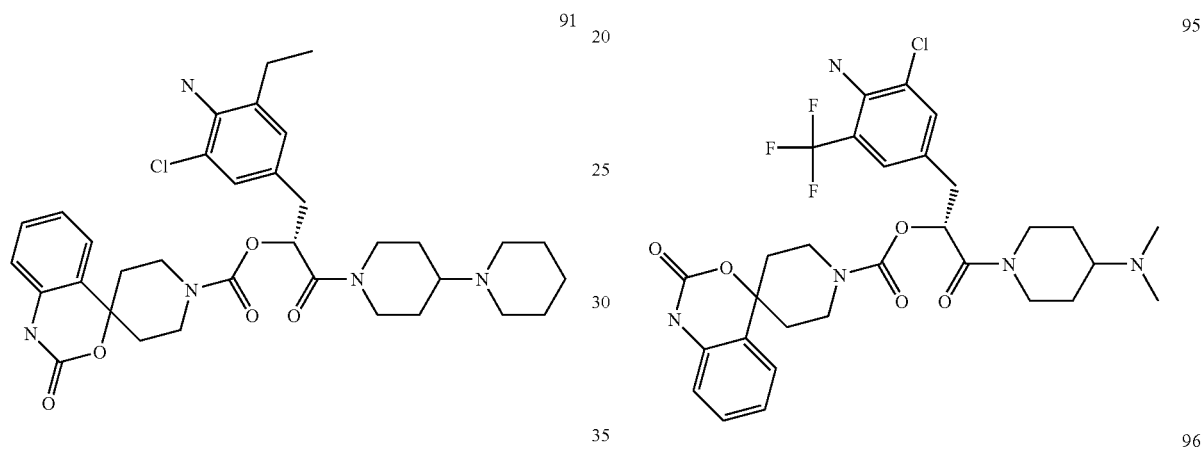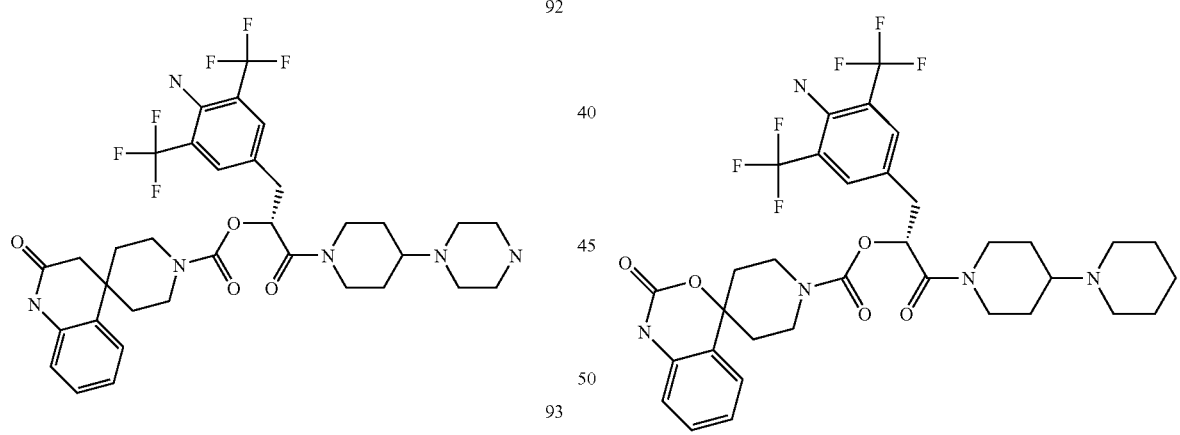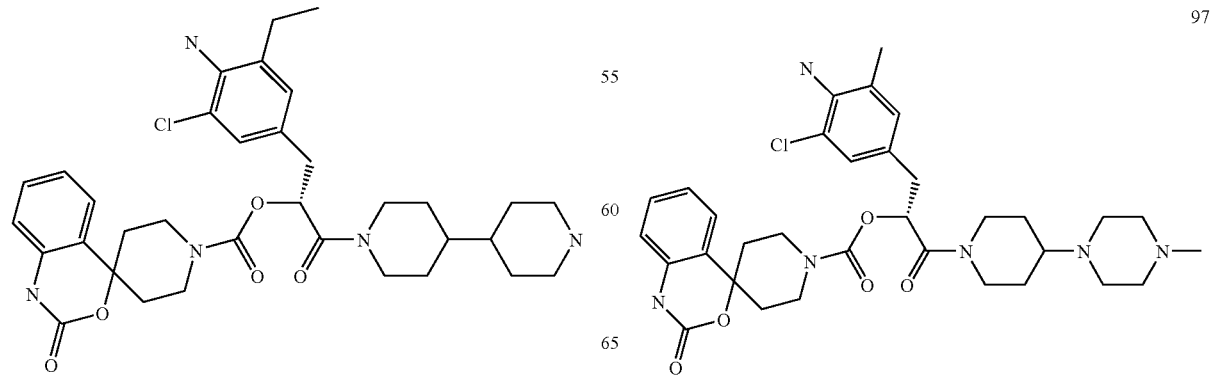

98
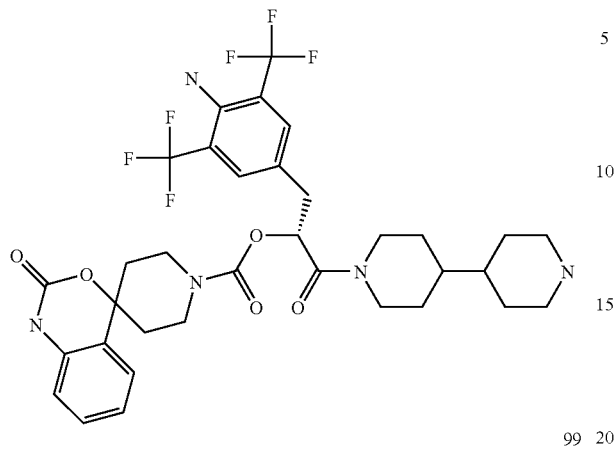
99
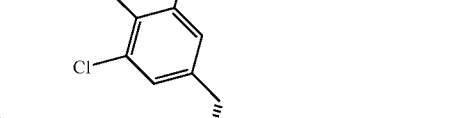
100
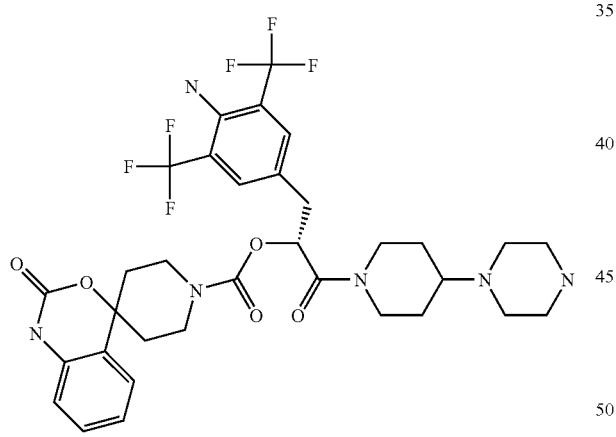
101
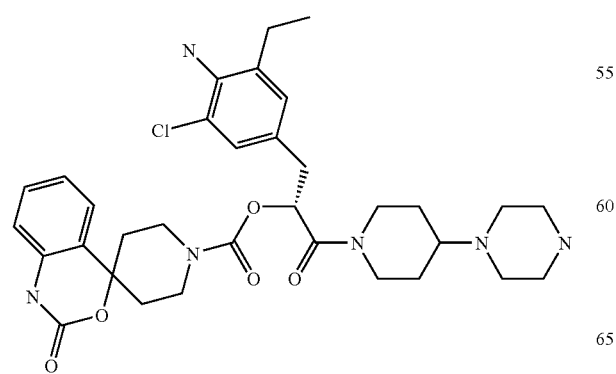
102
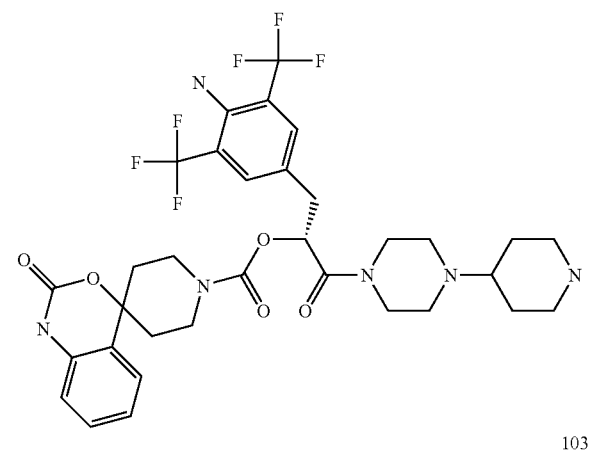
103
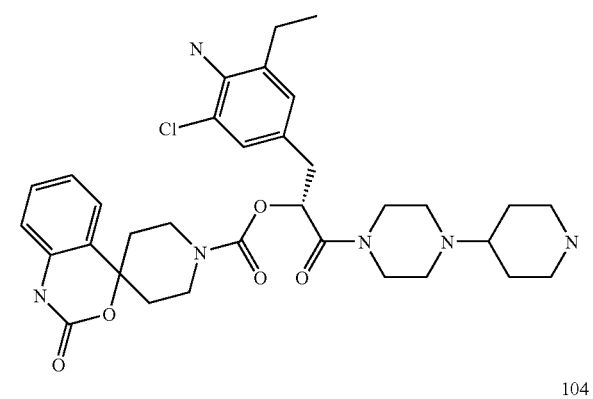
104
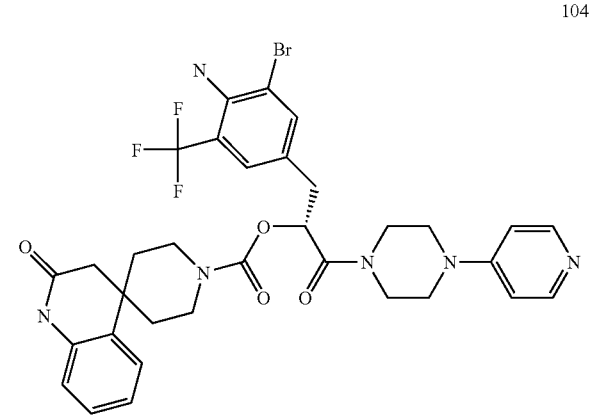
105
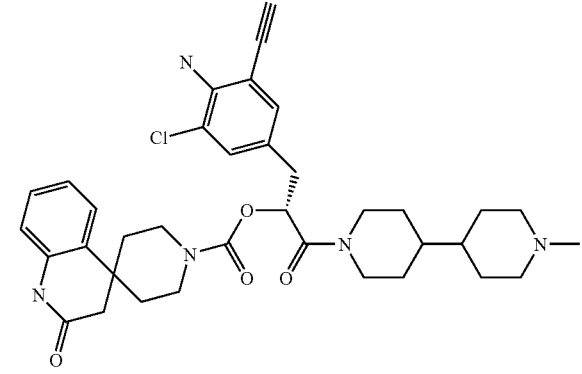

106
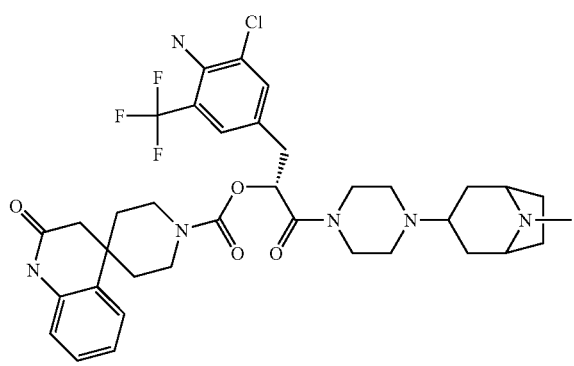
110
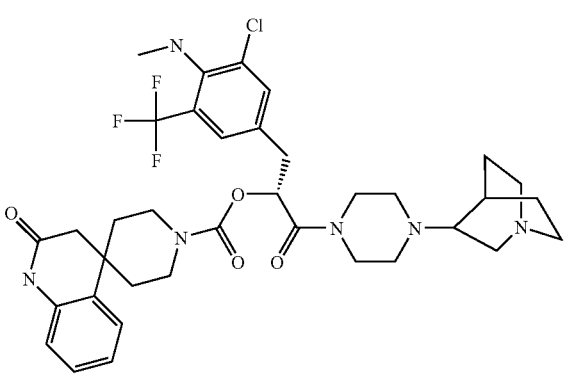
107
108
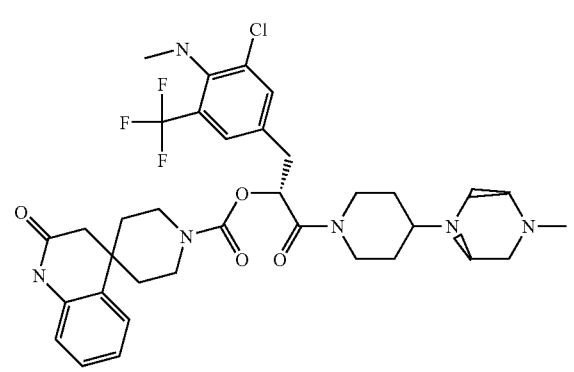
111
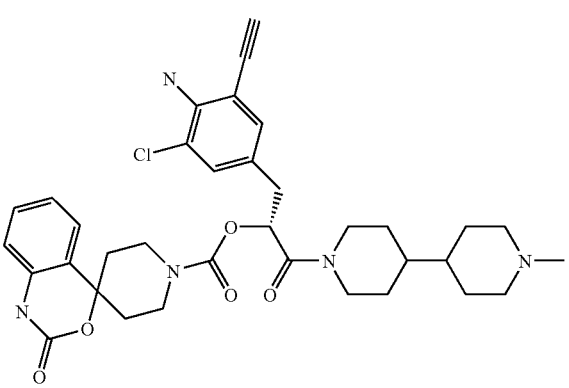
112
109
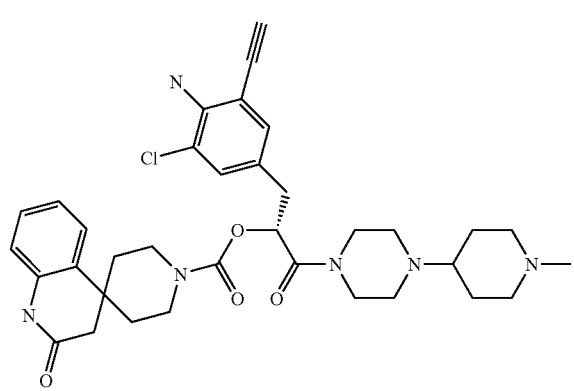
113
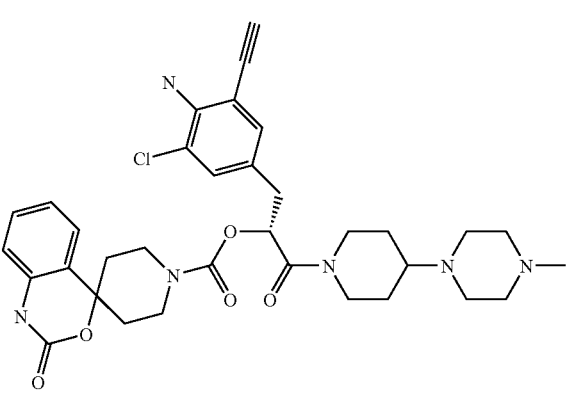

-continued
114
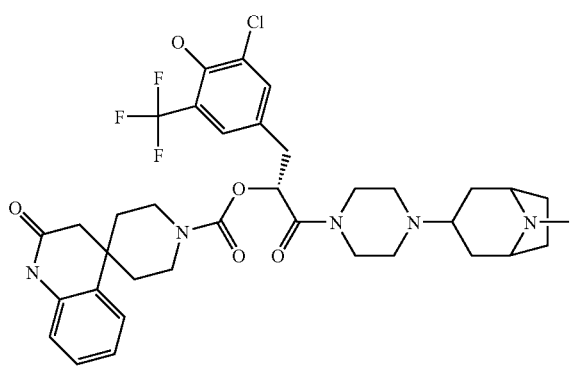
115
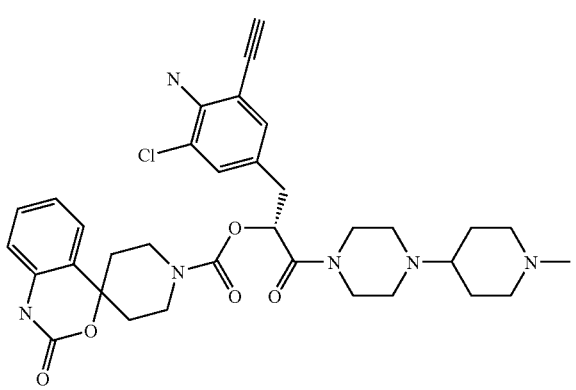
116
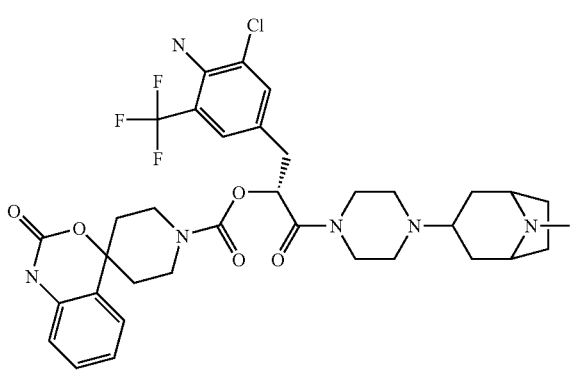
117
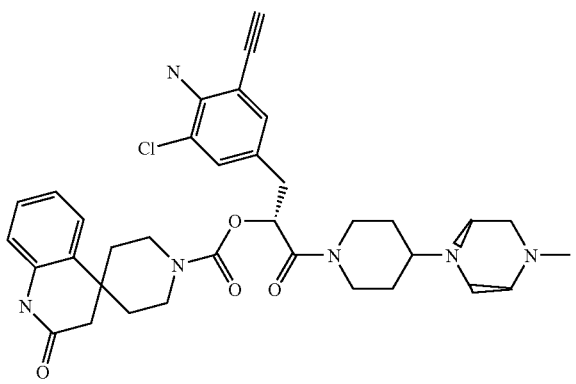
-continued
118
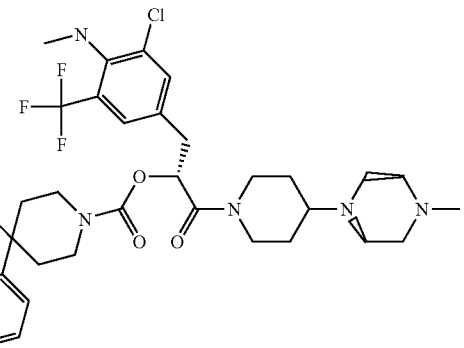
119
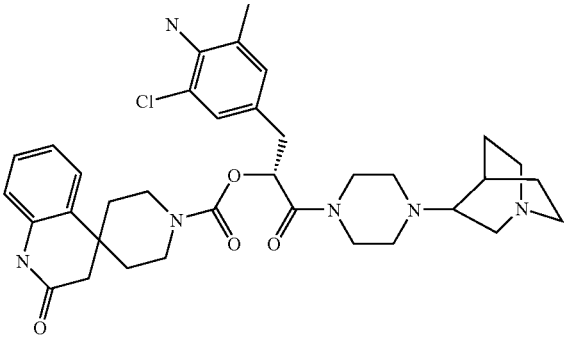
120
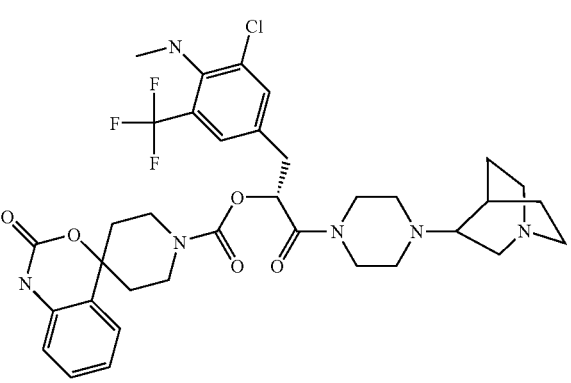
121
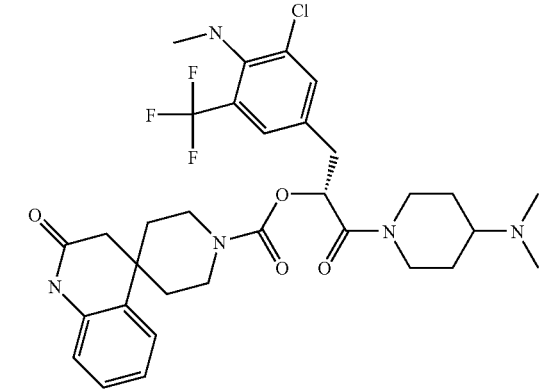

-continued
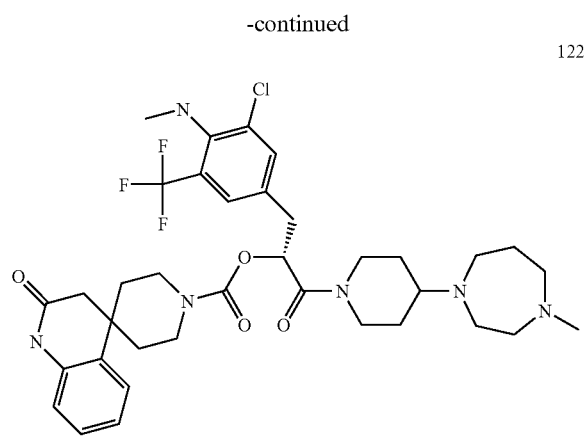
122
123
124
125
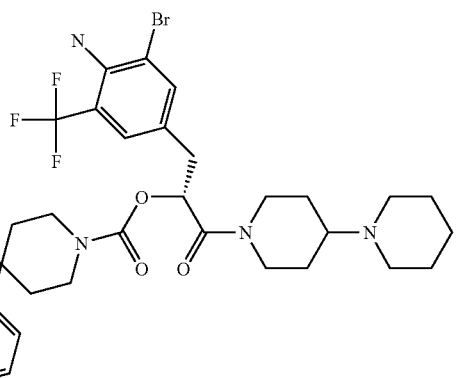
126
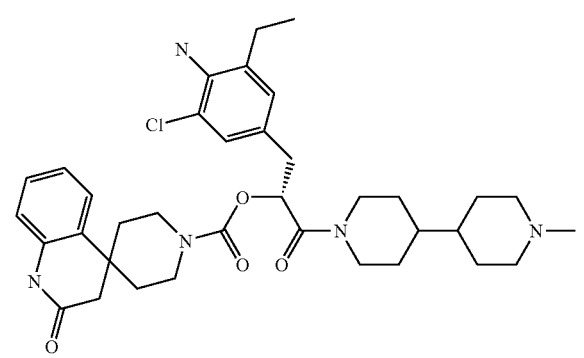
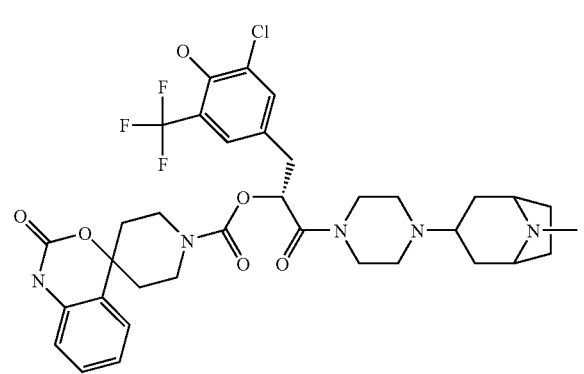
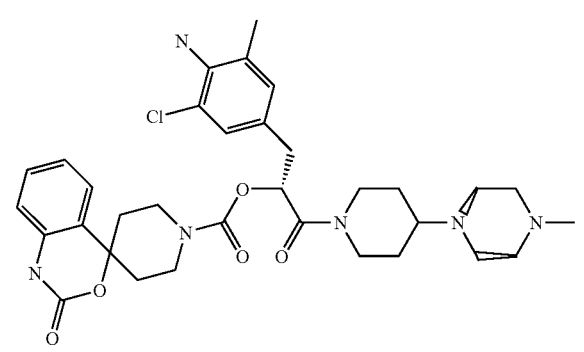
127
128
129

-continued
130
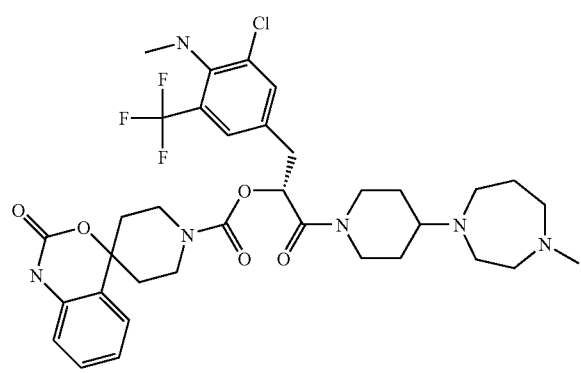
131
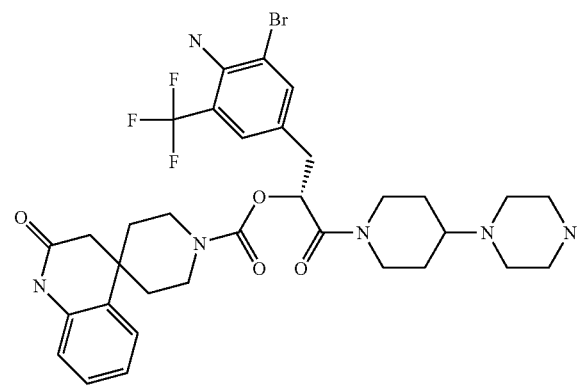
132
133
-continued
134
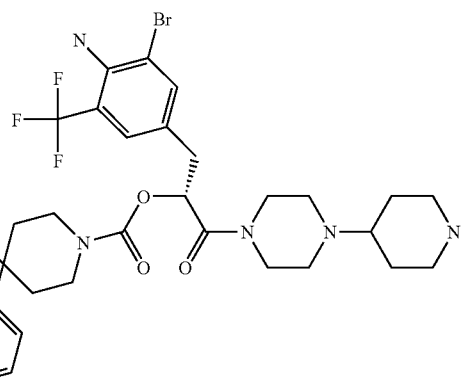
135
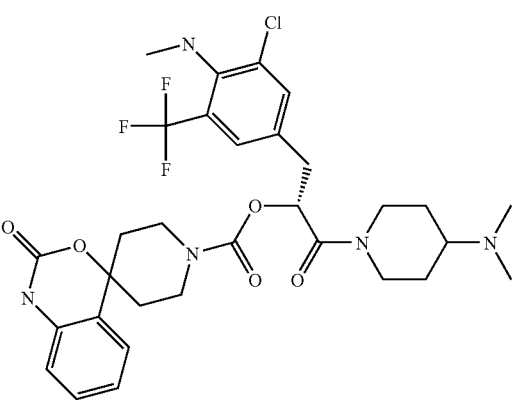
136
137

-continued
138
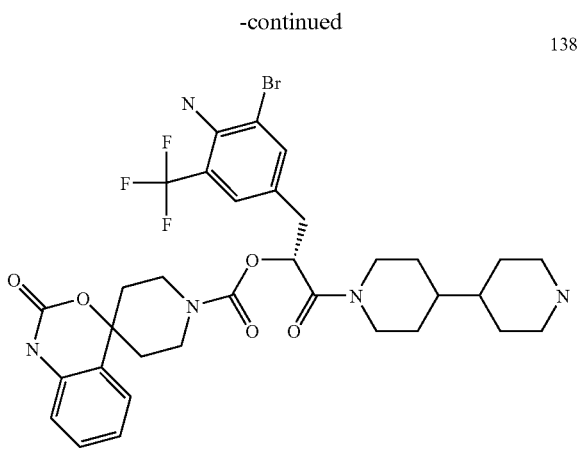
139
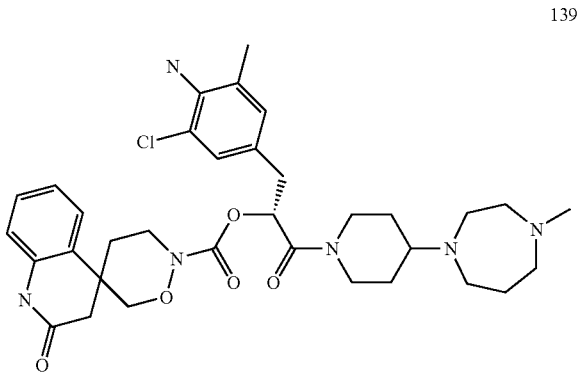
140
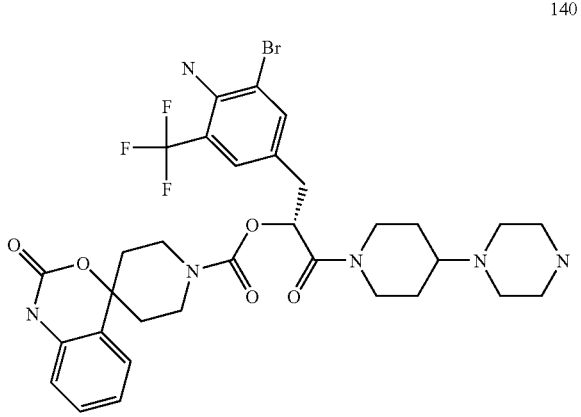
141
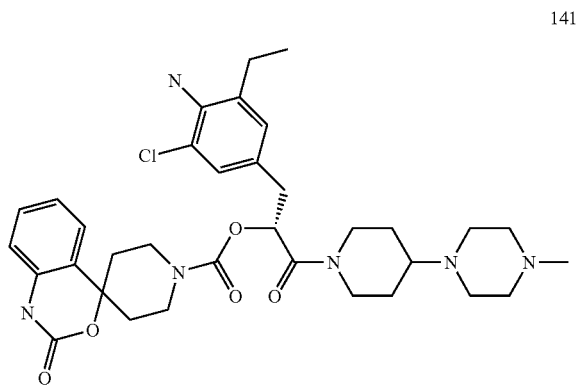
-continued
142
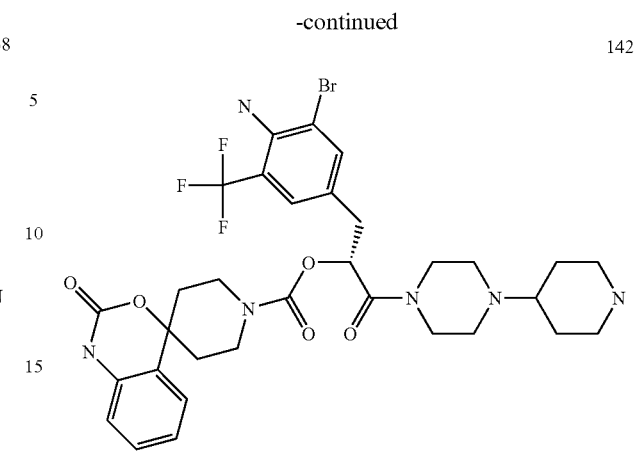
143
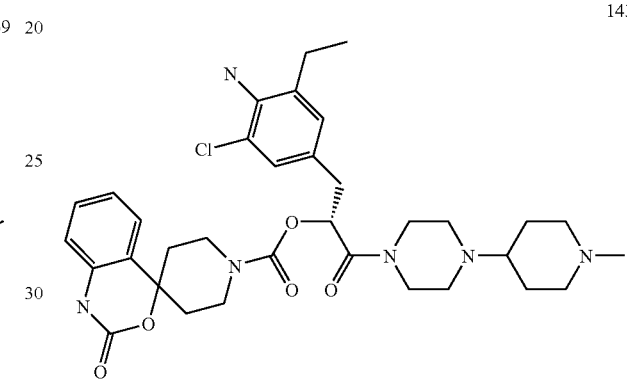
144
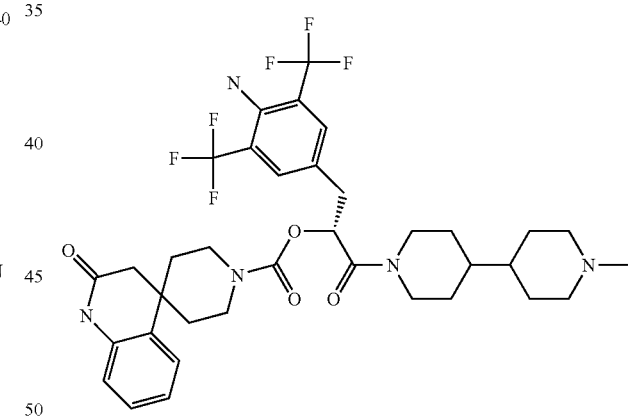
145
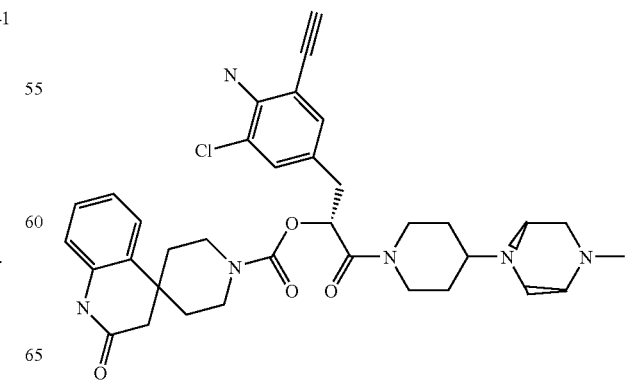

146
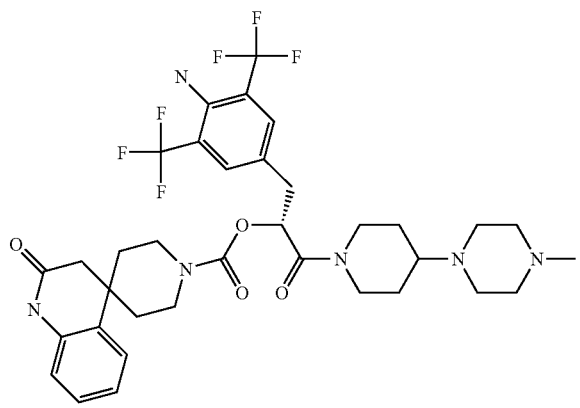
149
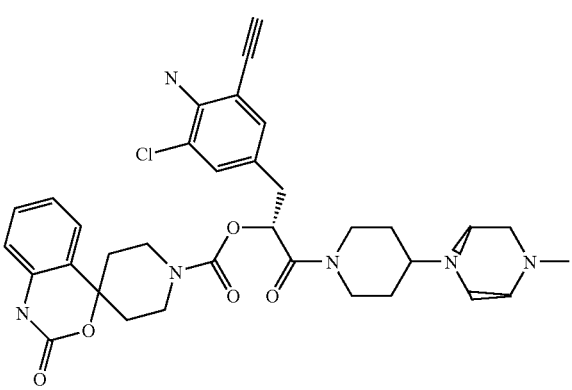
147
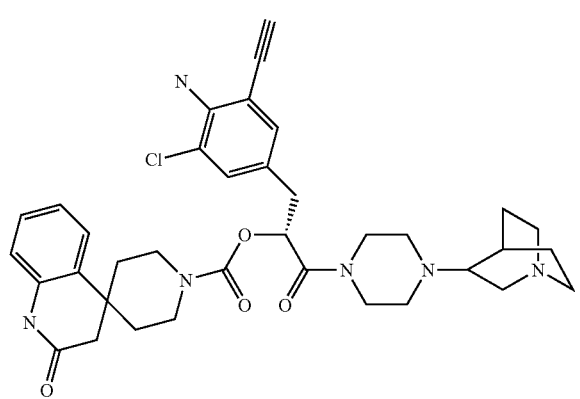
150
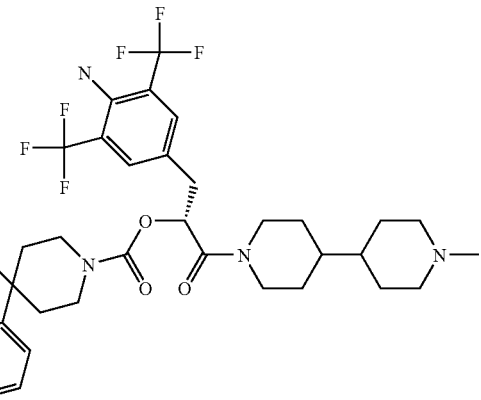
148
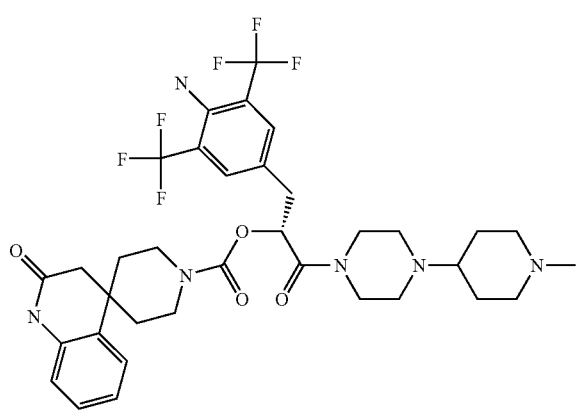
151
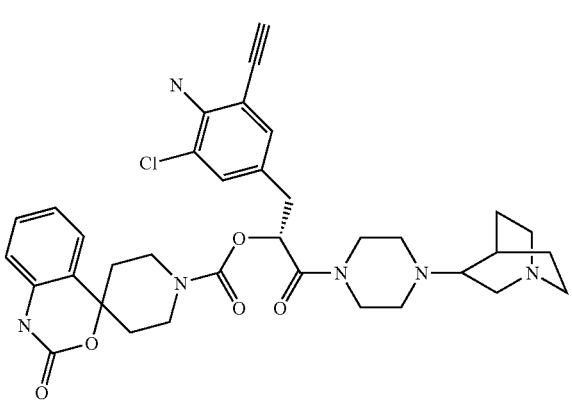

-continued
152
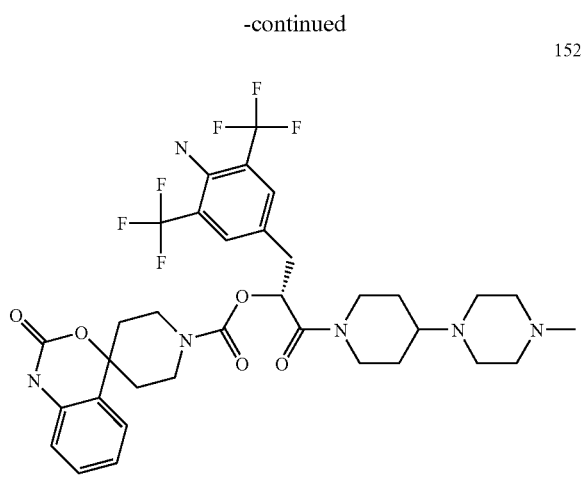
153
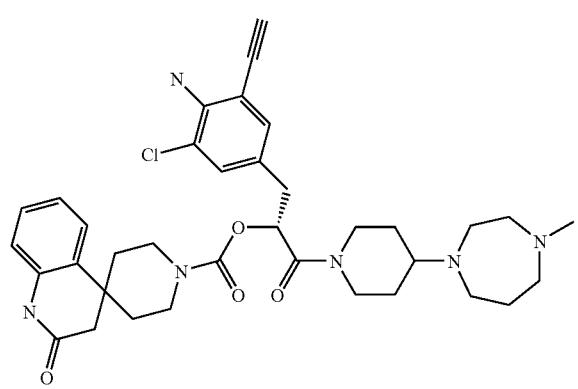
154
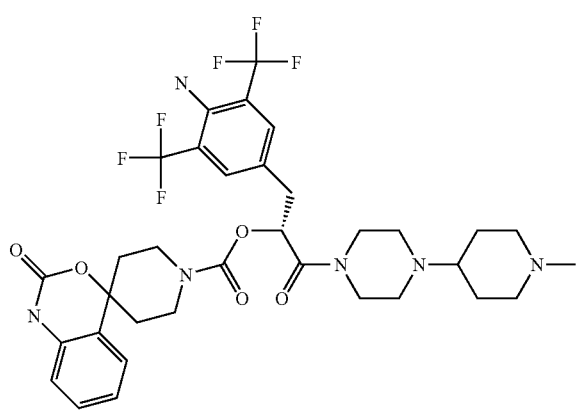
-continued
155
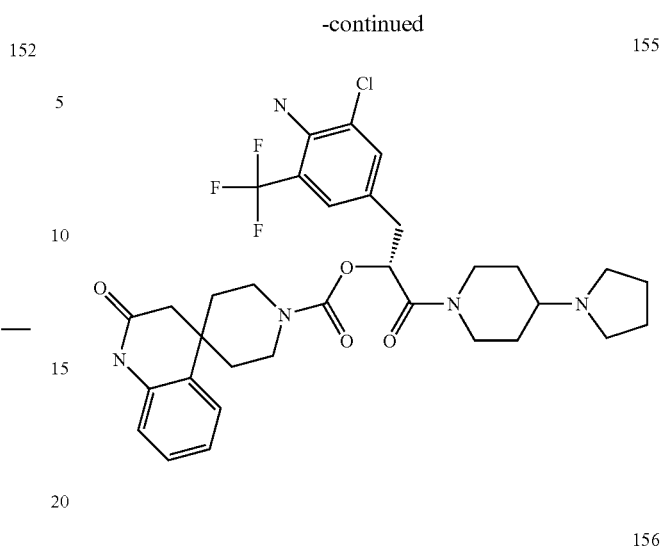
156
157
158
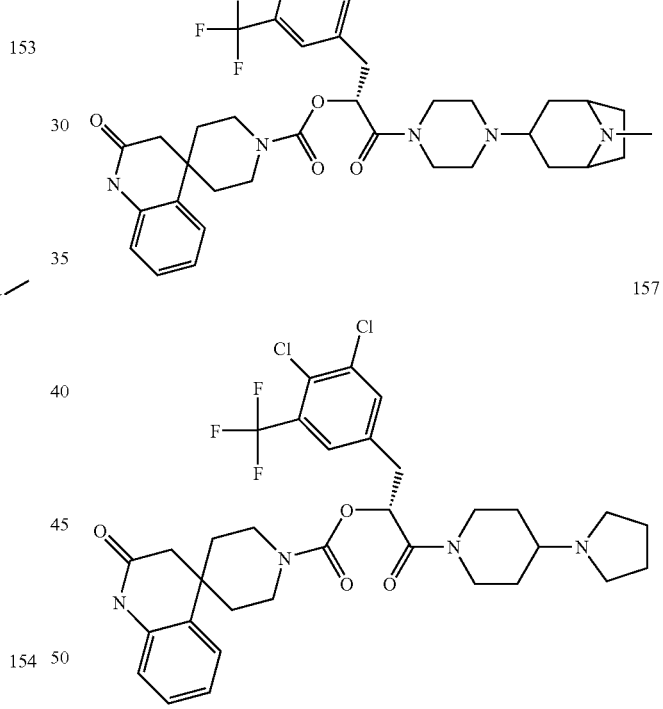
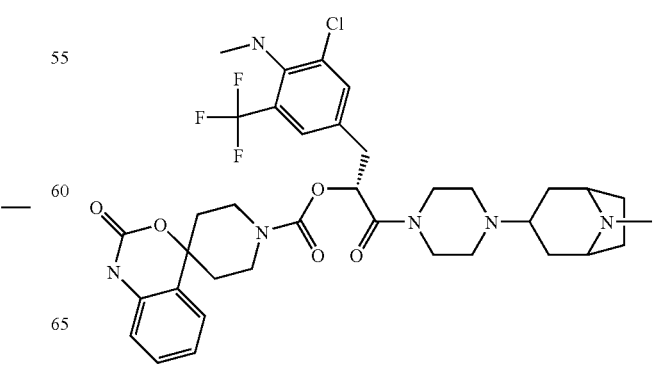

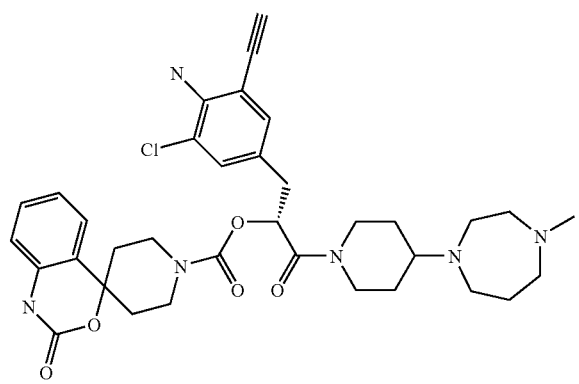
159
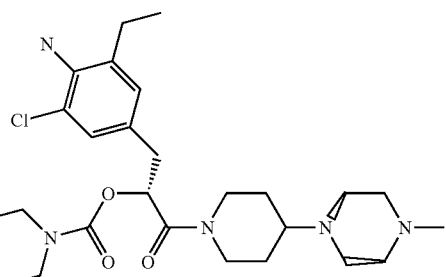
163
160
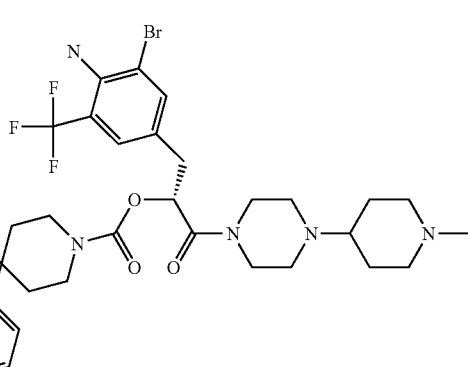
164
161
165
162
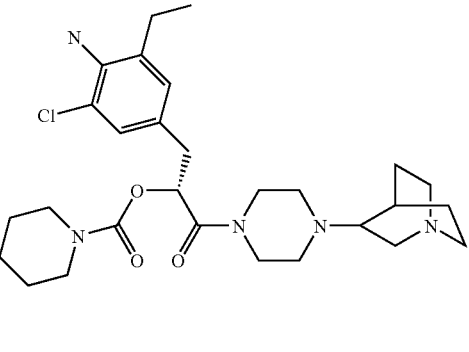
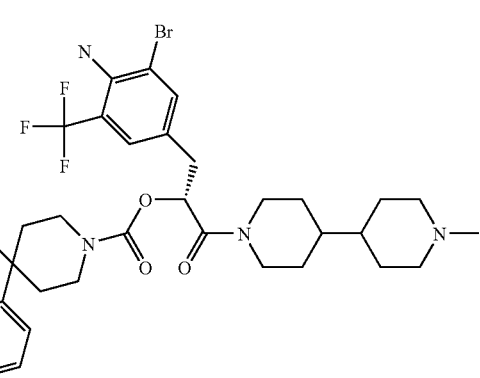
166

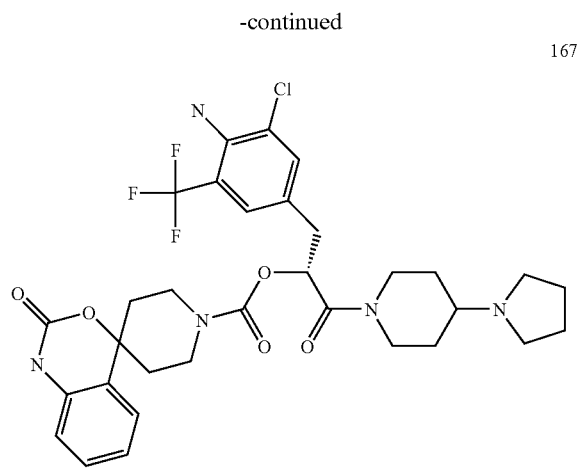
167
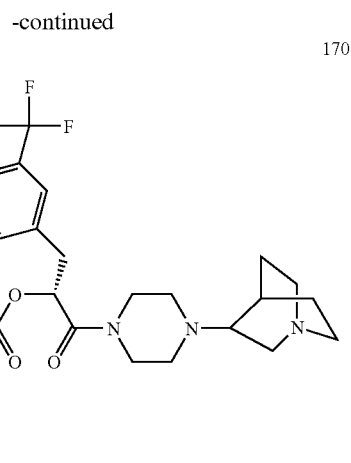
170
168
171
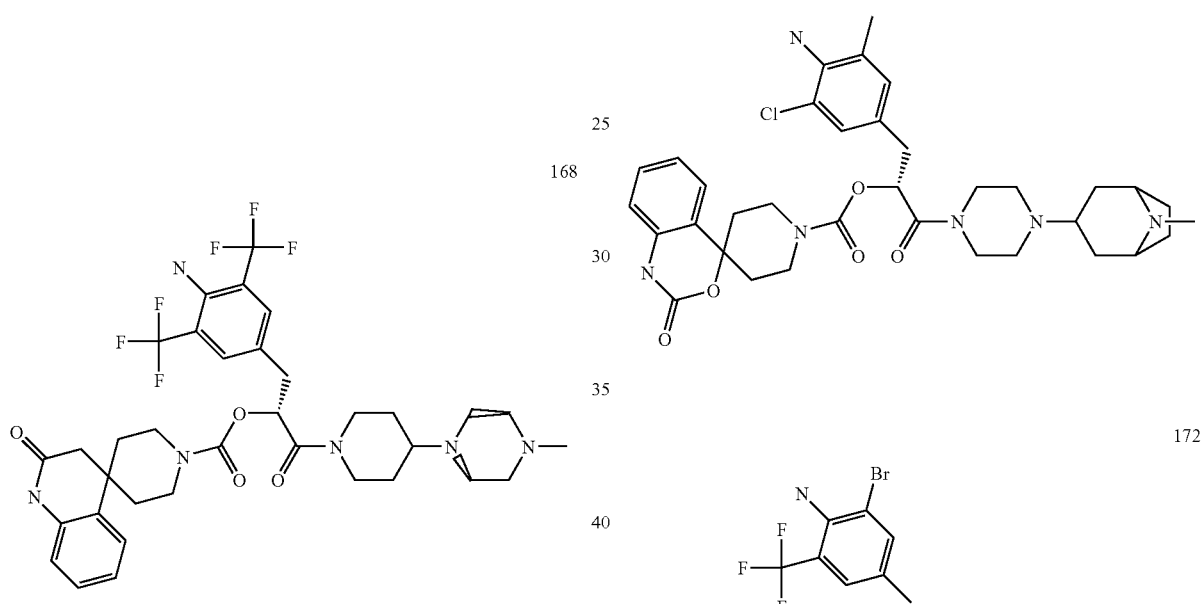
172
169
173
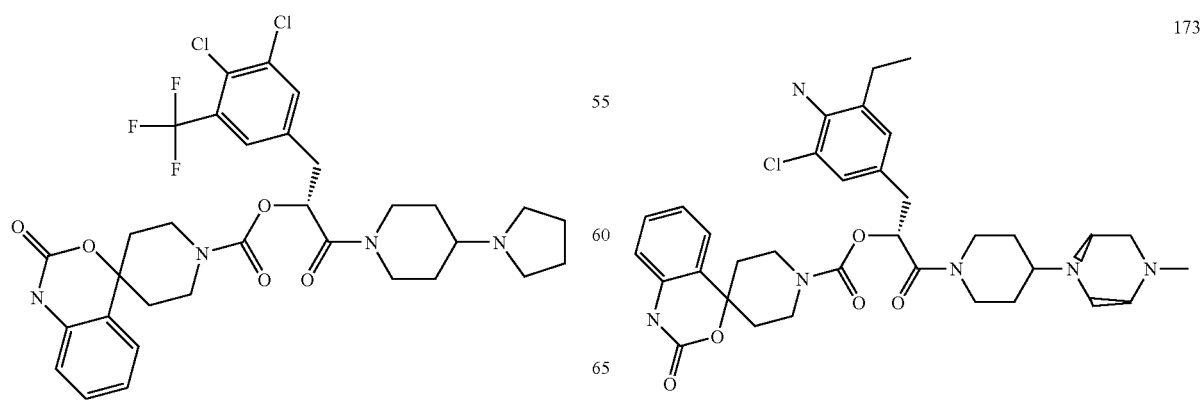

174
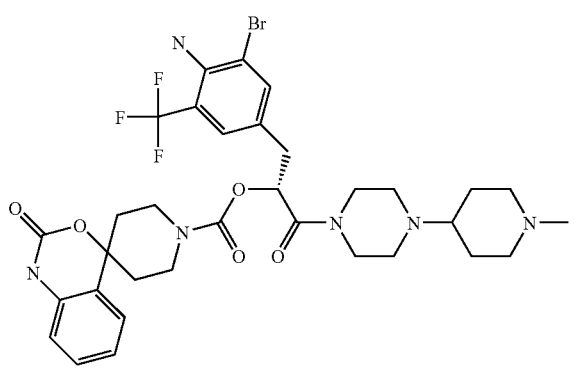
175
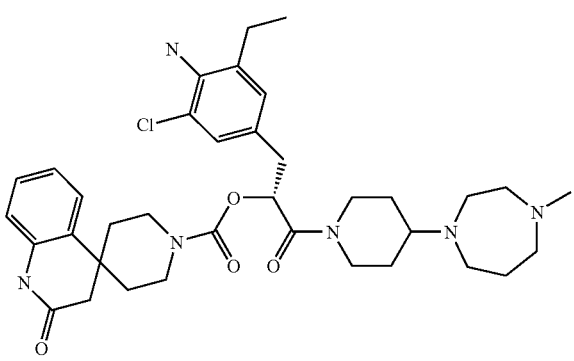
176
177
178
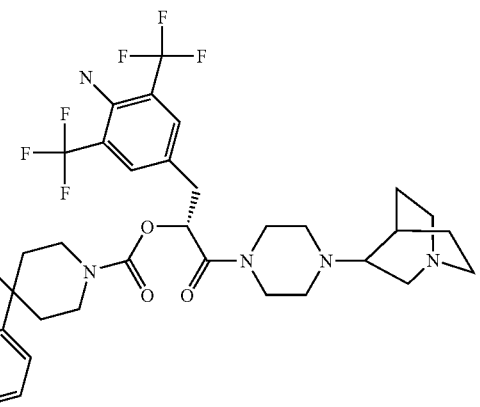
179
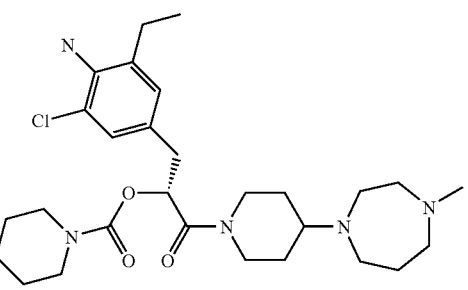
180
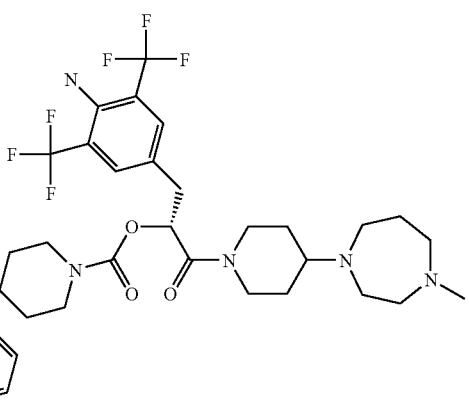

-continued
181
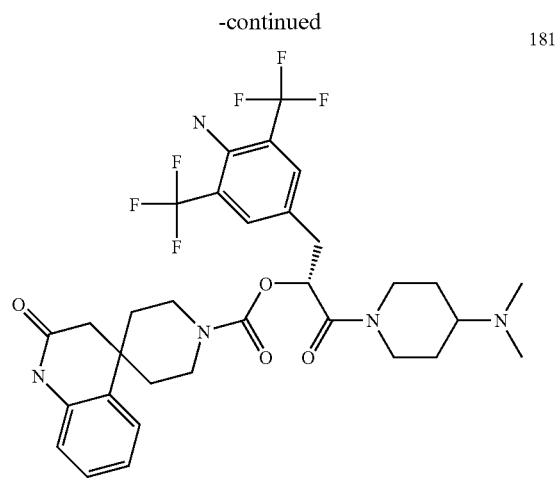
182
183
184
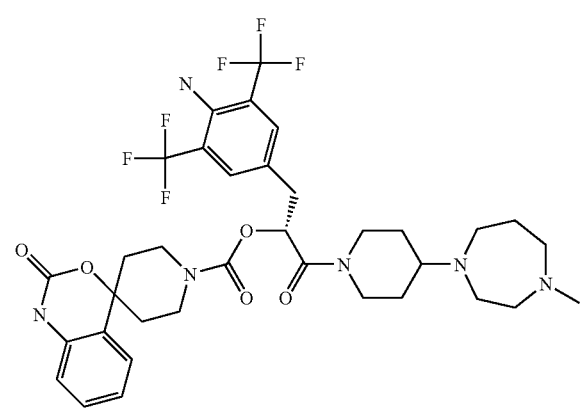
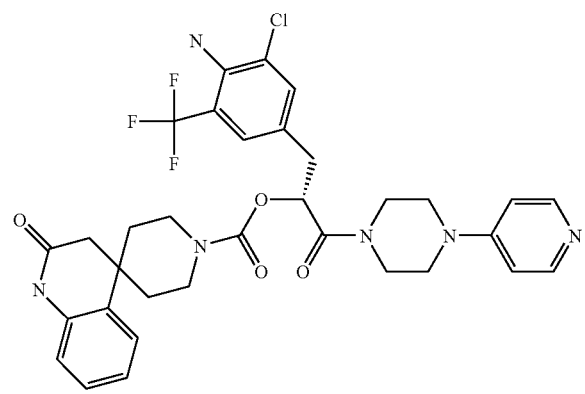
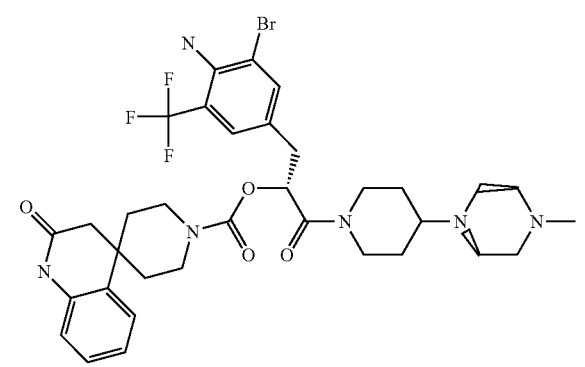
-continued
185
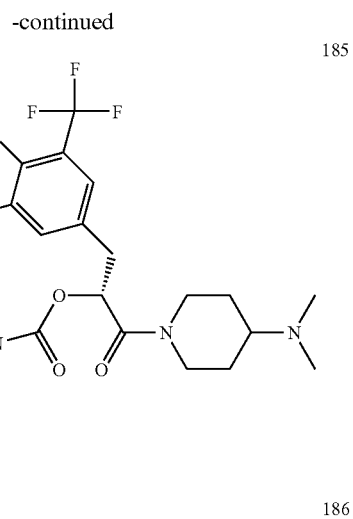
186
187
188

189
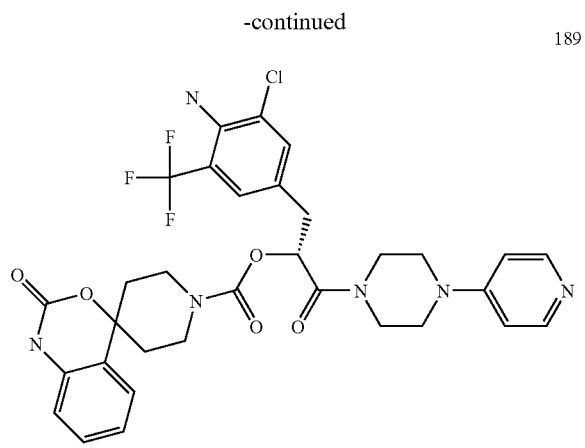
190
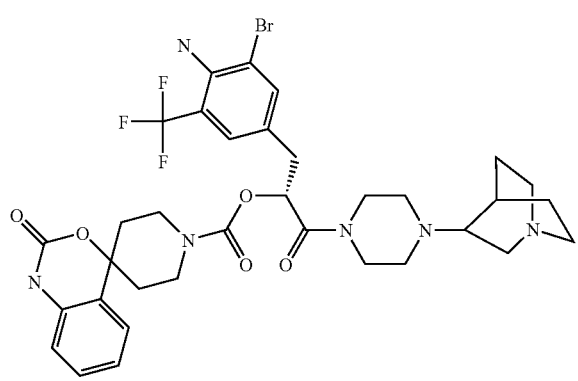
191
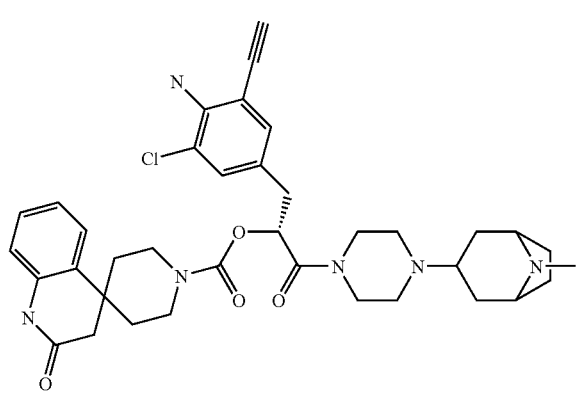
192
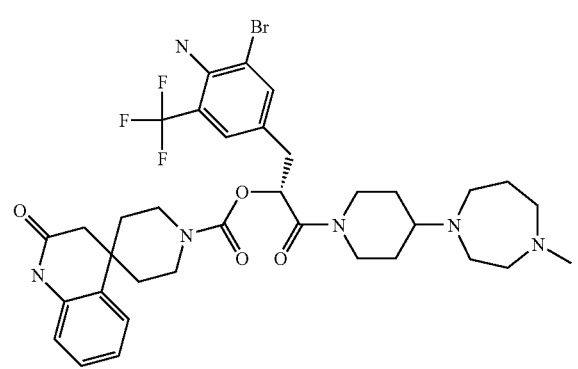
193
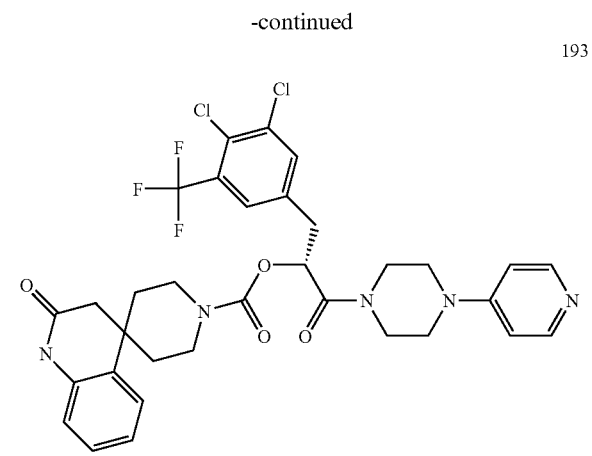
194
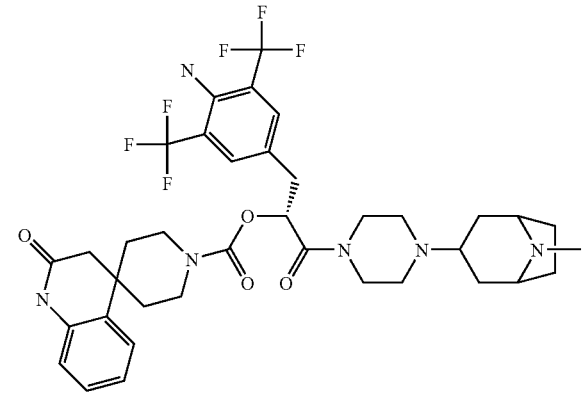
195
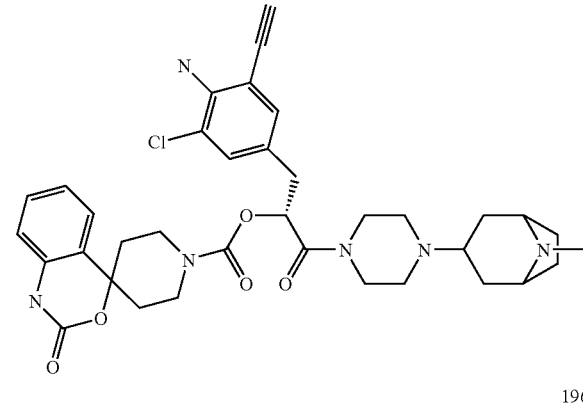
196
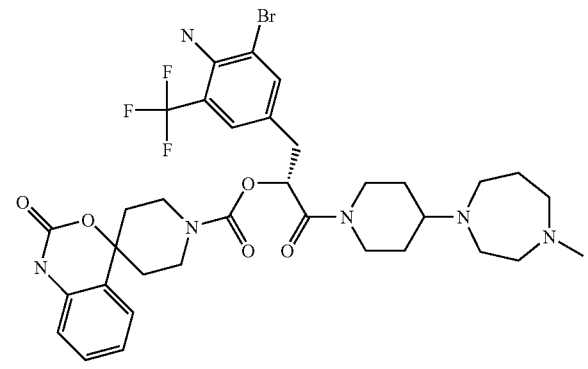

-continued
197
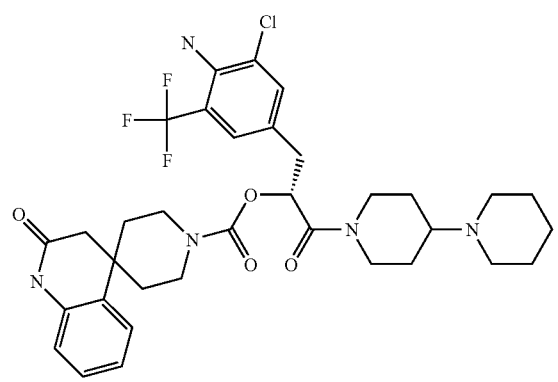
198
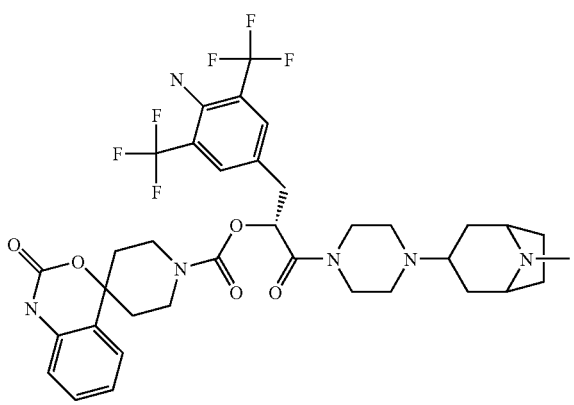
199
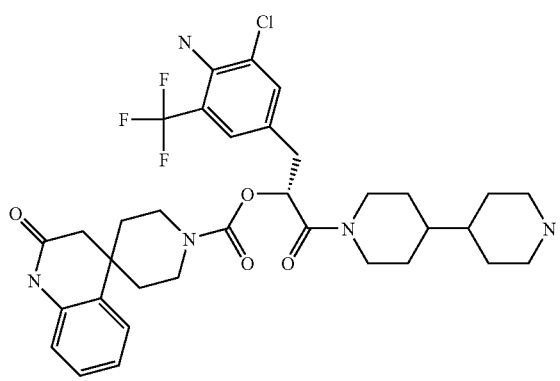
200
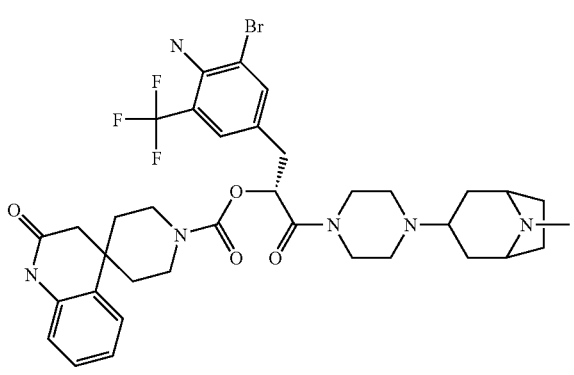
-continued
201
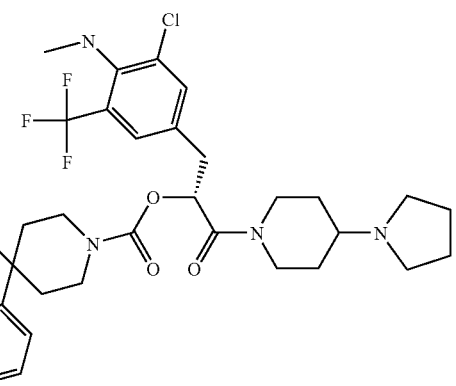
202
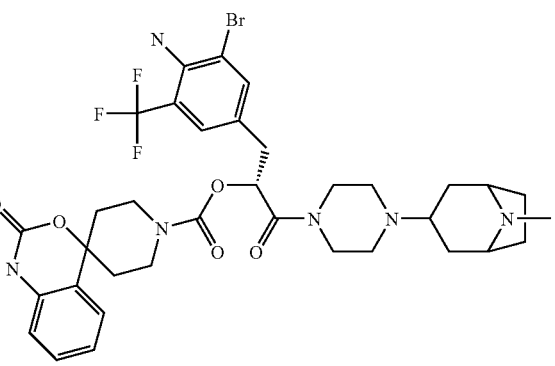
203
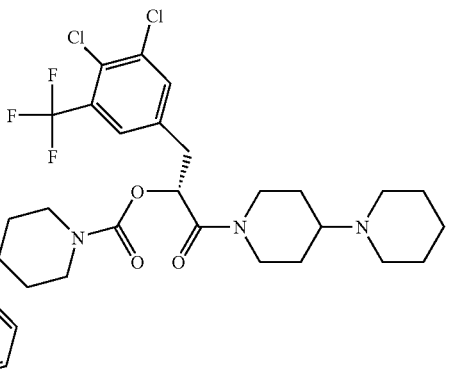
204
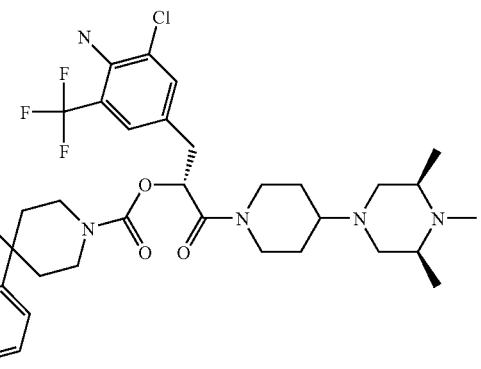

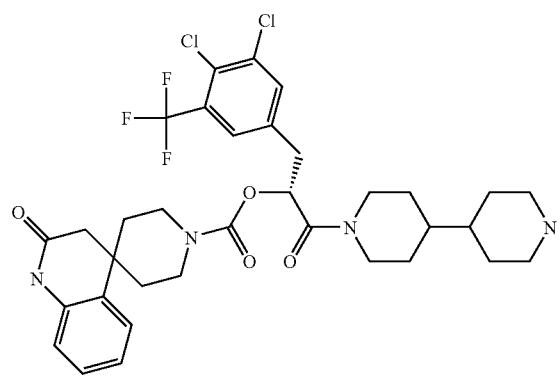
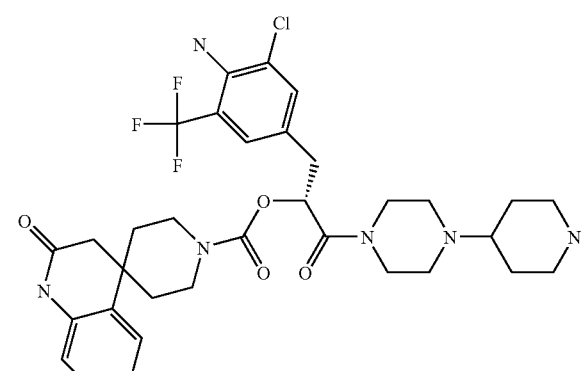
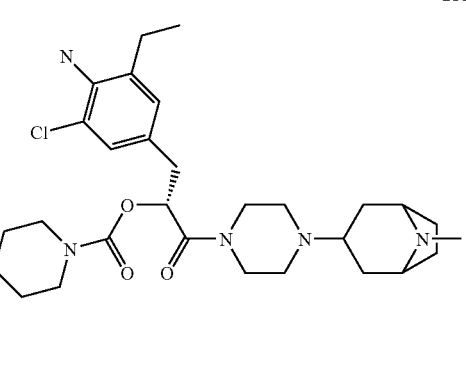

-continued
213
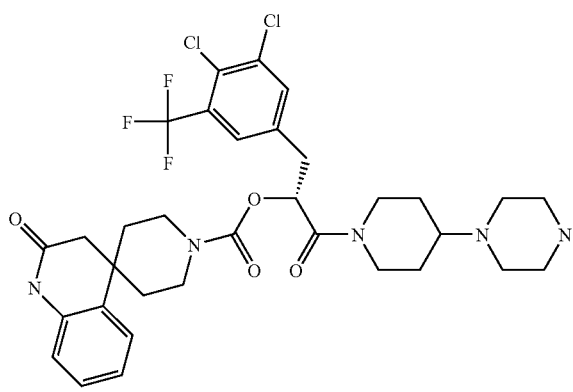
214
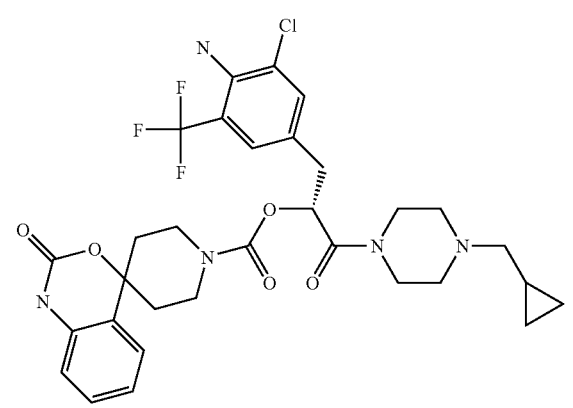
215
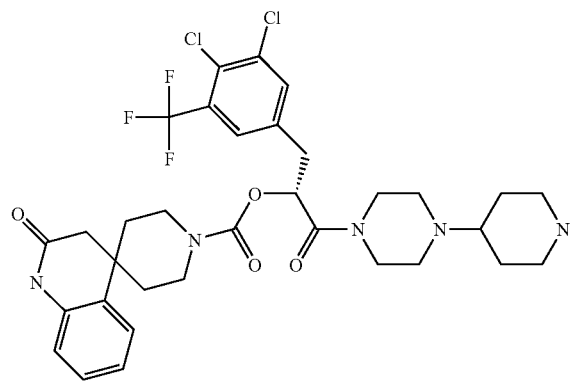
216
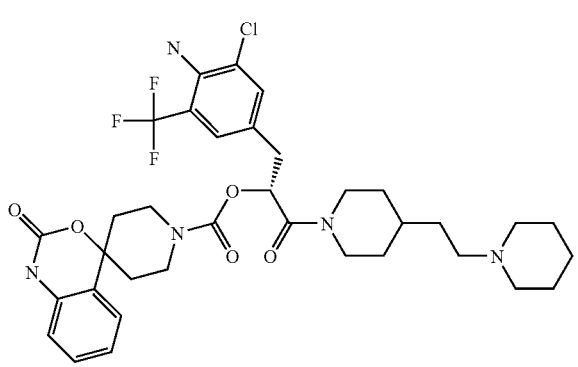
-continued
217
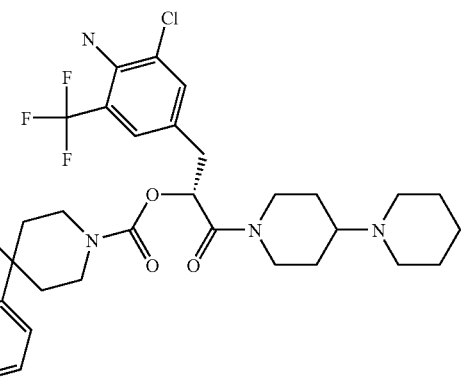
218
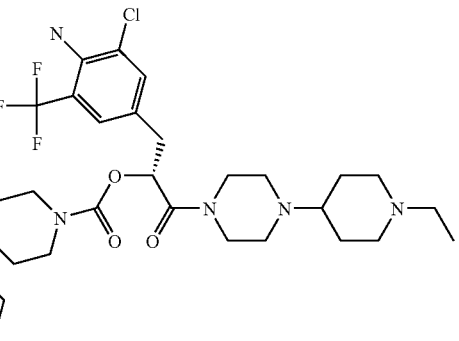
219
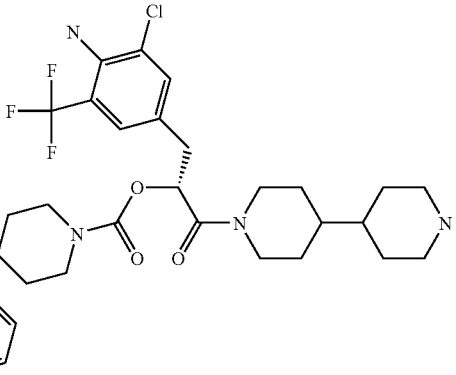
220
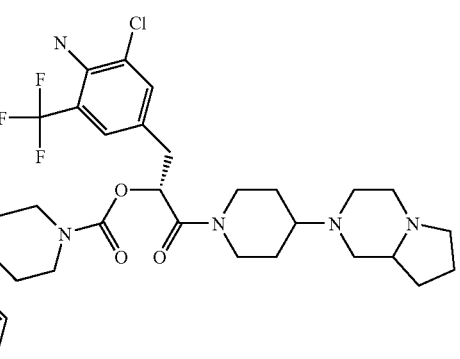

| 61 | 62 |
|---|---|
| -continued | -continued |
221
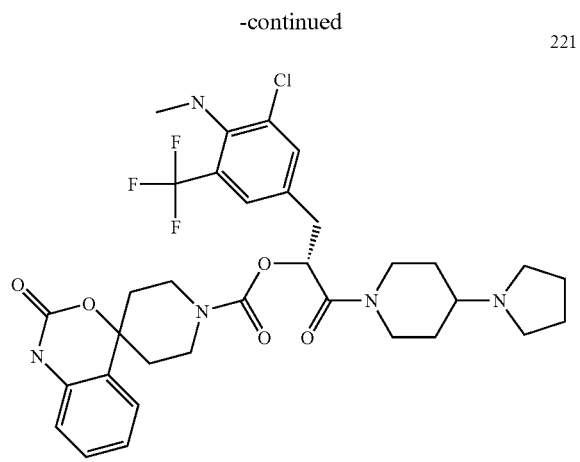
224
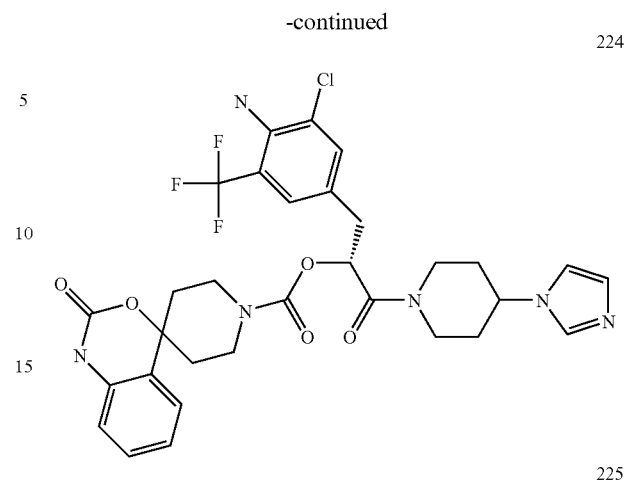
225
222
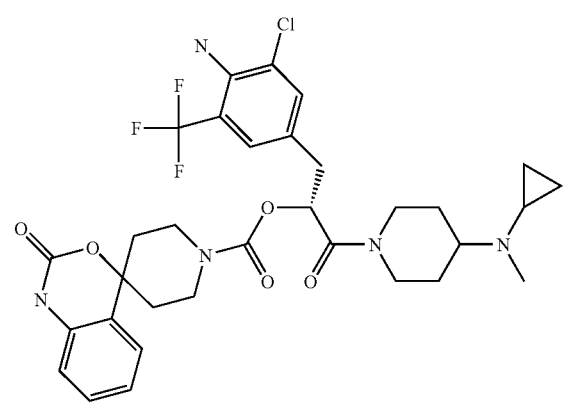
226
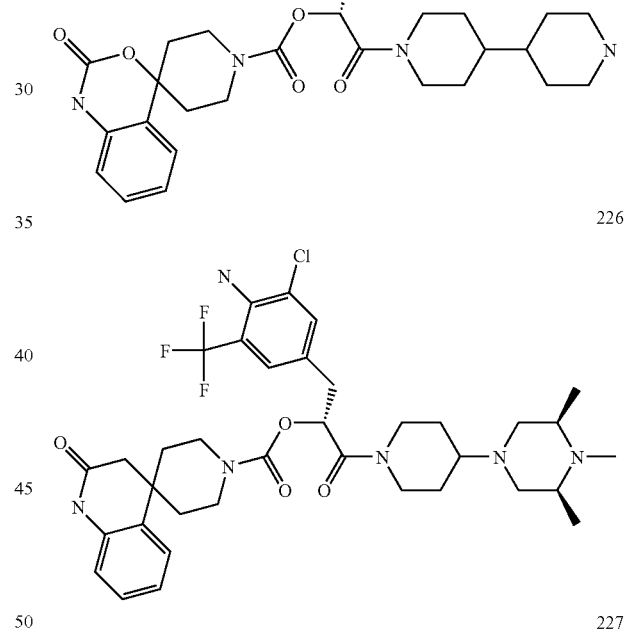
223
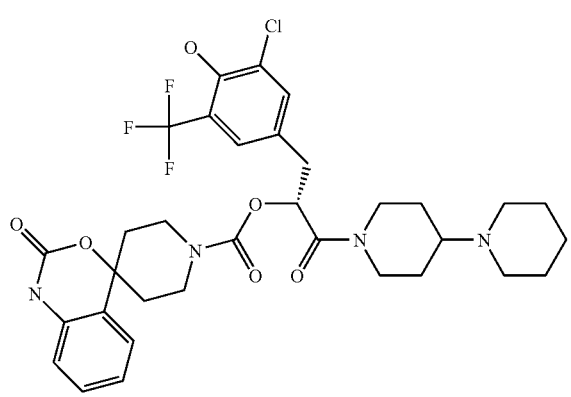
227
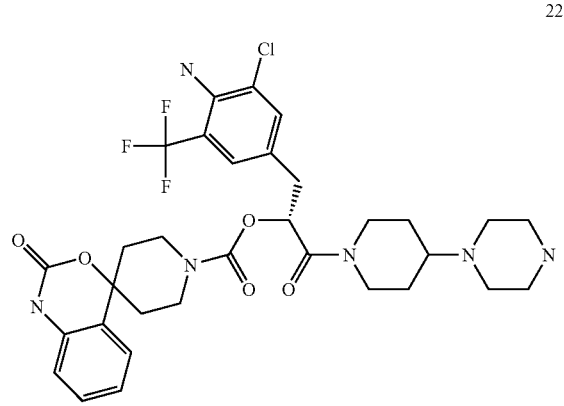

-continued

228

229

230

231

232

233

234

235

-continued
236
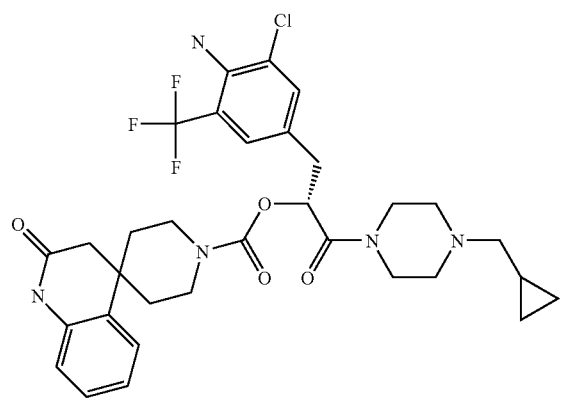
237
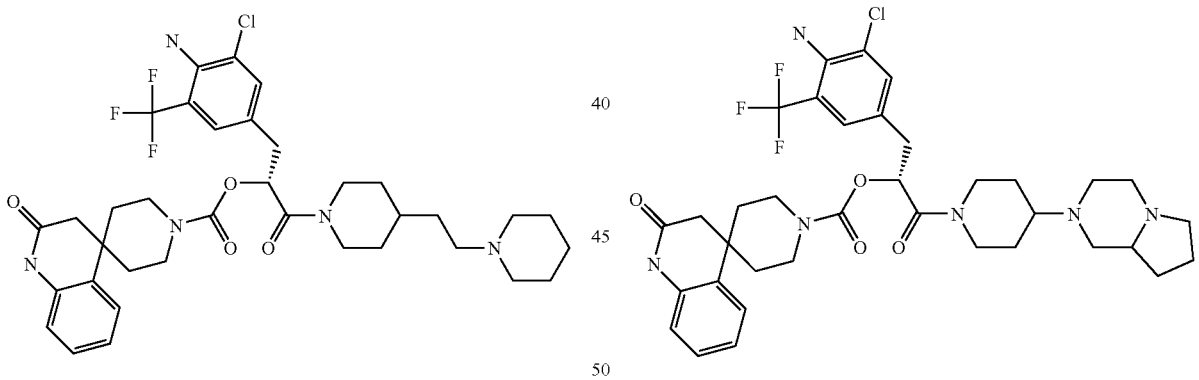
238
240
-continued
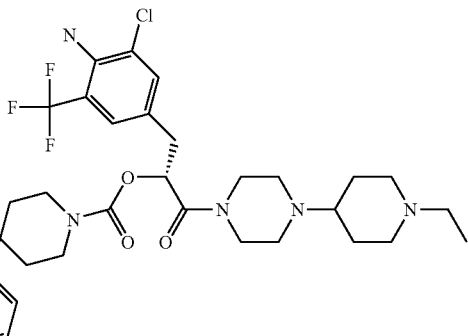
241
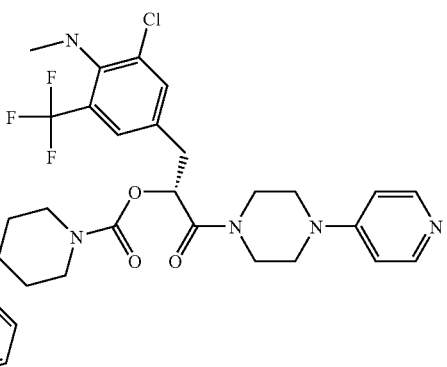
242
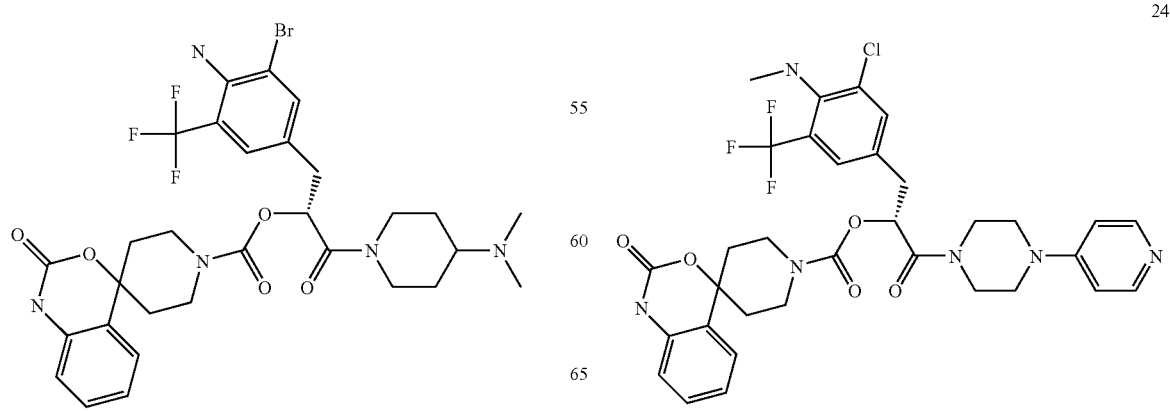
239
243

244

245

246

247

248

249

250

251

-continued

252

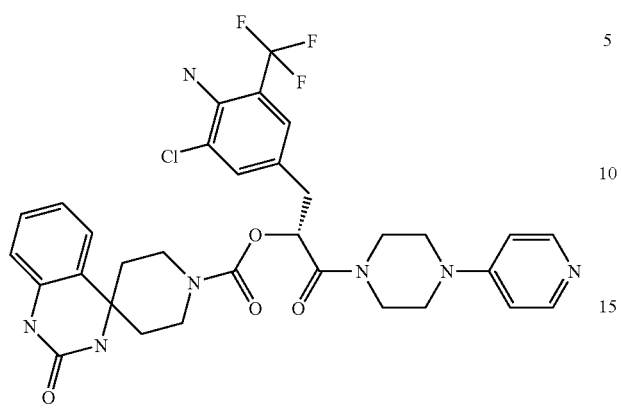

253

254

255

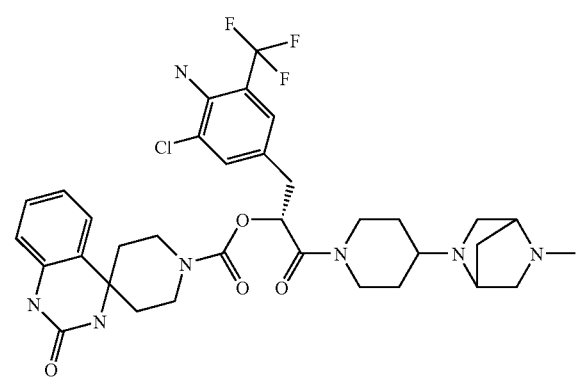

-continued

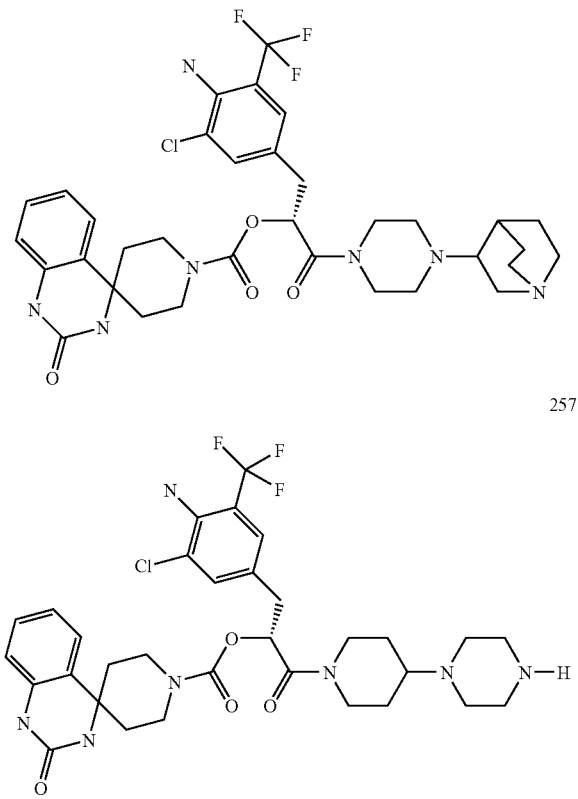

256

257

258 the tautomers, the diastereomers, the enantiomers, the hydrates thereof, the mixtures thereof and the salts thereof as well as the hydrates of the salts, while the compounds (1) (R)-1-(4-amino-3-chloro-5-trifluoromethyl-benzyl)-2-[4-(4-methyl-piperazin-1-yl)-piperidin-1-yl]-2-oxo-ethyl 1',2'-dihydro-2'-oxospiro-4H-3',1-quinazoline'-4,4'-piperidine-1-carboxylate, (2) (R)-1-(4-amino-3-chloro-5-trifluoromethyl-benzyl)-2-[4-(1-methyl-piperidin-4-yl)-piperazin-1-yl]-2-oxo-ethyl 1',2'-dihydro-2'-oxospiro-4H-3',1-quinazoline'-4,4'-piperidine-1-carboxylate, (3) (R)-1-(4-amino-3-chloro-5-trifluoromethyl-benzyl)-2-(1'-methyl-[4,4']bipiperidinyl-1-yl)-2-oxo-ethyl 1',2'-dihydro-2'-oxospiro-4H-3',1-quinazoline'-4,4'-piperidine-1-carboxylate, (4) (R)-1-(4-amino-3-chloro-5-trifluoromethyl-benzyl)-2-[1,4']bipiperidinyl-1'-yl-2-oxo-ethyl 1',2'-dihydro-2'-oxospiro-4H-3',1-quinazoline'-4,4'-piperidine-1-carboxylate, (5) (R)-1-(4-amino-3-chloro-5-trifluoromethyl-benzyl)-2-[4-(4-methyl-piperazin-1-yl)-piperidin-1-yl]-2-oxo-ethyl 1',2'-dihydro-2'-oxospiro-4H-3',1-benzoxazin-4,4'-piperidine-1-carboxylate, (6) (R)-1-(4-amino-3-chloro-5-trifluoromethyl-benzyl)-2-[4-(1-methyl-piperidin-4-yl)-piperazin-1-yl]-2-oxo-ethyl 1',2'-dihydro-2'-oxospiro-4H-3',1-benzoxazin-4,4'-piperidine-1-carboxylate, (7) (R)-1-(4-amino-3-chloro-5-trifluoromethyl-benzyl)-2-(1'-methyl-[4,4']bipiperidinyl-1-yl)-2-oxo-ethyl 1',2'-dihydro-2'-oxospiro-4H-3',1-benzoxazin-4,4'-piperidine-1-carboxylate, (8) (R)-1-(4-amino-3-chloro-5-trifluoromethyl-benzyl)-2-[1,4']bipiperidinyl-1'-yl-2-oxo-ethyl 1',2'-dihydro-2'-oxospiro-4H-3',1-benzoxazin-4,4'-piperidine-1-carboxylate, the tautomers, the diastereomers, the enantiomers, the hydrates thereof, the mixtures thereof and the salts thereof as well as the hydrates of the salts are of exceptional importance.

The compounds of general formula (I) are prepared by methods known in principle. The following methods have proved particularly useful for preparing the compounds of general formula (I) according to the invention:

(a) In order to prepare compounds of general formula

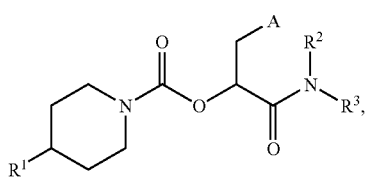
(I)

wherein A and $R^1$ to $R^3$ are as hereinbefore defined: reacting a piperidine of general formula

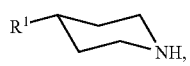
(II)

wherein $R^1$ is as hereinbefore defined,
with a carbonic acid derivative of general formula

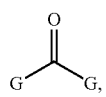
(III)

wherein G denotes a nucleofugic group which may be identical or different, preferably the chlorine atom, the p-nitrophenoxy or trichloromethoxy group, and
with a compound of general formula

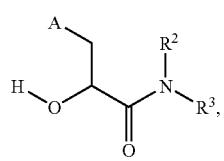
(IV)

wherein A, $R^2$ and $R^3$ are as hereinbefore defined, with the proviso that $R^2$ and $R^3$ do not contain any other free, unprotected, primary or secondary aliphatic amino function.

The reactions which are theoretically two-step reactions are usually carried out as one-pot processes, preferably by reacting one of the two components (II) or (IV) with equimolar quantities of the carbonic acid derivative of general formula (III) in a suitable solvent at lower temperature in the first stage, then adding at least equimolar amounts of the other component (II) or (IV) and finishing the reaction at elevated temperature. The reactions with bis-(trichloromethyl)-carbonate are preferably carried out in the presence of at least 2 equivalents (based on bis-(trichloromethyl)-carbonate) of a tertiary base, e.g. triethylamine, N-ethyl-diisopropylamine, pyridine, 1,5-diazabicyclo[4.3.0]non-5-ene, 1,4-diazabicyclo[2.2.2]octane or 1,8-diazabicyclo[5.4.0]undec-7-ene. Examples of solvents, which should be anhydrous, include tetrahydrofuran, dioxane, dimethyl formamide, dimethylacetamide, N-methyl-2-pyrrolidone, 1,3-dimethyl-2-imidazolidinone or acetonitrile; if bis-(trichloromethyl)-carbonate is used as the carbonyl component anhydrous chlorohydrocarbons such as dichloromethane, 1,2-dichloroethane or trichloroethylene are preferred. The reaction temperatures for the first reaction step are between –30 and +25° C., preferably –5 and +10° C., for the second reaction step they are between +15° C. and the boiling temperature of the solvent used, preferably between +20° C. and +70° C. (cf. also: H. A. Staab and W. Rohr, "Synthesen mit heterocyclischen Amiden (Azoliden)", Neuere Methoden der Präparativen Organischen Chemie, Vol. V, p. 53-93, Verlag Chemie, Weinheim/Bergstr., 1967; P. Majer and R. S. Randad, J. Org. Chem. 59, 1937-1938 (1994); K. Takeda, Y. Akagi, A. Saiki, T. Sukahara and H. Ogura, Tetrahedron Letters 24 (42), 4569-4572 (1983); S. R. Sandier and W. Karo in "Organic Functional Group Preparations", Vol. II, p. 223-245, Academis Press, New York 1971).

(b) In order to prepare compounds of general formula

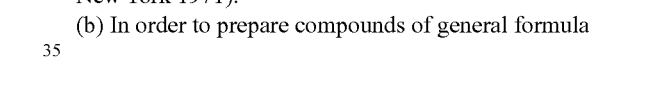
(I)

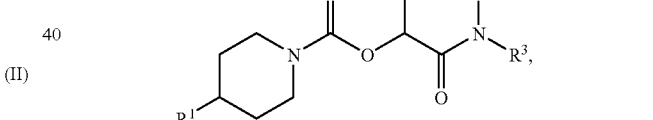

wherein A and $R^1$ to $R^3$ are as hereinbefore defined:
coupling a carboxylic acid of general formula

(V)
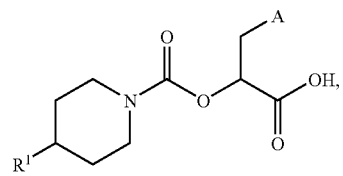

wherein A and $R^1$ are as hereinbefore defined, with an amine of general formula $HNR^2R^3$, wherein $R^2$ and $R^3$ are as hereinbefore defined, with the proviso that they do not contain any other free unprotected primary or secondary aliphatic amino function. Any primary or secondary amino function additionally present in the group —$NR^2R^3$ is in each case provided with a suitable protective group.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N', N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (Hünig base) is preferably used as an additional auxiliary base.

The so-called anhydride process is used as a further coupling method for synthesising compounds of general formula (I)(cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the mixed anhydride process is preferred (J. R. Vaughan Jr., J. Amer. Chem. Soc. 73, 3547 (1951)), in which the mixed anhydride is obtained from the carboxylic acid of general formula (V) which is to be coupled and monoisobutyl carbonate, using isobutyl chlorocarbonate in the presence of bases such as 4-methylmorpholine or 4-ethylmorpholine. The preparation of this mixed anhydride and the coupling with the amines of general formula $HNR^2R^3$ are carried out in a one-pot process, using the above-mentioned solvents and at temperatures between −20 and +25° C., preferably between 0° C. and +25° C.

(c) In order to prepare compounds of general formula

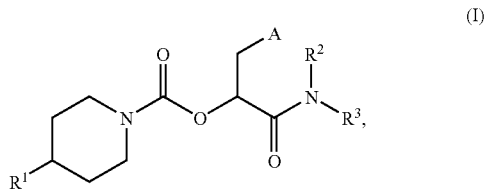

(I)

wherein A and $R^1$ to $R^3$ are as hereinbefore defined: coupling a compound of general formula

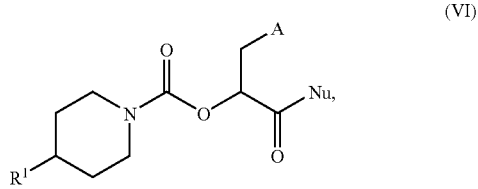

(VI)

wherein A and $R^1$ are as hereinbefore defined and Nu denotes a leaving group, for example a halogen atom, such as the chlorine, bromine or iodine atom, an alkyl-sulphonyloxy group with 1 to 10 carbon atoms in the alkyl moiety, a phenylsulphonyloxy or naphthylsulphonyloxy group optionally mono-, di- or trisubstituted by chlorine or bromine atoms, by methyl or nitro groups, while the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzo-triazol-1-yloxy or azide group, with an amine of general formula $HNR^2R^3$, wherein $R^2$ and $R^3$ are as hereinbefore defined, with the proviso that no other free, unprotected, primary or secondary aliphatic amino function is present.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2.2.2]octane or 1,8-diazabicyclo[5.4.0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as co-solvent.

The new compounds of general formula (I) according to the invention contain one or more chiral centres. If for example there are two chiral centres the compounds may occur in the form of two pairs of diastereomeric antipodes. The invention covers the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid.

According to a conventional method of separating isomers, the racemate of a compound of general formula (I) is reacted with one of the above-mentioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula (I) may also be obtained by performing the syntheses described above with a suitable reaction component in the (R) or (S) configuration.

The starting compounds of general formula (II) may be obtained, if they are not already known from the literature, according to the methods described in International Patent Application WO 03/104236. The starting compounds of general formula (III) are commercially obtainable. Compounds of general formula (IV) may be obtained by methods familiar to the peptide chemist from hydroxycarboxylic acids and amines of general formula $HNR^2R^3$.

To prepare compounds of general formula (IV), the hydroxycarboxylic acids of general formula

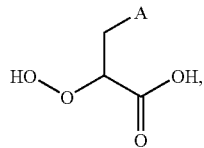

(VII)

wherein the group A is as hereinbefore defined, which are needed for the synthesis, may be obtained from compounds of general formula

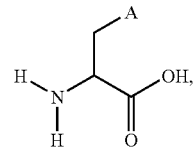

(VIII)

wherein A is as hereinbefore defined.

With the proviso that the group A does not contain an amino or methylamino group, by diazotising compounds of general formula (VII) with a suitable diazotising reagent, preferably sodium nitrite in an acid medium, it is possible to obtain the compounds of general formula (VII). If enantiomerically pure compounds are used the corresponding enantiomerically pure hydroxycarboxylic acid compounds are obtained, the configuration being retained as the reaction proceeds.

Another method of obtaining compounds of general formula (VII) wherein the groups A are as hereinbefore defined comprises alkylating the compound

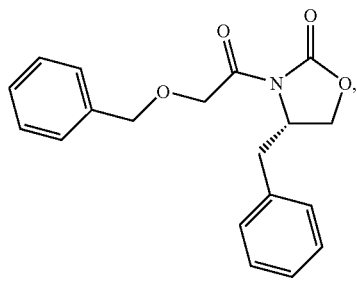

(IX)

with correspondingly substituted benzylchlorides, benzylbromides or benzyliodides of general formula

(X)

wherein A is as hereinbefore defined and X denotes a chlorine, bromine or iodine atom, analogously to methods known from the literature (Michael T. Crimmins, Kyle A. Emmitte and Jason D. Katz, Org. Lett. 2, 2165-2167 [2000]).

The diastereomeric products formed may then be separated using physico-chemical methods, preferably chromatographic methods. The hydrolytic cleaving of the chiral auxiliary, coupling with amines of general formula $HNR^2R^3$ and cleaving of the benzyl protective group also provides a way of obtaining enantiomerically pure hydroxycarboxylic acid compounds of general formula (IV).

Compounds of general formula (VII) wherein the groups A are as hereinbefore defined may also be obtained by boiling down 2-acetylamino-3-phenyl-acrylic acids of general formula

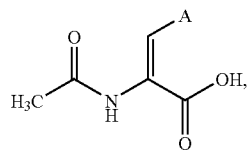

(XI)

using strong acids and subsequently reducing the 2-hydroxy-3-phenyl-acrylic acids formed.

The compounds of general formula (I) obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

The present invention relates to racemates if the compounds of general formula (I) have only one chiral element. However, the application also includes the individual diastereomeric pairs of antipodes or mixtures thereof which are obtained if there is more than one chiral element in the compounds of general formula (I), as well as the individual optically active enantiomers of which the above-mentioned racemates are made up.

Also included in the subject matter of this invention are the compounds according to the invention, including the salts thereof, in which one or more hydrogen atoms, for example one, two, three, four or five hydrogen atoms, are replaced by deuterium.

The new compounds of general formula (I) and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 µl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 µl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 µM human CGRP-alpha during incubation.

The concentration binding curves are analysed using computer-aided non-linear curve matching.

The compounds mentioned hereinbefore show IC$_{50}$ values ≤10000 nM in the test described.

B. CGRP Antagonism in SK-N-MC Cells

SK-N-MC cells (1 million cells) are washed twice with 250 µl incubation buffer (Hanks' HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations ($10^{-11}$ to $10^{-6}$ M), or additionally the substance in 3 to 4 different concentrations, the mixture is incubated for another 15 minutes.

Intracellular cAMP is then extracted by the addition of 20 µl of 1 M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the pA$_2$ values of antagonistically acting substances are determined graphically.

The compounds of general formula (I) exhibit CGRP-antagonistic properties in the in vitro test model described, in a dosage range between $10^{-12}$ and $10^{-5}$ M.

In view of their pharmacological properties the compounds of general formula (I) and the salts thereof with physiologically acceptable acids are thus suitable for the acute and prophylactic treatment of headaches, particularly migraine or cluster headaches. Moreover, the compounds of general formula (I) also have a positive effect on the following diseases: non-insulin-dependent diabetes mellitus ("NIDDM"), complex regional pain syndrome (CRPS1), cardiovascular diseases, morphine tolerance, diarrhea caused by clostridium toxin, skin diseases, particularly thermal and radiation-induced skin damage including sunburn, inflammatory diseases, e.g. inflammatory diseases of the joints (arthritis), neurogenic inflammation of the oral mucosa, inflammatory lung diseases, allergic rhinitis, asthma, diseases accompanied by excessive vasodilatation and resultant reduced blood supply to the tissues, e.g. shock and sepsis. In addition, the compounds according to the invention have a general pain-relieving effect.

The symptoms of menopausal hot flushes caused by vasodilatation and increased blood flow in oestrogen-deficient women and hormone-treated patients with prostate carcinoma are favourably affected by the CGRP-antagonists of the present application in a preventive and acute-therapeutic capacity, this therapeutic approach being distinguished from hormone replacement by the absence of side effects.

The dosage required to achieve a corresponding effect is conveniently 0.01 to 3 mg/kg of body weight, preferably 0.01 to 1 mg/kg of body weight, when administered intravenously or subcutaneously and 0.01 to 20 mg/kg of body weight, preferably 0.1 to 10 mg/kg of body weight when administered orally, and 0.01 to 10 mg/kg of body weight, preferably 0.1 to 10 mg/kg of body weight when administered nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from 1/5 of the lower limits mentioned above up to 1/1 of the upper limits specified.

The compounds prepared according to the invention may be administered either on their own or optionally in combination with other active substances for the treatment of migraine by intravenous, subcutaneous, intramuscular, intrarectal, intranasal route, by inhalation, transdermally or orally, while aerosol formulations are particularly suitable for inhalation. The combinations may be administered either simultaneously or sequentially.

Categories of active substance which may be used in the combination include e.g. angiotensin II receptor antagonists, α-agonists and α-antagonists, 5-HT$_{1B/1D}$ agonists, AMPA antagonists, mild analgesics, antidepressants, antiemetics, anticonvulsants, antimuscarinics, β-blockers, calcium antagonists, corticosteroids, ergot alkaloids, histamine-H1 receptor antagonists, neurokinine antagonists, neuroleptics, non-steroidal antiinflammatories, NO-synthase inhibitors, prokinetics, selective serotonin reuptake inhibitors or other anti-migraine agents, which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, tenoxicam, zomepirac or the pharmaceutically acceptable salts thereof as well as meloxicam and other selective COX2-inhibitors, such as for example rofecoxib and celecoxib.

It is also possible to use candesartan, eprosartan, irbesartan, losartan, olmesartan, tasosartan, telmisartan, valsartan, duloxetine, ergotamine, dihydro-ergotamine, metoclopramide, domperidone, diphenhydramine, cyclizine, promethazine, chlorpromazine, vigabatrin, timolol, isometheptene, pizotifen, botox, gabapentin, topiramate, riboflavin, montelukast, lisinopril, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, lidocaine or diltiazem and other 5-HT$_{1B/1D}$-agonists such as, for example, almotriptan, avitriptan, donitriptan, eletriptan, frovatriptan, naratriptan, rizatriptan, sumatriptan and zolmitriptan and the physiologically acceptable salts thereof.

The dosage of these active substances is expediently 1/5 of the lowest recommended dose to 1/1 of the normally recommended dose, i.e. for example 20 to 100 mg of sumatriptan.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Experimental Section

As a rule, IR, $^1$H-NMR and/or mass spectra have been obtained for the compounds prepared.

Unless otherwise stated, R$_f$ values are obtained using ready-made silica gel TLC plates 60 F254 (E. Merck, Darmstadt, Item no. 1.05714) without chamber saturation.

The ratios given for the eluants relate to units by volume of the solvent in question. The units by volume specified for NH$_3$ refer to a concentrated solution of NH$_3$ in water.

Unless otherwise stated, the acid, base and salt solutions used for working up the reaction solutions are aqueous systems of the concentrations specified.

For chromatographic purification, silica gel made by Millipore (MATREX™, 35-70 μm) is used.

If there are no details of the configuration, it is unclear whether the substances are pure enantiomers or whether partial or even total racemisation has taken place.

The following abbreviations are used in the experimental descriptions:
Cyc cyclohexane
DCM dichloromethane
DMAP 4-dimethylaminopyridine
DMF N,N-dimethylformamide
EtOAc ethyl acetate
HCl hydrochloric acid
Hünig base ethyldiisopropylamine
LiOH lithium hydroxide
MeOH methanol
RT ambient temperature
TBME tert.-butyl-methylether
TBTU 2-(1H-benzotriazol-1-yl)-1,1,3,3-tetramethyluronium-tetrafluoroborate
THF tetrahydrofuran

EXAMPLE 1

(R)-1-(4-amino-3-chloro-5-trifluoromethyl-benzyl)-2-[4-(4-methyl-piperazin-1'-yl)-piperidin-1-yl]-2-oxo-ethyl 1',2'-dihydro-2'-oxospiro-4H-3',1-quinazoline'-4,4'-piperidine-1-carboxylate

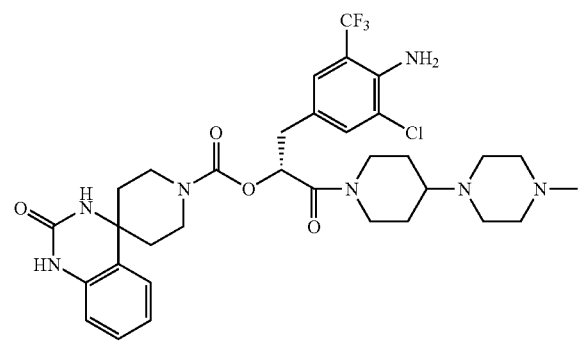

(1a) (R)-2-(4-amino-3-chloro-5-trifluoromethyl-phenyl)-1-methoxycarbonyl-ethyl 1',2'-dihydro-2'-oxospiro-4H-3',1-quinazoline'-4,4'-piperidine-1-carboxylate A mixture of 0.62 g (5.07 mmol) DMAP, 1.02 g (5.06 mmol) 4-nitrophenyl chloroformate and 20 mL pyridine was stirred for 40 min at RT, 1.50 g (5.04 mmol) methyl(R)-3-(4-amino-3-chloro-5-trifluoromethyl-phenyl)-2-hydroxy-propionate, dissolved in 20 mL pyridine, was added dropwise thereto and the mixture was stirred for 2 h at RT. After the addition of 1.2 g (5.52 mmol) 2',3'-dihydro-2'-oxospiro-piperidin-4,4'(1'H)-quinazoline the mixture was stirred overnight at RT, combined with 60 mL TBME, washed three times with 1 M KHSO$_4$ solution and six times with 15% K$_2$CO$_3$ solution. The organic phase was dried over MgSO$_4$, filtered and evaporated down under reduced pressure. The residue was purified by column chromatography over silica gel.

| | |
|---|---|
| Yield: | 1.20 g (44% of theory) |
| MS: | (M + H)$^+$ = 541/543 (Cl) |
| R$_f$ = | 0.61 (silica gel, DCM/Cyc/MeOH/NH$_3$ 70:15:15:2) |

(1b) (R)-2-(4-amino-3-chloro-5-trifluoromethyl-phenyl)-1-carboxy-ethyl 1',2'-dihydro-2'-oxospiro-4H-3',1-quinazoline'-4,4'-piperidine-1-carboxylate A mixture of 1.20 g (2.22 mmol)(R)-2-(4-amino-3-chloro-5-trifluoromethyl-phenyl)-1-methoxycarbonyl-ethyl 1',2'-dihydro-2'-oxospiro-4H-3',1-quinazoline'-4,4'-piperidine-1-carboxylate and 50 ml THF was combined with an aqueous solution of 100 mg (4.09 mmol) LiOH and stirred for 4 hours at RT. The reaction mixture was evaporated down under reduced pressure, combined with water and the aqueous phase was extracted twice with EtOAc. Then the aqueous phase was acidified by the addition of 1 molar hydrochloric acid and exhaustively extracted with DCM. The combined organic phases were dried over sodium sulphate and evaporated down under reduced pressure.

| | |
|---|---|
| Yield: | 0.90 g (77% of theory) |
| MS: | $(M + H)^+ = 525/527$ (Cl) |
| $R_f =$ | 0.17 (silica gel, DCM/Cyc/MeOH/NH$_3$ 70:15:15:2) |

(1c) (R)-1-(4-amino-3-chloro-5-trifluoromethyl-benzyl)-2-[4-(4-methyl-piperazin-1-yl)-piperidin-1-yl]-2-oxo-ethyl 1',2'-dihydro-2'oxospiro-4H-3',1-quinazoline'-4,4'-piperidine-1-carboxylate 80 mg (0.24 mmol) TBTU and 0.05 mL (0.28 mmol) Hünig base were added to a solution of 100 mg (0.19 mmol)(R)-2-(4-amino-3-chloro-5-trifluoromethyl-phenyl)-1-carboxy-ethyl 1',2'-dihydro-2'-oxospiro-4H-3',1-quinazoline'-4,4'-piperidine-1-carboxylate in 15 mL THF and stirred for 30 min at RT. Then the mixture was combined with 40 mg (0.21 mmol) 1-methyl-4-piperidin-4-yl-piperazine dissolved in 5 mL THF and the reaction mixture was stirred for 4 h at RT. After the addition of 30 mL EtOAc the reaction mixture was washed twice with 20 mL 15% K$_2$CO$_3$ solution. The organic phase was dried over MgSO$_4$, filtered and evaporated down under reduced pressure. The residue was purified by column chromatography (silica gel, gradient DCM to DCM/MeOH/NH$_3$ 50:45:5).

| | |
|---|---|
| Yield: | 40 mg (31% of theory) |
| MS: | $(M + H)^+ = 692/694$ (Cl) |
| $R_f =$ | 0.36 (silica gel, DCM/Cyc/MeOH/NH$_3$ 70:15:15:2) |

EXAMPLE 2

(R)-1-(4-amino-3-chloro-5-trifluoromethyl-benzyl)-2-[4-(1-methyl-piperidin-4-yl)-piperazin-1-yl]-2-oxo-ethyl 1',2'-dihydro-2'-oxospiro-4H-3',1-quinazoline'-4,4'-piperidine-1-carboxylate

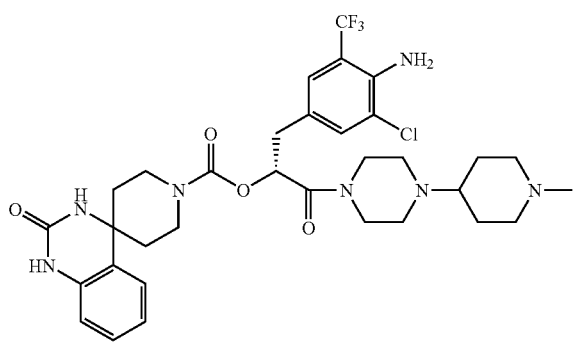

Analogously to Example (1c) the product was obtained from 100 mg (0.19 mmol)(R)-2-(4-amino-3-chloro-5-trifluoromethyl-phenyl)-1-carboxy-ethyl 1',2'-dihydro-2'-oxospiro-4H-3',1-quinazoline'-4,4'-piperidine-1-carboxylate and 40 mg (0.22 mmol) 1-(1-methyl-piperidin-4-yl)-piperazine.

| | |
|---|---|
| Yield: | 20 mg (15% of theory) |
| MS: | $(M + H)^+ = 692/694$ (Cl) |
| $R_f =$ | 0.30 (silica gel, DCM/Cyc/MeOH/NH$_3$ 70:15:15:2) |

EXAMPLE 3

(R)-1-(4-amino-3-chloro-5-trifluoromethyl-benzyl)-2-(1'-methyl-[4,4']bipiperidinyl-1-yl)-2-oxo-ethyl 1',2'-dihydro-2'-oxospiro-4H-3',1-quinazoline'-4,4'-piperidine-1-carboxylate

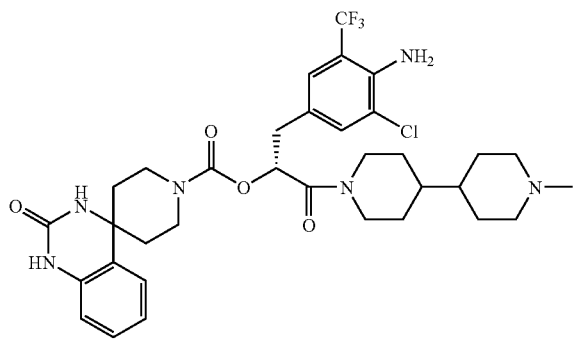

Analogously to Example (1c) the product was obtained from 100 mg (0.19 mmol)(R)-2-(4-amino-3-chloro-5-trifluoromethyl-phenyl)-1-carboxy-ethyl 1',2'-dihydro-2'-oxospiro-4H-3',1-quinazoline'-4,4'-piperidine-1-carboxylate and 40 mg (0.22 mmol) 1-methyl-[4,4']bipiperidinyl.

| | |
|---|---|
| Yield: | 10 mg (8% of theory) |
| MS: | $(M + H)^+ = 691/693$ (Cl) |
| $R_f =$ | 0.37 (silica gel, DCM/Cyc/MeOH/NH$_3$ 70:15:15:2) |

EXAMPLE 4

(R)-1-(4-amino-3-chloro-5-trifluoromethyl-benzyl)-2-[1,4']bipiperidinyl-1'-yl-2-oxo-ethyl 1',2'-dihydro-2'-oxospiro-4H-3',1-quinazoline'-4,4'-piperidine-1-carboxylate

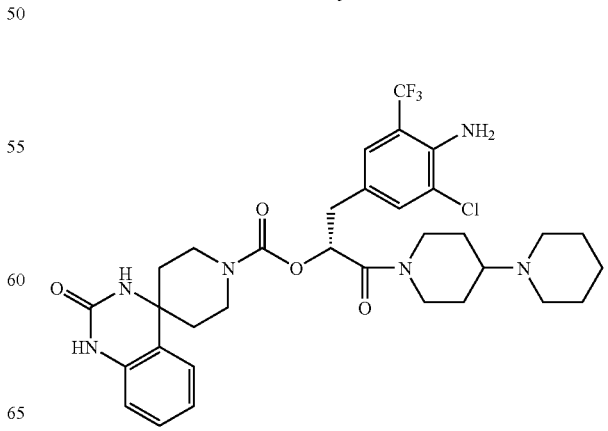

Analogously to Example (1c) the product was obtained from 100 mg (0.19 mmol)(R)-2-(4-amino-3-chloro-5-trifluoromethyl-phenyl)-1-carboxy-ethyl 1',2'-dihydro-2'-oxospiro-4H-3',1-quinazoline'-4,4'-piperidine-1-carboxylate and 40 mg (0.23 mmol) [1,4']bipiperidinyl.

| | |
|---|---|
| Yield: | 40 mg (31% of theory) |
| MS: | (M + H)⁺ = 677/679 (Cl) |
| $R_f=$ | 0.46 (silica gel, DCM/Cyc/MeOH/NH₃ 70:15:15:2) |

EXAMPLE 5

(R)-1-(4-amino-3-chloro-5-trifluoromethyl-benzyl)-2-[4-(4-methyl-piperazin-1-yl)-piperidin 1-yl]-2-oxo-ethyl 1',2'-dihydro-2'-oxospiro-4H-3',1-benzoxazin-4,4'-piperidine-1-carboxylate

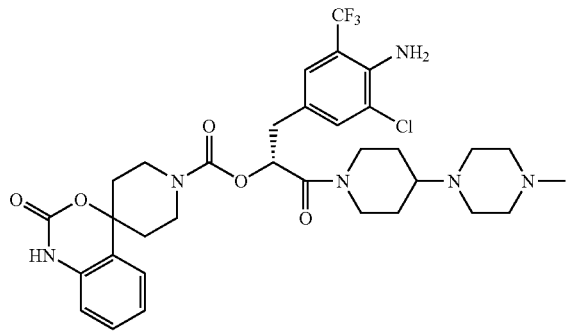

(5a) (R)-2-(4-amino-3-chloro-5-trifluoromethyl-phenyl)-1-methoxycarbonyl-ethyl 1',2'-dihydro-2'-oxospiro-4H-3',1-benzoxazin-4,4'-piperidine-1-carboxylate Analogously to Example (1a) the product was obtained from 1.5 g (5.04 mmol) methyl(R)-3-(4-amino-3-chloro-5-trifluoromethyl-phenyl)-2-hydroxy-propionate and 1.2 g (5.50 mmol) 1',2'-dihydro-2'-oxospiro-4H-3',1-benzoxazin-4,4'-piperidine.

| | |
|---|---|
| Yield: | 0.85 g (31% of theory) |
| MS: | (M + H)⁺ = 542/544 (Cl) |
| $R_f=$ | 0.56 (silica gel, DCM/Cyc/MeOH/NH₃ 70:15:15:2) |

(5b)(R)-2-(4-amino-3-chloro-5-trifluoromethyl-phenyl)-1-carboxy-ethyl 1',2'-dihydro-2'-oxospiro-4H-3',1-benzoxazin-4,4'-piperidine-1-carboxylate Analogously to Example (1b) the product was obtained from 850 mg (1.57 mmol)(R)-2-(4-amino-3-chloro-5-trifluoromethyl-phenyl)-1-methoxycarbonyl-ethyl 1',2'-dihydro-2'-oxospiro-4H-3',1-benzoxazin-4,4'-piperidine-1-carboxylate and 80 mg (3.27 mmol) LiOH.

| | |
|---|---|
| Yield: | 570 mg (69% of theory) |
| MS: | (M + H)⁺ = 528/530 (Cl) |
| $R_f=$ | 0.10 (silica gel, DCM/Cyc/MeOH/NH₃ 70:15:15:2) |

(5c) (R)-1-(4-amino-3-chloro-5-trifluoromethyl-benzyl)-2-[4-(4-methyl-piperazin-1-yl)-piperidin-1-yl]-2-oxo-ethyl 1',2'-dihydro-2'-oxospiro-4H-3',1-benzoxazin-4,4'-piperidine-1-carboxylate Analogously to Example (1c) the product was obtained from 100 mg (0.19 mmol)(R)-2-(4-amino-3-chloro-5-trifluoromethyl-phenyl)-1-carboxy-ethyl 1',2'-dihydro-2'-oxospiro-4H-3',1-benzoxazin-4,4'-piperidine-1-carboxylate and 40 mg (0.21 mmol) 1-methyl-4-piperidin-4-yl-piperazine.

| | |
|---|---|
| Yield: | 70 mg (53% of theory) |
| MS: | (M + H)⁺ = 693/695 (Cl) |
| $R_f=$ | 0.46 (silica gel, DCM/Cyc/MeOH/NH₃ 70:15:15:2) |

EXAMPLE 6

(R)-1-(4-amino-3-chloro-5-trifluoromethyl-benzyl)-2-[4-(1-methyl-piperidin-4-yl)-piperazin-1-yl]-2-oxo-ethyl 1',2'-dihydro-2'-oxospiro-4H-3',1-benzoxazin-4,4'-piperidine-1-carboxylate

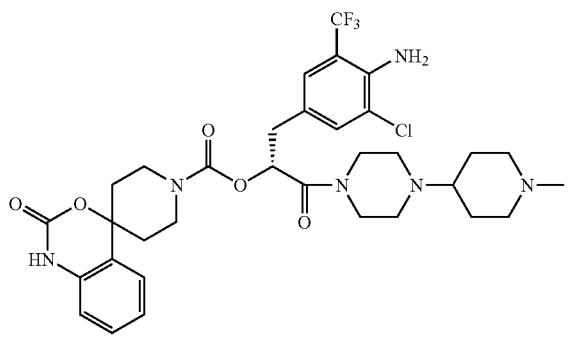

Analogously to Example (1c) the product was obtained from 100 mg (0.19 mmol)(R)-2-(4-amino-3-chloro-5-trifluoromethyl-phenyl)-1-carboxy-ethyl 1',2'-dihydro-2'-oxospiro-4H-3',1-benzoxazin-4,4'-piperidine-1-carboxylate and 40 mg (0.22 mmol) 1-(1-methyl-piperidin-4-yl)-piperazine.

| | |
|---|---|
| Yield: | 50 mg (38% of theory) |
| MS: | (M + H)⁺ = 693/695 (Cl) |
| $R_f=$ | 0.34 (silica gel, DCM/Cyc/MeOH/NH₃ 70:15:15:2) |

EXAMPLE 7

(R)-1-(4-amino-3-chloro-5-trifluoromethyl-benzyl)-2-(1'-methyl-[4,4']bipiperidinyl-1-yl)-2-oxo-ethyl 1',2'-dihydro-2'-oxospiro-4H-3',1-benzoxazin-4,4'-piperidine-1-carboxylate

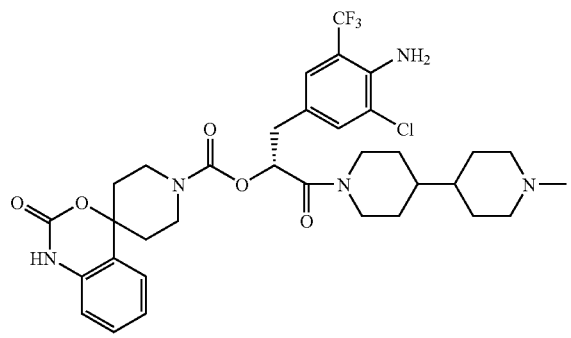

Analogously to Example (1c) the product was obtained from 100 mg (0.19 mmol)(R)-2-(4-amino-3-chloro-5-trifluoromethyl-phenyl)-1-carboxy-ethyl 1',2'-dihydro-2'-oxospiro-4H-3',1-benzoxazin-4,4'-piperidine-1-carboxylate and 40 mg (0.22 mmol) 1-methyl-[4,4']bipiperidinyl.

| Yield: | 40 mg (30% of theory) |
|---|---|
| MS: | $(M + H)^+ = 692/694$ (Cl) |
| $R_f =$ | 0.38 (silica gel, DCM/Cyc/MeOH/$NH_3$ 70:15:15:2) |

EXAMPLE 8

(R)-1-(4-amino-3-chloro-5-trifluoromethyl-benzyl)-2-[1,4']bipiperidinyl-1'-yl-2-oxo-ethyl 1',2'-dihydro-2'-oxospiro-4H-3',1-benzoxazin-4,4'-piperidine-1-carboxylate

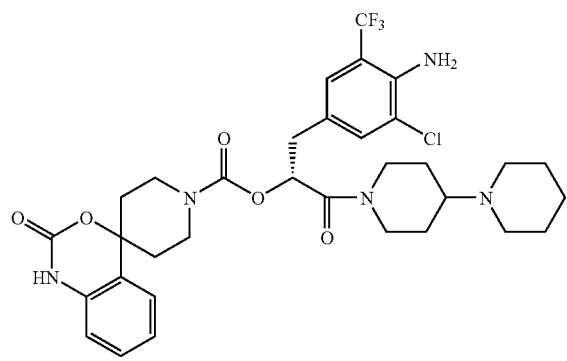

Analogously to Example (1c) the product was obtained from 100 mg (0.19 mmol)(R)-2-(4-amino-3-chloro-5-trifluoromethyl-phenyl)-1-carboxy-ethyl 1',2'-dihydro-2'-oxospiro-4H-3',1-benzoxazin-4,4'-piperidine-1-carboxylate and 40 mg (0.23 mmol) [1,4']bipiperidinyl.

| Yield: | 40 mg (31% of theory) |
|---|---|
| MS: | $(M + H)^+ = 678/680$ (Cl) |
| $R_f =$ | 0.44 (silica gel, DCM/Cyc/MeOH/$NH_3$ 70:15:15:2) |

The following Examples describe the preparation of pharmaceutical formulations which contain as active substance any desired compound of general formula (I):

EXAMPLE I

Capsules for Powder Inhalation Containing 1 mg of Active Ingredient

Composition:

1 capsule for powder inhalation contains:

| active ingredient | 1.0 mg |
|---|---|
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

EXAMPLE II

Inhalable Solution for Respimat® Containing 1 mg of Active Ingredient

Composition:

1 puff contains:

| active ingredient | 1.0 mg |
|---|---|
| benzalkonium chloride | 0.002 mg |
| disodium edetate | 0.0075 mg |
| purified water ad | 15.0 µl |

Method of Preparation:

The active ingredient and benzalkonium chloride are dissolved in water and transferred into Respimat® cartridges.

EXAMPLE III

Inhalable Solution for Nebulisers Containing 1 mg of Active Ingredient

Composition:

1 vial contains:

| active ingredient | 0.1 g |
|---|---|
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

EXAMPLE IV

Propellant Gas-Operated Metering Aerosol Containing 1 mg of Active Ingredient

Composition:

1 puff contains:

| | |
|---|---|
| active ingredient | 1.0 mg |
| lecithin | 0.1% |
| propellant gas ad | 50.0 μl |

Method of Preparation:

The micronised active ingredient is homogeneously suspended in the mixture of lecithin and propellant gas. The suspension is transferred into a pressurised container with a metering valve.

EXAMPLE V

Nasal Spray Containing 1 mg of Active Ingredient

Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

EXAMPLE VI

Injectable Solution Containing 5 mg of Active Substance Per 5 ml

Composition:

| | |
|---|---|
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (Wfl); human serum albumin is added; active ingredient is dissolved with heating; made up to specified volume with Wfl; transferred into ampoules under nitrogen gas.

EXAMPLE VII

Injectable Solution Containing 100 mg of Active Substance Per 20 ml

Composition:

| | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

EXAMPLE VIII

Lyophilisate Containing 10 mg of Active Substance

Composition:

| | |
|---|---|
| Active substance | 10 mg |
| Mannitol | 300 mg |
| human serum albumin | 20 mg |

Preparation:

Mannitol is dissolved in water for injections (Wfl); human serum albumin is added; active ingredient is dissolved with heating; made up to specified volume with Wfl; transferred into vials; freeze-dried.

Solvent for Lyophilisate:

| | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (Wfl); transferred into ampoules.

EXAMPLE IX

Tablets Containing 20 mg of Active Substance

Composition:

| | |
|---|---|
| active substance | 20 mg |
| lactose | 120 mg |
| maize starch | 40 mg |
| magnesium stearate | 2 mg |
| Povidone K 25 | 18 mg |

Preparation:

Active substance, lactose and maize starch are homogeneously mixed; granulated with an aqueous solution of Povidone; mixed with magnesium stearate; compressed in a tablet press; weight of tablet 200 mg.

EXAMPLE X

Capsules Containing 20 mg Active Substance

Composition:

| active substance | 20 mg |
|---|---|
| maize starch | 80 mg |
| highly dispersed silica | 5 mg |
| magnesium stearate | 2.5 mg |

Preparation:
Active substance, maize starch and silica are homogeneously mixed; mixed with magnesium stearate; the mixture is packed into size for 3 hard gelatine capsules in a capsule filling machine.

EXAMPLE XI

Suppositories Containing 50 mg of Active Substance

Composition:

| active substance | 50 mg |
|---|---|
| hard fat (Adeps solidus) q.s. ad | 1700 mg |

Preparation:
Hard fat is melted at about 38° C.; ground active substance is homogeneously dispersed in the molten hard fat; after cooling to about 35° C. it is poured into chilled moulds.

EXAMPLE XII

Injectable Solution Containing 10 mg of Active Substance Per 1 ml

Composition:

| active substance | 10 mg |
|---|---|
| mannitol | 50 mg |
| human serum albumin | 10 mg |
| water for injections ad | 1 ml |

Preparation:
Mannitol is dissolved in water for injections (Wfl); human serum albumin is added; active ingredient is dissolved with heating; made up to specified volume with Wfl; transferred into ampoules under nitrogen gas.

What is claimed is:
1. A compound of the formula

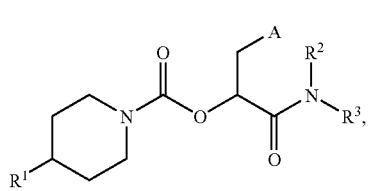

(I)

wherein
A denotes a group of formula

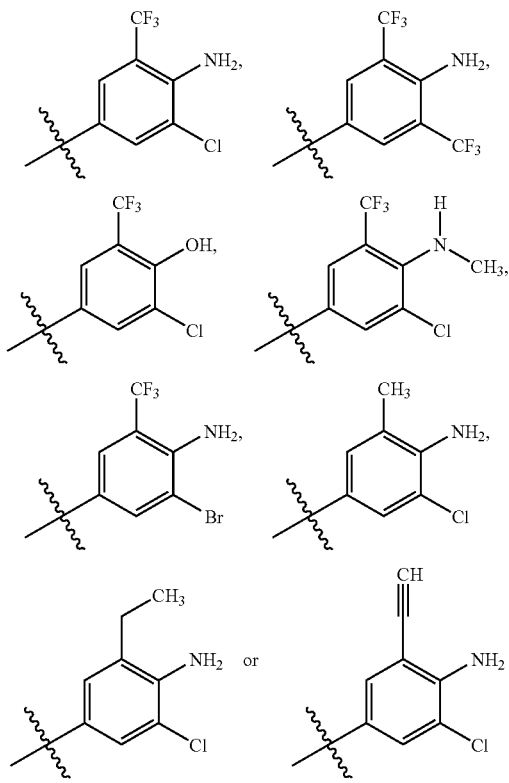

the group

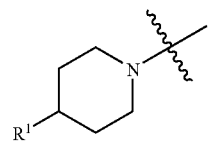

denotes a group of formula

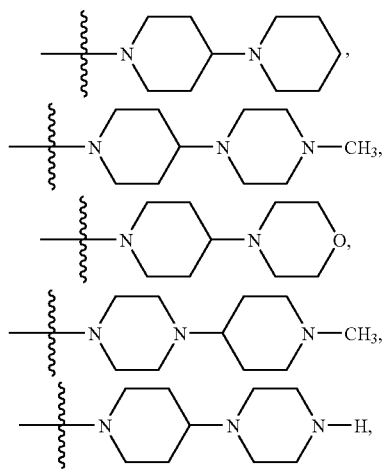

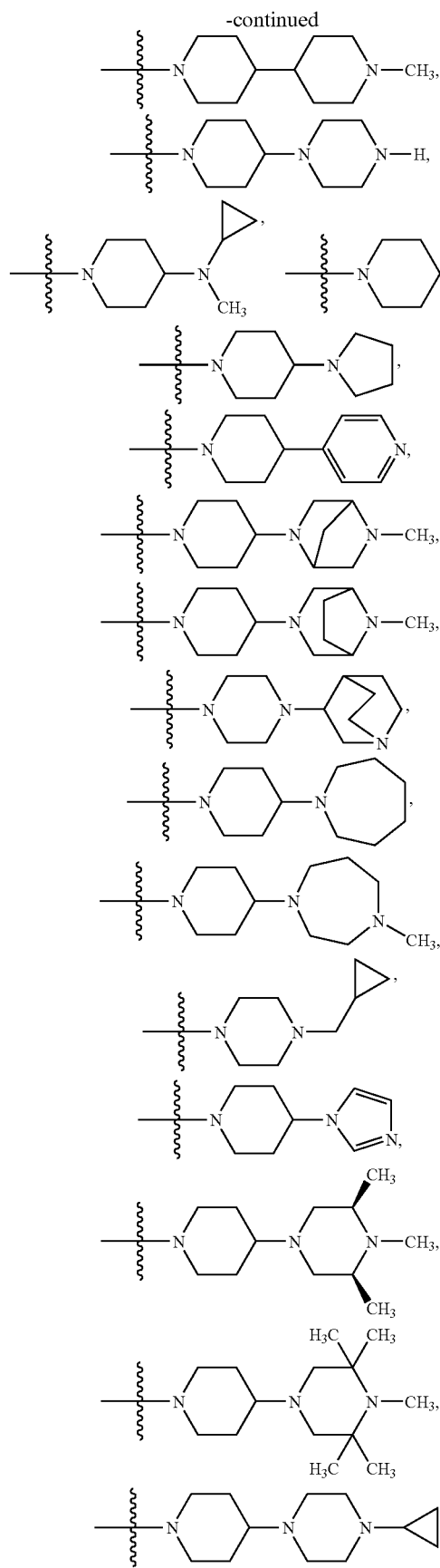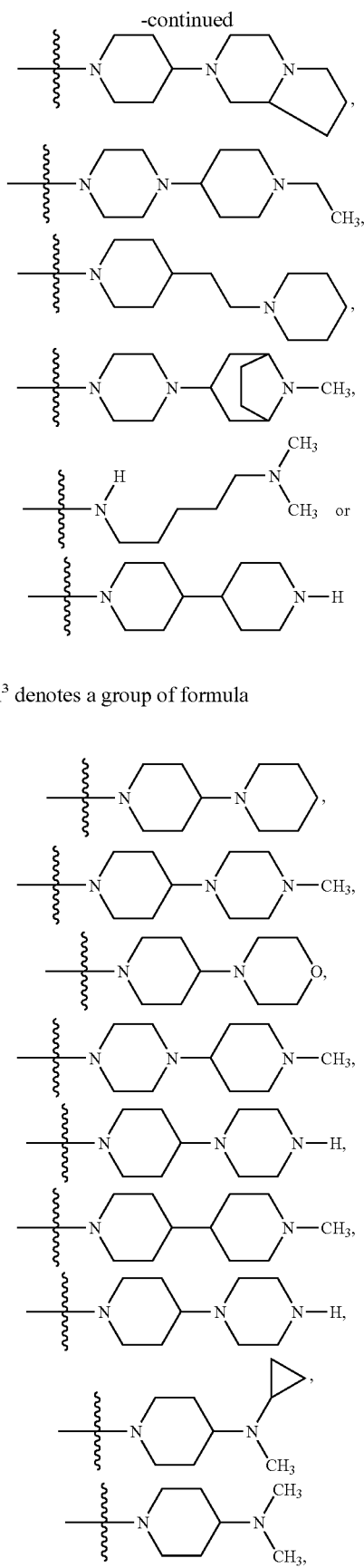
—$NR^2R^3$ denotes a group of formula

-continued
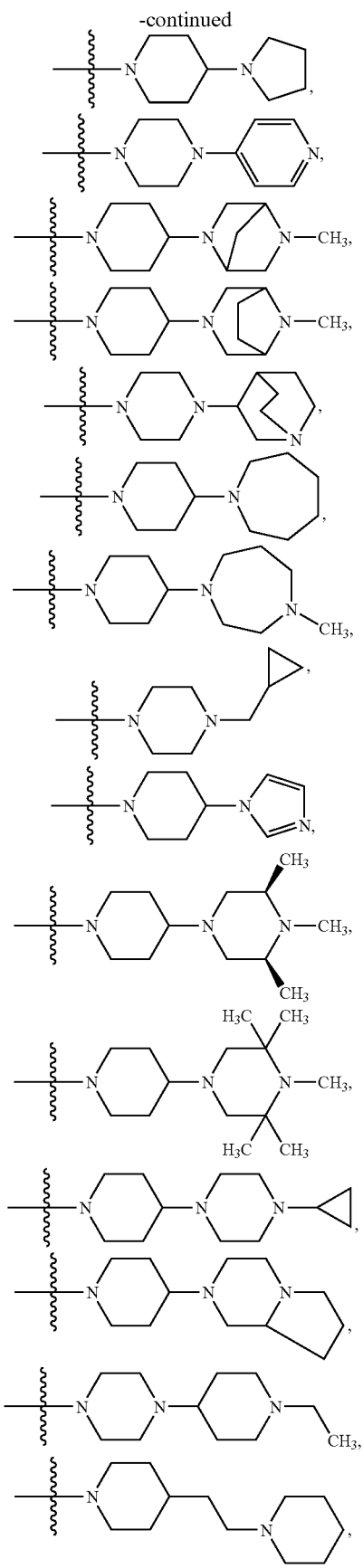
-continued
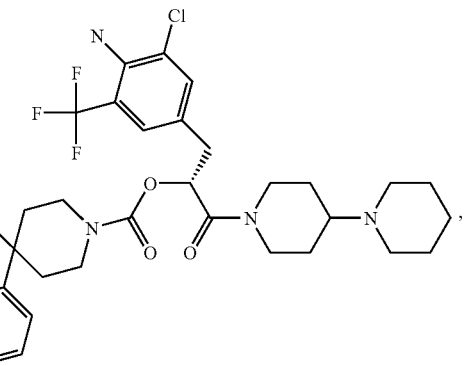
or a tautomer or salt thereof.
2. A compound of the formula (I) according to claim 1, selected from the group consisting of:
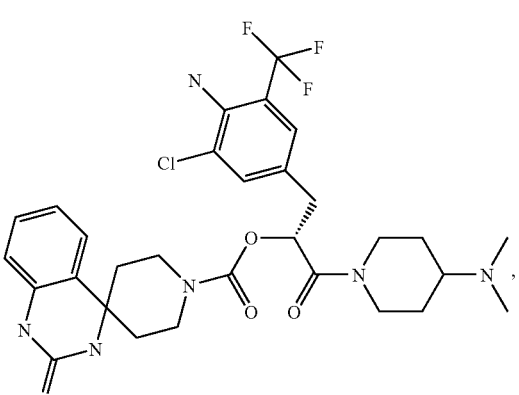
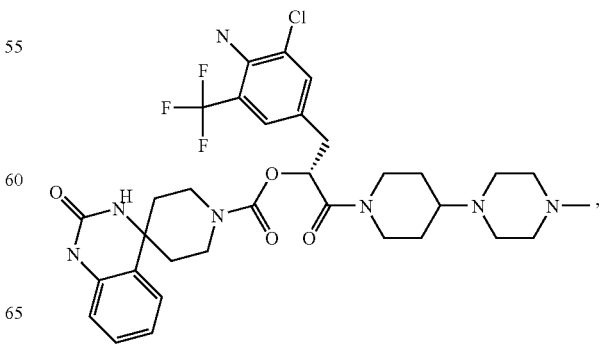

250
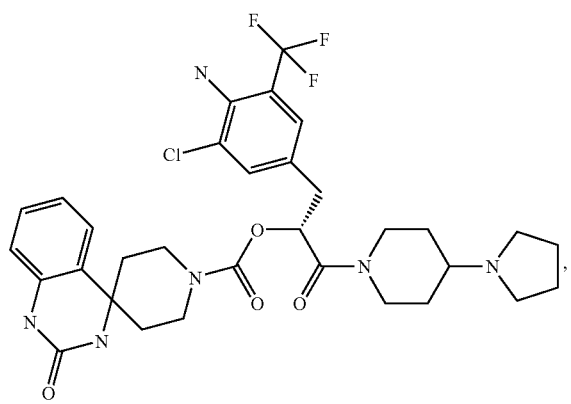
254
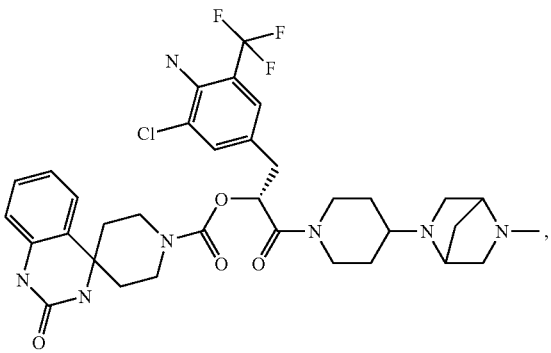
251
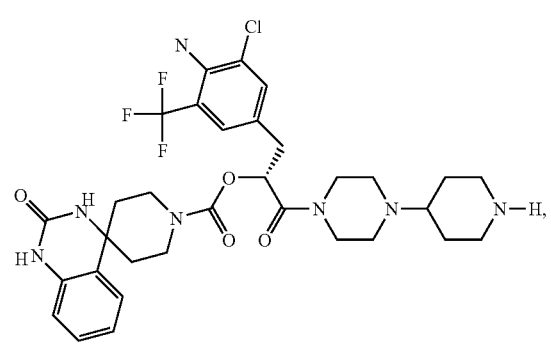
255
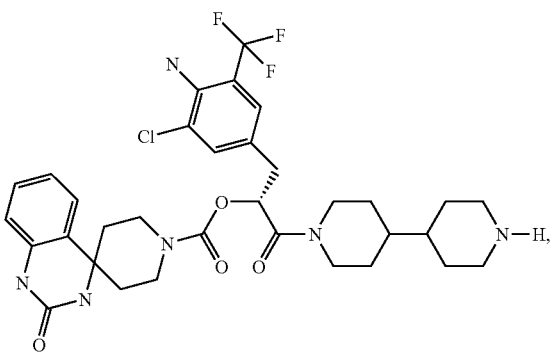
252
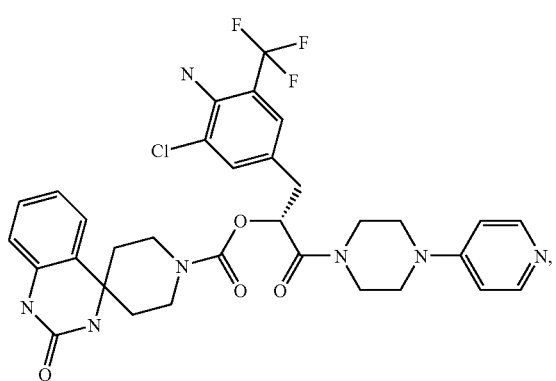
256
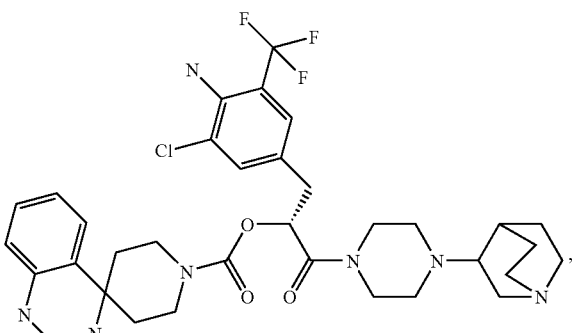
253
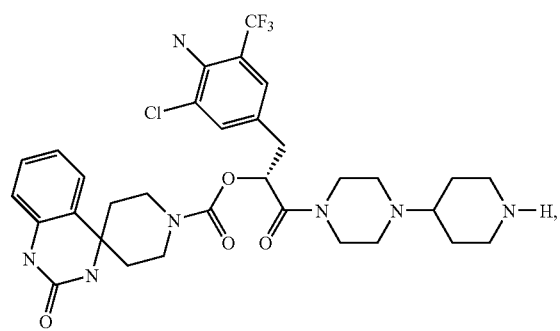
257
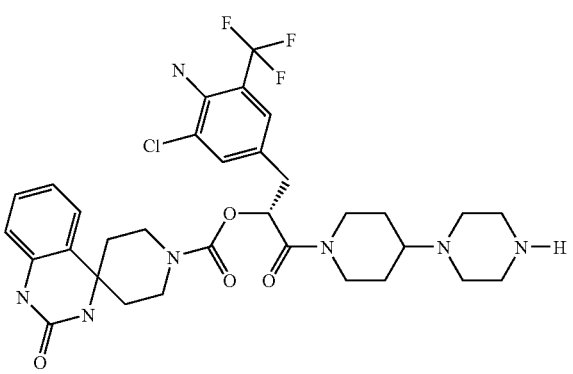
and -continued

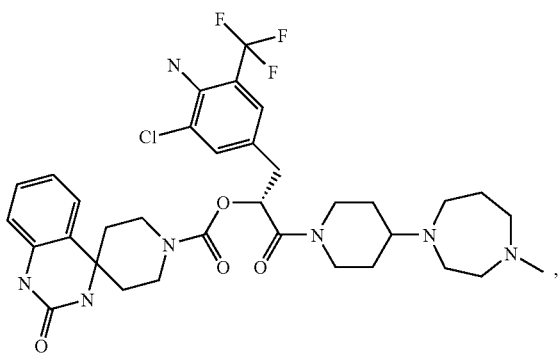

258 or a tautomer or salt thereof.

3. A compound of the formula (I) according to claim 1, selected from the group consisting of:
(a) (R)-1-(4-amino-3-chloro-5-trifluoromethyl-benzyl)-2-[4-(4-methyl-piperazin-1-yl)-piperidin-1-yl]-2-oxo-ethyl 1',2'-dihydro-2'-oxospiro-4H-3',1-quinazoline'-4,4'-piperidine-1-carboxylate,
(b) (R)-1-(4-amino-3-chloro-5-trifluoromethyl-benzyl)-2-[4-(1-methyl-piperidin-4-yl)-piperazin-1-yl]-2-oxo-ethyl 1',2'-dihydro-2'-oxospiro-4H-3',1-quinazoline'-4,4'-piperidine-1-carboxylate,
(c) (R)-1-(4-amino-3-chloro-5-trifluoromethyl-benzyl)-2-(1'-methyl-[4,4']bipiperidinyl-1-yl)-2-oxo-ethyl 1',2'-dihydro-2'-oxospiro-4H-3',1-quinazoline'-4, 4'-piperidine-1-carboxylate,
(d) (R)-1-(4-amino-3-chloro-5-trifluoromethyl-benzyl)-2-[1,4']bipiperidinyl-1'-yl-2-oxo-ethyl 1',2'-dihydro-2'-oxospiro-4H-3',1-quinazoline'-4,4'-piperidine-1-carboxylate, or a tautomer or salt thereof.

4. A physiologically acceptable salt of a compound according to claim 1.

5. A pharmaceutical composition containing a compound according to claim 1 or a physiologically acceptable salt thereof, together with one or more inert carriers and/or diluents.

6. A method for treating migraine or cluster headaches which comprises administering to a host in need of such treatment a therapeutically effective amount of a compound according to claim 1 or a physiologically acceptable salt thereof.

7. A method for treating non-insulin-dependent diabetes mellitus (NIDDM) which comprises administering to a host in need of such treatment a therapeutically effective amount of a compound according to claim 1 or a physiologically acceptable salt thereof.

8. A physiologically acceptable salt of a compound according to claim 2.

9. A physiologically acceptable salt of a compound according to claim 3.

10. A pharmaceutical composition containing a compound according to claim 2 or a physiologically acceptable salt thereof, together with one or more inert carriers and/or diluents.

11. A pharmaceutical composition containing a compound according to claim 3 or a physiologically acceptable salt thereof, together with one or more inert carriers and/or diluents.

12. A method for treating migraine or cluster headaches which comprises administering to a host in need of such treatmetn a therapeutically effective amount of a compound according to claim 2 or a physiologocally acceptable salt thereof.

13. A method for treating migraine or cluster headaches which comprises administering to a host in need of such treatment a therapeutically effective amount of a compound according to claim 3 or a physiologically acceptable salt thereof.

14. A method for treating non-insulin-dependent diabetes mellitus (NIDDM) which comprises administering to a host in need of such treatment a therapeutically effective amount of a compound according to claim 2 or a physiologically acceptable salt thereof.

15. A method for treating non-insulin-dependent diabetes mellitus (NIDDM) which comprises administering to a host in need of such treatment a therapeutically effective amount of a compound according to claim 3 or a physiologically acceptable salt thereof.

* * * * *